(12) United States Patent
Thompson et al.

(10) Patent No.: US 7,368,111 B2
(45) Date of Patent: May 6, 2008

(54) HUMAN ANTIBODIES SPECIFIC FOR TGFβ2

(75) Inventors: Julia Elizabeth Thompson, Herts (GB); Tristan John Vaughan, Cambridge (GB); Andrew James Williams, Fowlmere (GB); Jonathan Alexander Green, Cambridgeshire (GB); Ronald Henry Jackson, Cambridge (GB); Louise Bacon, Cambs (GB); Kevin Stuart Johnson, Cambs (GB); Alison Jane Wilton, Cambridge (GB); Philip Ronald Tempest, Cambridge (GB); Raymond Paul Field, Hertfordshire (GB); Steven Paul Ruddock, Cambridge (GB); Gregory Paul Winter, Chulmleigh (GB)

(73) Assignees: Cambridge Antibody Technology Limited, Cambridge (GB); Medical Research Council, London (GB)

( * ) Notice: Subject to any disclaimer, the term of this patent is extended or adjusted under 35 U.S.C. 154(b) by 429 days.

(21) Appl. No.: 10/625,307

(22) Filed: Jul. 23, 2003

(65) Prior Publication Data
US 2005/0049403 A1 Mar. 3, 2005

Related U.S. Application Data

(63) Continuation-in-part of application No. 08/571,755, filed on Dec. 13, 1995, now abandoned, and a continuation of application No. 09/054,847, filed on Apr. 3, 1998, now abandoned, which is a continuation of application No. PCT/GB96/02450, filed on Oct. 7, 1996.

(30) Foreign Application Priority Data

Oct. 6, 1995 (GB) .................................. 9520486
Jan. 19, 1996 (GB) .................................. 9601081

(51) Int. Cl.
A61K 39/395 (2006.01)
C07K 16/24 (2006.01)

(52) U.S. Cl. .............................. 424/145.1; 424/130.1; 424/133.1; 424/141.1; 424/142.1; 424/158.1; 530/387.1; 530/387.3; 530/388.1; 530/388.15; 530/388.23

(58) Field of Classification Search .................... None
See application file for complete search history.

(56) References Cited

U.S. PATENT DOCUMENTS

| 4,816,397 | A |   | 3/1989  | Boss et al. |
| 4,946,778 | A |   | 8/1990  | Ladner et al. |
| 5,091,513 | A |   | 2/1992  | Huston et al. |
| 5,223,409 | A |   | 6/1993  | Ladner et al. |
| 5,262,319 | A | * | 11/1993 | Iwata et al. ................. 435/378 |
| 5,395,750 | A |   | 3/1995  | Dillon et al. |
| 5,571,714 | A | * | 11/1996 | Dasch et al. ................. 435/336 |
| 5,585,089 | A |   | 12/1996 | Queen et al. |
| 5,616,561 | A |   | 4/1997  | Barcellos-Hoff |
| 5,662,904 | A |   | 9/1997  | Ferguson et al. |
| 5,772,998 | A |   | 6/1998  | Dasch et al. |
| 5,783,185 | A |   | 7/1998  | Dasch et al. |
| 5,885,793 | A |   | 3/1999  | Griffiths et al. |
| 5,962,255 | A |   | 10/1999 | Griffiths et al. |
| 6,090,383 | A |   | 7/2000  | Dasch et al. |
| 6,248,516 | B1 |  | 6/2001  | Winter et al. |
| 6,331,415 | B1 |  | 12/2001 | Cabilly et al. |
| 6,419,928 | B1 |  | 7/2002  | Dasch et al. |
| 6,492,497 | B1 | * | 12/2002 | Thompson et al. ..... 530/388.85 |

FOREIGN PATENT DOCUMENTS

| AU | B-27617/88 |   | 7/1989 |
| EP | A 0120694 |   | 10/1984 |
| EP | A 0125023 |   | 11/1984 |
| EP | A 184187 |   | 6/1986 |
| EP | A 0239400 |   | 9/1987 |
| EP | B 0239400 |   | 9/1987 |
| EP | 0 324 162 |   | 12/1988 |
| EP | 0 368 684 |   | 3/1994 |
| GB | 2188638 |   | 10/1987 |
| GB | 2 288 118 A |   | 10/1995 |
| GB | 9520486.3 | * | 10/1995 |
| GB | 9601081.4 | * | 1/1996 |
| WO | WO 88/06630 |   | 9/1988 |
| WO | WO 88/09344 |   | 12/1988 |
| WO | WO 90/02809 |   | 3/1990 |

(Continued)

OTHER PUBLICATIONS

Lucas et al., J. Immunol. 145: 1415-1422, 1990.*

(Continued)

Primary Examiner—Phillip Gambel
(74) Attorney, Agent, or Firm—Howrey LLP

(57) ABSTRACT

Specific binding members comprising human antibody antigen binding domains specific for human transforming growth factor beta (TGFβ) bind specifically isoforms TGFβ2 and TGFβ1 or both, preferentially compared with TGFβ3. Specific binding members may be isolated and utilized in the treatment of disease, particularly fibrotic disease and also immune/inflammatory diseases. Therapeutic utility is demonstrated using in vitro and in vivo models. Full sequence and binding information is provided, including epitope sequence information for particularly advantageous specific binding member which binds the active form of TGFβ2, neutralizing its activity, but does not bind the latent member.

20 Claims, 54 Drawing Sheets

FOREIGN PATENT DOCUMENTS

| WO | WO 90/05144 | 5/1990 |
| --- | --- | --- |
| WO | WO 90/14424 | 11/1990 |
| WO | WO 90/14430 | 11/1990 |
| WO | WO 90/14443 | 11/1990 |
| WO | WO 91/04748 | 4/1991 |
| WO | WO 91/10737 | 7/1991 |
| WO | WO 91/17271 | 11/1991 |
| WO | WO 92/01047 | 1/1992 |
| WO | WO 92/06204 | 4/1992 |
| WO | WO 92/09690 | 6/1992 |
| WO | WO 92/17206 | 10/1992 |
| WO | WO 92/18619 | 10/1992 |
| WO | WO 92/20791 | 11/1992 |
| WO | WO 93/06213 | 4/1993 |
| WO | WO 93/11161 | 6/1993 |
| WO | WO 93/11236 * | 6/1993 |
| WO | WO 93/14782 | 8/1993 |
| WO | WO 93/17708 | 9/1993 |
| WO | WO 93/19783 | 10/1993 |
| WO | WO 93/21945 | 11/1993 |
| WO | WO 94/13804 | 6/1994 |
| WO | WO 94/18227 | 8/1994 |
| WO | WO 95/13827 | 5/1995 |
| WO | WO 97/13844 | 4/1997 |

OTHER PUBLICATIONS

Rudikoff et al., Proc Natl Acad Sci USA 79: 1979-1983, 1982.*
Colman, Research in Immunology 145: 33-36, 1994.*
Bouanani, M. et al., "Autoimmunity to Human Thyroblobulin," Arthritis and Rheumatism, 34(12):1585-1593 (1991).
James, K. and Bell, G.T., "Human Monoclonal Antibody Production: Current Status and Future Prospects," Journal of Immunological Methods, 100:5-40 (1987).
Kim, J.G. and Abeyounis, C.J., "Isolation and Characterization of Rat Carcinoembryonic Antigen," Int. Arch. Allergy Appl. Immunol., 92:43-49 (1990).
Kim, J.G. and Abeyounis, C.J., "Monoclonal Rat Antibodies to Rat Carcinoembryonic Antigen," Immunological Investigations, 17(1):41-48 (1988).
Portolano, S. et al., "A Human FAB Fragment Specific for Thyroid Peroxidase Generated by Cloning Thyroid Lymphocyte-Derived Immunoglobulin Genes in a Bacteriophage Lambda Library," Biochemical and Biophysical Research Communications, 179(1):372-377 (1991).
Avrameas, "Natural Autoantibodies: From 'Horror Autotoxicus'to 'Gnothi Seauton'", Immunology Today 12:154-159 (1991).
Bass et al., "Hormone Phage: An Enrichment Method for Variant Proteins With Altered Binding Properties," Proteins, Structure, Function and Genetics 8:309-314 (1990).
Bendtzen et al., "Autoantibodies to Cytokines—Friends or Foes?," Immunology Today 11(5):167-169 (1990).
de la Cruz et al., "Immunogenicity and Epitope Mapping of Foreign Sequences via Genetically Engineered Filamentous Phage," J. Biol. Chem. 263(9):4318-4322 (1988).
Ditzel et al., "The Nature of the Autoimmune Antibody Repertoire in Human Immunodeficiency Virus Type 1 Infection," Proc. Natl. Acad. Sci. USA 91:3710-3714 (1994).
Hassan et al., "Prevalence of Anti-Fab Antibodies in Patients with Autoimmune and Infectious Diseases," Clin. exp. Immunol. 89:423-426 (1992).
Huse et al., "Generation of a Large Combinatorial Library of the Immunoglobulin Repertoire in Phage Lambda," Science 246:1275-1281 (1989).
Jerome et al., "Adenocarcinoma Reactive Cytotoxic T Lymphocytes Recognize an Epitope Present on the Protein Core of Epithelial Mucin Molecules," Cellular Immunity and the Immunotherapy of Cancer, pp. 321-328 (1990).
Kang et al., "Linkage of Recognition and Replication Functions by Assembling Combinatorial Antibody Fab Libraries Along Phage Surface," Proc. Natl. Acad. Sci. USA 88:4363-4366 (1991).

Leusch et al., "Failure to Demonstrate TNF α-Specific Autoantibodies in Human Sera by ELISA and Western Blot," Journal of Immunological Methods 139:145-147 (1991).
Marks et al., "By-Passing Immunization: Building High Affinity Human Antibodies by Chain Shuffling," Bio/Technology 10:779-783 (1992).
McCafferty et al., "Phage Antibodies: Filamentous Phage Displaying Antibody Variable Domains," Nature 348:552-554 (1990).
Milstein, F.R.S., "Antibodies: a Paradigm for the Biology of Molecular Recognition," Proc. R. Soc. London B 239:1-16 (1990).
Moynier et al., "The B Cell Repertoire in Rheumatoid Arthritis. I. Frequency of EBV-Inducible Circulating Precursors Producing Autoantibodies," Journal of Autoimmunity 4:631-649 (1991).
Nossal, "Immunologic Tolerance: Collaboration Between Antigen and Lymphokines," Science 245:147-153 (1989).
Parmley and Smith, "Antibody-Selectably Filamentous fd Phage Vectors: Affinity Purification of Target Genes," Gene 73:305-318 (1988).
Sanz et al., "Nucleotide Sequences of Eight Human Natural Autoantibody $V_H$ Regions Reveals Apparent Restricted Use of $V_H$ Families," The Journal of Immunology 142(11):4051-4061 (1989).
Sekigawa et al., "Characterization of Autoantibodies to the CD4 Molecule in Human Immunodeficiency Virus Infection," Clinical Immunology and Immunopathology 58:145-153 (1991).
Short et al., "λ ZAP: a Bacteriophage λ Expression Vector with In Vivo Excision Properties," Nucleic Acids Research 16(15):7583-7600 (1988).
Smith, "Filamentous Fusion Phage: Novel Expression Vectors That Display Cloned Antigens on the Virion Surface," Science 228:1315-1317 (1985).
Tsunetsugu-Yokota et al., "Expression of an Immunogenic Region of HIV by a Filamentous Bacteriophage Vector," Gene 99:261-265 (1991).
Winter and Milstein, "Man-Made Antibodies," Nature 349:293-299 (1991).
Yativ et al., "The Detection of Antithyroglobulin Activity in Human Serum Monoclonal Immunoglobulins (Monoclonal Gammopathies)," Immunol. Res. 12:330-337 (1993).
International Search Report: PCT/GB92/02240.
Border et al., "Suppression of Experimental Glomerulonephritis by Antiserum Against Transforming Growth Factor β1," Nature, 346:371-374 (1990).
Dasch et al., "Monoclonal Antibodies Recognizing Transforming Growth Factor-β: Bioactivity Neutralization and Transforming Growth Factor β2 Affinity Purification," J. Immunol., 142(5):1536-1541 (1989).
Larrick et al., "Recombinant Antibodies," Hum. Antibody. Hybridomas, 2:172-189 (1991).
Bagshawe et al., "Antibody-Enzyme Conjugates Can Generate Cytotoxic Drugs from Inactive Precursors at Tumor Sites," Antibody, Immunoconjugates and Radiopharmaceuticals, 4:915-922 (1991).
Barbas et al., "High-Affinity Self-Reactive Human Antibodies by Design and Selection: Targeting the Integrin Ligand Binding Site," Proc. Natl. Acad. Sci., USA, 90:10003-10007 (1993).
Barbas et al., "In Vitro Evolution of a Neutralizing Human Antibody to Human Immunodeficiency Virus Type 1 to Enhance Affinity and Broaden Strain Cross-Reactivity," Proc. Natl. Acad. Sci., USA, 91:3809-3813 (1994).
Bebbington et al., "High-Level Expression of a Recombinant Antibody From Myeloma Cells Using a Glutamine Synthetase Gene As An Amplifiable Selectable Marker," Bio/Technology, 10:169-175 (1992).
Bird R. et al., "Single-Chain Antigen-Binding Proteins," Science, 242:423-426 (1988).
Brown et al., "Physiochemical Activation of Recombinant Latent Transforming Growth Factor-beta's 1, 2, and 3," Growth Factors, 3:35-43 (1990).
Burmester et al., "Mutation Analysis of a Transforming Growth Factor-β Receptor Binding Site," Growth Factors, 15:231-242 (1998).

Bye et al., "Germline Variable of Gene Segment Derivation of Human Monoclonal Anti-Rh(D) Antibodies," J. Clin. Invest., 90(6):2481-2490.

Conner et al., "Correlation of Fibrosis and Tranforming Growth Factor-β type 2 Levels in the Eye," J. Clin. Invest., 83:1661-1666 (1989).

Danielpour et al., "Immunodetection and Quantitation of the Two Forms of Transforming Growth Factor-Beta (TGF-β1 and TGF-β2) Secreted by Cells in Culture," J. Cellular Physiology, 138:79-86 (1989).

Danielpour et al., "Sandwich Enzyme-Linked Immunosorbent Assays (SELISAs) Quantitate and Distinguish Two Forms of Transforming Growth Factor-Beta (TGF-β1 and TGF-β2) in Complex Biological Fluids," Growth Factors, 2:61-71 (1989).

Daopin et al., "Crystal Structure of TGF-β2 Refined at 1.8 A Resolution," Proteins: Structure, Function and Genetics, 17:176-192 (1993).

Derynck et al., "The Murine Transforming Growth Factor-β Precursor," J. Biol. Chem., 261:4377-4379 (1986).

Erlenbacher et al., "Increased Expression of TGF-β2 in Osteoblasts Results in an Osteoporosis-like Phenotype," J. Cell Biology, 132:195-210 (1996).

Fisch, I. et al., "A Strategy of Exon Shuffling for Making Large Peptide Repertoires Displayed on Filamentous Bacteriophage," Proc. Natl. Acad. Sci., USA, 93:7761-7766 (1996).

Flanders et al., "Antibodies to Peptide Determinants in Transforming Growth Factor β and Their Applications," Biochemistry, 27:739-746 (1988).

Flanders et al., "Antibodies to Transforming Growth Factor-β2 Peptides: Specific Detection of TGF-β2 in Immunoassays," Growth Factors, 3:45-52 (1990).

Flanders et al., "Localization and Actions of Transforming Growth Factor-βs in the Embryonic Nervous System," Development, 113:183-191 (1991).

Foreman et al., "A Simple Organ Culture Model for Assessing the Effects of Growth Factors on Corneal Re-epithelialization," Exp-Eye Res., 62:555-564 (1996).

Gibson, Toby James, Studies in the Epstein-Barr Virus Genome, University of Cambridge: Ph.D. Dissertation, Date approved: Dec. 7, 1984, BLDSC No. D58257/85, University of Cambridge, MRC Laboratory of Molecular Biology.

Giri et al., "Effect of Antibody to Transforming Growth Factor β on Bleomycin Induced Accumulation of Lung Collagen in Mice," Thorax, 48:959-966 (1993).

Gram et al., "In Vitro Selection and Affinity Maturation of Antibodies from a Naive Combinatorial Immunoglobulin Library," Proc. Natl. Acad. Sci., USA, 89 :3576-3580 (1992).

Griffiths, A.D. et al., "Human Anti-Self Antibodies with High Specificity From Phage Display Libraries," EMBO J., 12(2) :725-734 (1993).

Griffiths, A.D., et al., "Isolation of High Affinity Human Antibodies Directly from Large Synthetic Repertoires," EMBO J., 13(14) :3245-3260 (1994).

Griffiths et al., "Three-Dimensional Structure of Recombinant Human Osteogenic Protein 1 : Structural Paradigm for the Transforming Growth Factor b Superfamily, " Proc. Natl. Acad. Sci., USA, 93 :878-883 (1996).

Hoefer et al., "Anti-(Transforming Growth Factor β) Antibodies with Predefined Specificity Inhibit Metastatis of Highly Tumorigenic Human Xenotransplants in nu/nu Mice," Cancer Immunol. Immunother., 41:302-308 (1995).

Hollinger P. et al., "Engineering Bispecific Antibodies," Current Opinion in Biotechnology, 4:446-449 (1993).

Hollinger, P. et al., "'Diabodies': Small Bivalent and Bispecific Antibody Fragments," Proc. Natl. Acad. Sci., USA, 90:6444-6448 (1993).

Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Research, 56:3055-3061 (1996).

Huston J.S. et al., "Protein Engineering of Antibody Binding Sites: Recovery of Specific Activity in an Anti-digoxin Single-chain Fv Analogue Produced in *Escherichia coli*," Proc. Natl. Acad. Sci., USA, 85:5879-5883 (1988).

Ikeda et al., "Human Transforming Growth Factor Type β2: Production by a Prostatic Adenocarcinoma Cell Line, Purification, and Initial Characterization," Biochemistry, 26:2406-2410 (1987).

Jampel et al., "Transforming Growth Factor-β in Human Aqueous Humor," Currect Eye Research, 9:963-969 (1990).

Karlsson et al., "Kinetic Analysis of Monoclonal Antibody-Antigen Interactions with a New Biosensor Based Analytical System," J. Immunological Methods, 145:229-240 (1991).

Kaufman, R.J., "Selection and Coamplification of Heterologous Genes in Mammalian Cells," Methods Enzymology, 185:537-566 (1990).

Khaw et al., "Activation and Suppression of Fibroblast Function," Eye, 8:188-195 (1994).

Kvanta, A., "Expression and Secretion of Transforming Growth Factorβ in Transformed and Nontransformed Retinal Pigment Epithelial Cells," Opthalmic Res., 26:361-367 (1994).

Ledermann et al., "A Phase-I Study of Repeated Therapy with Radiolabelled Antibody to Carcinoembryonic Antigen Using Intermittent or Continuous Administration of Cyclosporin A to Suppress the Immune Response," Int. J. Cancer, 47:659-664 (1991).

Logan et al., "Effects of Transforming Growth Factor β1 on Scar Production in the Injured Central Nervous System of the Rat," European J. Neuroscience, 6:355-363 (1994).

Logan et al., "Enhanced Expression of Transforming Growth Factor β1 in the Rat Brain After a Localized Cerebral Injury," Brain Research, 587, P216-225 (1992).

Lucas et al., "Generation of Antibodies and Assays for Transforming Growth Factor β," Methods in Enzymology, 198:303-316 (1991).

Lucas et al., "The Autocrine Production of Transforming Growth Factor-$\oplus_1$ During Lymphocyte Activation," J. Immunology, 145:1415-1422 (1990).

Marks J.D. et al., "By-Passing Immunization Human Antibodies from V-gene Libraries Displayed on Phage," J. Molecular Biology, 222:581-597 (1991).

Massague et al., "The Transforming Growth Factor-β Family," Annual Rev. Cell Biol., 6:597-641 (1990).

McCafferty et al., "Selection and Rapid Purification of Murine Antibody Fragments that Bind a Transition-State Analog by Phage Display," Appl. Biochem. Biotech., 47:157-173 (1994).

Merwin et al., "Vascular Cells Respond Differentially to Transforming Growth Factors $Beta_1$ and $Beta_2$ In Vitro," American J. Pathology, 138:37-51 (1991).

Munro S. et al., "An Hsp70-like Protein in the ER: Identity with the 78 kd Glucose-Regulated Protein and Immunoglobulin Heavy Chain Binding Protein," Cell, 46:291-300 (1986).

Nissim et al., "Antibody Fragments from a 'Single Pot' Phage Display Library as Immunochemical Reagents," EMBO J., 13:692-698 (1994).

Orlandi, R. et al., "Cloning Immunoglobulin Variable Domains for Expression by the Polymerase Chain Reaction," Proc. Natl. Acad. Sci., USA, 86:3833-3837 (1989).

Ottman et al., "Differential Proliferative Effects of Transformign Growth Factor-β on Human Hematopoietic Progenitor Cells," J. Immunology, 140:2661-2665 (1988)

Pena et al., "Effects of TGF-β and TGF-β Neutralizing Antibodies on Fibroblast-Induced Collagen Gel Contraction: Implications for Proliferative Vitreoretinopathy," Investigative Ophthalmology Visual Science, 35:2804-2808 (1994).

Pfeffer et al., "Transforming Growth Factor Beta 2 is the Predominant Isoform in the Neural Retina, Retinal Epithelium-Choroid and Vitreous of the Monkey Eye," Exp. Eye Res., 59:323-33 (1994).

Pircher et al., "β-Transforming Growth Factor is Stored in Human Blood Platelets as a Latent High Molecular Weight Complex," Biochemical Biophysical Research Communications, 136(1):30-37 (1986).

Pluckthun, A., "Antibody Engineering: Advances From the Use of *Escherichia coli* Expression Systems," Bio/Technology, 9:545-551 (1991).

Qian et al., "Binding Affinity of Transforming Growth Factor-β for Its Type II Receptor is Determined by the C-terminal Region of the Molecule," J. Biol. Chem., 271:30656-30662 (1996).

Randall et al., "A Novel, Sensitive Bioassay for Transforming Growth Factor β," J. Immunological Methods, 164:61-67 (1993).

Reff, M.E., "High-level Production of Recombinant Immunoglobulins in Mammalian Cells," Current Opinion in Biotechnology, 4:573-576 (1993).

Reiter et al., "Engineering Antibody Fv Fragments for Cancer Detection and Therapy: Disulfide-Stabilized Fv Fragments," Nature Biotechnology, 14:1239-1245 (1996).

Ridgeway et al., "'Knos-into-holes' Engineering of Antibody $C_H3$ Domain for Heavy Chain Heterodimerization," Protein Engineering, 9:616-621 (1996).

Roberts et al., "Mesoderm induction in *Xenopus laevis* Distinguishes Between the Various TGF-β Isoforms," Growth Factors, 3:277-286 (1990).

Roberts et al., "The Transforming Growth Factor-βs" in Handbook of Experimental Pharmacology, Eds. M.B. Sporn et al., Springer Heideberg, pp. 419-472 (1990).

Schier et al., "Isolation of Picomolar Affinity Anti-c-erbB-2 Single-Chain Fv by Molecular Evolution of the Complementarity Determining Regions in the Center of the Antibody Binding Site," J. Mol. Biol., 263:551-567 (1996).

Schlunegger et al., "An Unusual Feature Revealed by the Crystal Structure at 2.2A Resolution of Human Transforming Growth Factor-β2," Nature, 358:430-434 (1992).

Shah et al., "Control of Scarring in Adult Wounds by Neutralizing Antibody to Transforming Growth Factor β," Lancet, 339:213-214 (1992).

Shah et al., "Neutralizing Antibody to TGF-$β_{1,2}$ Reduces Cutaneous Scarring in Adult Rodents," J. Cell Science, 107:1137-1157 (1994).

Shah M. et al., "Neutralization of TGF-$β_1$ and TGF-$β_2$ or Exogenous Addition of TGF-b3 to Cutaneous Rat Wounds Reduces Scarring," J. Cell Science, 108:985-1002 (1995).

Stemmer et al., "Rapid Evolution of a Protein In Vitro by DNA Shuffling," Nature, 370:389-391 (1994).

Saurdet et al., "Responsiveness of Three Newly Established Human Colorectal Cancer Cell Lines Transforming Growth Factors $β_1$ and $β_2$," Cancer Research, 52:3705-3712 (1992).

Tahara et al., "Synthetic Peptide-Generated Monoclonal Antibodies to Transforming Growth Factor-β1," Hybridoma, 12(4):441-453 (1993).

Traunecker, A. et al., "Bispecific Single Chain Molecules (Janusins) Target Cytotoxic Lymphocytes on HIV Infected Cells," EMBO J., 10(12):3655-3659 (1991).

Trill J.J. et al., "Production of Monoclonal Antibodies in COS and CHO Cells," Current Opinion in Biotechnology, 6:553-560 (1995).

Wahl et al., "Reversal of Acute and Chronic Synovial Inflammation by Anti-Transforming Growth Factor β," J. Experimental Medicine, 177:225-230 (1993).

Wakefield et al., "Recombinant TGF-β1 is Synthesized as a Two-Component Latent Complex That Shares Some Structural Features with the Native Platelet Latent TGF-β1 Complex," Growth Factors, 1:203-218 (1989).

Ward, E.S. et al., "Binding Activities of a Repertoire of Single Immunoglobulin Variable Domains Secreted from *Escherichia coli*," Nature, 341:544-546 (1989).

Winter, G. et al., "Man-Made Antibodies," Nature, 349:293-299 (1991).

Wolf et al., "Antibodies Against Transforming Growth Factor-β1 Suppress Intimal Hyperplasia in a Rat Model," J. Clin. Invest., 93:1172-1178 (1994).

Tempest, P. et al., "Human Antibodies Specific for Human TGF-b Derived from Phage Display Libraries," Immunotechnology, 2(4):306 (1996).

\* cited by examiner

Figure 1 Sequences of antibodies specific for TGFbeta (a) Antibodies to TGFbeta1 isolated directly from repertoires (i) 1B2 VH (also known as 7A3 VH)

Sequence Range: 1 to 369

```
         10         20         30         40
          *          *          *          *
CAG GTG CAA CTG GTG GAG TCT GGG GGA GGC GTG CAG CCT GGG AGG
 Q   V   Q   L   V   E   S   G   G   G   V   Q   P   G   R>
  a   a   a    TRANSLATION OF 7A3 VH.SEQ [A]  a   a   a   a 50         60         70         80         90
          *          *          *          *          *
TCC CTG AGA CTC TCC TGT GCA GCC TCT GGA TTC ACC TTC AGT AGC TAT
 S   L   R   L   S   C   A   A   S   G   F   T   F   S   S   Y>
  a   a    TRANSLATION OF 7A3 VH.SEQ [A]  a   a   a   a   a 100        110        120        130        140
          *          *          *          *          *
GGC ATG CAC TGG GTC CGC CAG GCT CCA GGC AAG GGG CTG GAG TGG GTG
 G   M   H   W   V   R   Q   A   P   G   K   G   L   E   W   V>
  a    TRANSLATION OF 7A3 VH.SEQ [A]  a   a   a   a   a   a 150        160        170        180        190
          *          *          *          *          *
GCA GTT ATA TCA TAT GAT GGA AGT AAT AAA TAC TAT GCA GAC TCC GTG
 A   V   I   S   Y   D   G   S   N   K   Y   Y   A   D   S   V>
  a    TRANSLATION OF 7A3 VH.SEQ [A]  a   a   a   a   a   a 200        210        220        230        240
          *          *          *          *          *
AAG GGC CGA TTC ACC ATC TCC AGA GAC AAT TCC AAG AAC ACG CTG TAT
 K   G   R   F   T   I   S   R   D   N   S   K   N   T   L   Y>
  a   a    TRANSLATION OF 7A3 VH.SEQ [A]  a   a   a   a   a
```

```
                    250           260           270           280
                     *             *             *             *
CTG CAA ATG AAC AGC CTG AGA GCT GAG GAC ACG GCT GTG TAT TAC TGT
 L   Q   M   N   S   L   R   A   E   D   T   A   V   Y   Y   C  __a__a__TRANSLATION OF 7A3 VH.SEQ [A]__a__a__a__>

290           300           310           320           330
 *             *             *             *             *
GCG AAA ACT GGG GAA TAT AGT GGC TAC GAT TCT AGT GGT GTG GAC GTC
 A   K   T   G   E   Y   S   G   Y   D   S   S   G   V   D   V  __a__a__TRANSLATION OF 7A3 VH.SEQ [A]__a__a__a__>

340           350           360
 *             *             *
TGG GGC AAA GGG ACC ACG GTC ACC GTC TCC TCA   (SEQ ID NO:7)
 W   G   K   G   T   T   V   T   V   S   S>  (SEQ ID NO:8)
__a__TRANSLATION OF 7A3 VH.SEQ [A]__a__>
```

(ii) <u>1A-E5 VH</u>

Sequence Range: 1 to 345

```
                    10            20            30            40
                     *             *             *             *
GAG GTG CAG CTG GTG GAG TCT GGT GGA GGC TTA GTT CAG CCT GGG GGG
 E   V   Q   L   V   E   S   G   G   G   L   V   Q   P   G   G  __a__a__a__TRANSLATION OF 1AE-5 VH [A]__a__a__a__>

50            60            70            80            90
 *             *             *             *             *
TCC CTG AGA CTC TCC TGT GCA GCC TCT GGA TTC ACC TTC AGT AGC TAC
 S   L   R   L   S   C   A   A   S   G   F   T   F   S   S   Y  __a__a__a__TRANSLATION OF 1AE-5 VH [A]__a__a__a__>

100           110           120           130           140
 *             *             *             *             *
```

```
TGG ATG CAC TGG GTC CGC CAA GCT CCA GGG AAG GGG CTG GTG TGG GTC
 W   M   H   W   V   R   Q   A   P   G   K   G   L   V   W   V >
___a___a___a_TRANSLATION OF 1AE-5 VH [A]___a___a___a___a___a___a >
            150                 160                 170                 180                 190
             *                   *                   *                   *                   *
TCA CGT ATT AAT AGT GAT GGG AGT ACA AGC TAC GCG GAC TCC GTG
 S   R   I   N   S   D   G   S   T   S   Y   A   D   S   V >
___a___a___a_TRANSLATION OF 1AE-5 VH [A]___a___a___a___a___a >
            200                 210                 220                 230                 240
             *                   *                   *                   *                   *
AAG GGC CGA TTC ACC ATC TCC AGA GAC AAC GCC AAG AAC ACG CTG TAT
 K   G   R   F   T   I   S   R   D   N   A   K   N   T   L   Y >
___a___a___a_TRANSLATION OF 1AE-5 VH [A]___a___a___a___a___a___a >
            250                 260                 270                 280
             *                   *                   *                   *
CTG CAA ATG AAC AGT CTG AGA GCC GAG GAC ACG GCC GTG TAT TAC TGT
 L   Q   M   N   S   L   R   A   E   D   T   A   V   Y   Y   C >
___a___a___a_TRANSLATION OF 1AE-5 VH [A]___a___a___a___a___a___a >
            290                 300                 310                 320                 330
             *                   *                   *                   *                   *
GCA AGG GAG AAT AGT TAT GTG CCT TGG GGC CAG GGC ACC CTG GTC ACC
 A   R   E   N   S   Y   V   P   W   G   Q   G   T   L   V   T >
___a___a___a_TRANSLATION OF 1AE-5 VH [A]___a___a___a___a___a___a >
            340
             *
GTC TCC TCA  (SEQ ID NO:113)
 V   S   S>  (SEQ ID NO:111)
___a___a___a >
```

(iii)  <u>1A-116 VH</u>

```
Sequence Range: 1 to 354

10              20              30              40
          *               *               *               *
CAG GTG CAA CTG CAG GAG TCG GGA GGC GTG GTC CAG CCT GGG GGG
 Q   V   Q   L   Q   E   S   G   G   V   V   Q   P   G   G   a_TRANSLATION OF 1AH-6 VH [A]_____a_____a_____a>

50              60              70              80              90
          *               *               *               *               *
TCC CTG AGA CTC TCC TGT GCA GCG TCT GGA TTC ACC TTC AGT GGC TAT
 S   L   R   L   S   C   A   A   S   G   F   T   F   S   G   Y   a_TRANSLATION OF 1AH-6 VH [A]_____a_____a_____a>

100             110             120             130             140
          *               *               *               *               *
GGC ATG CAC TGG GTC CGC CAG GCT CCA GGC AAG GGG CTG GAG TGG GTG
 G   M   H   W   V   R   Q   A   P   G   K   G   L   E   W   V   a_TRANSLATION OF 1AH-6 VH [A]_____a_____a_____a>

150             160             170             180             190
          *               *               *               *               *
GCA TCT GTA CGG AAC GAT GGA AGT AAT ACA TAC TAC TAC ACA GAC TCC GTG
 A   S   V   R   N   D   G   S   N   T   Y   Y   Y   T   D   S   V   a_TRANSLATION OF 1AH-6 VH [A]_____a_____a_____a>

200             210             220             230             240
          *               *               *               *               *
AAG GGC CGA TTC ACC ATC CCC AGA GAC AAC ACC AAG AAC ACG CTG TAT
 K   G   R   F   T   I   P   R   D   N   T   K   N   T   L   Y   a_TRANSLATION OF 1AH-6 VH [A]_____a_____a_____a>

250             260             270             280
          *               *               *               *
CTG CAA ATG AAC AGC CTG AGA GCC GAG GAC ACG GTA TAT TAC TGT
 L   Q   M   N   S   L   R   A   E   D   T   A   V   Y   Y   C
```

```
                                                                              a   a   a TRANSLATION OF 1AH-6 VH [A]   a   a   a   a
    290           300           310           320           330
     *             *             *             *             *
    ACG TCT GAT CCT TTA CGC TAT CCT ATT GAC TAC TGG GGC CAG GGA ACC
     T   S   D   P   L   R   Y   P   I   D   Y   W   G   Q   G   T>
    a   a   a   a TRANSLATION OF 1AH-6 VH [A]   a   a   a   a   a 340           350
           *             *
          CTG GTC ACC GTC TCG AGT   (SEQ ID NO: 114)
           L   V   T   V   S   S>   (SEQ ID NO: 112)
              TRANSLATION OF 1
```

(iv) 31G9 VH

Sequence Range: 1 to 369

```
                 10            20            30            40
                  *             *             *             *
    CAG GTG CAG CTG GTG CAG TCT GGG GGA GGC GTG CAG CCT GGG AGG
     Q   V   Q   L   V   Q   S   G   G   G   V   Q   P   G   R>
    a   a   a   TRANSLATION OF 31G9 VH.SEQ [A] a   a   a   a 50            60            70            80            90
     *             *             *             *             *
    TCC CTG AGA CTC TCC TGT GCA GCC TCT GGA TTC ACC TTC AGT AGC TAT
     S   L   R   L   S   C   A   A   S   G   F   T   F   S   S   Y>
    a   a   a   TRANSLATION OF 31G9 VH.SEQ [A] a   a   a   a   a 100           110           120           130           140
     *             *             *             *             *
    GGC ATG CAC TGG GTC CGC CAG GCT CCA GGC AAG GGG CTG GAG TGG GTG
     G   M   H   W   V   R   Q   A   P   G   K   G   L   E   W   V>
    a   a   a   TRANSLATION OF 31G9 VH.SEQ [A] a   a   a   a   a
```

```
                150            160            170           180            190
         *       *      *       *       *      *      *      *      *       *
         GCA GTT ATA TCA TAT GAT GGA AGT ATT AAA TAC TAT GCA GAC TCC GTG
          A   V   I   S   Y   D   G   S   I   K   Y   Y   A   D   S   V>
    a____a_____TRANSLATION OF 31G9 VH.SEQ [A]_a_____a_____a_____a_____a___>

200            210            220           230            240
       *       *      *       *       *      *      *      *      *       *
       AAG GGC CGA TTC ACC ATC TCC AGA GAC AAT TCC AAG AAC ACG CTG TAT
        K   G   R   F   T   I   S   R   D   N   S   K   N   T   L   Y>
  a____a_____TRANSLATION OF 31G9 VH.SEQ [A]_a_____a_____a_____a_____a___>

250            260            270           280
       *       *      *       *       *      *      *      *      *
       CTG CAA ATG AAC AGC CTG AGA GCT GAG GAC ACG GCT GTG TAT TAC TGT
        L   Q   M   N   S   L   R   A   E   D   T   A   V   Y   Y   C>
  a____a_____TRANSLATION OF 31G9 VH.SEQ [A]_a_____a_____a_____a_____a___>

290           300            310            320           330
       *      *      *      *      *       *      *      *      *       *
       GCG CGA ACT GGT GAA TAT AGT GGC TAC GAT ACG AGT GGT GTG GAG CTC
        A   R   T   G   E   Y   S   G   Y   D   T   S   G   V   E   L>
  a____a_____TRANSLATION OF 31G9 VH.SEQ [A]_a_____a_____a_____a_____a___>

340           350            360
       *      *      *      *      *       *
       TGG GGG CAA GGG ACC ACG GTC ACC GTC TCC TCA (SEQ ID NO:9)
        W   G   Q   G   T   T   V   T   V   S   S>       (SEQ ID NO:10)
  a____a_____TRANSLATION OF 31G9 VH.SEQ [A]
```

(v) 31G9 VL

```
           10              20            30              40
     *      *       *      *      *      *      *       *
     GAC ATC GTG ATG ACC CAG TCT CCT TCC ACC CTG TCT GCA TCT GTA GGA
```

```
        D   I   V   M   T   Q   S   P   S   T   L   S   A   S   V   G>
      __a___a___TRANSLATION OF 31G9 VL.SEQ [A]_a___a___a___a___a___a__^
 50                      60                      70                      80                      90
  *                       *                       *                       *                       *
GAC AGA GTC ACC ATC ACT TGC CGG GCC AGT CAG GGT ATT AGT AGC TGG
 D   R   V   T   I   T   C   R   A   S   Q   G   I   S   S   W>
      __a___a___TRANSLATION OF 31G9 VL.SEQ [A]_a___a___a___a___a___a__^
100                     110                     120                     130                     140
  *                       *                       *                       *                       *
TTG GCC TGG TAT CAG CAG AAA CCA GGG AGA GCC CCT AAG GTC TTG ATC
 L   A   W   Y   Q   Q   K   P   G   R   A   P   K   V   L   I>
      __a___a___TRANSLATION OF 31G9 VL.SEQ [A]_a___a___a___a___a___a__^
150                     160                     170                     180                     190
  *                       *                       *                       *                       *
TAT AAG GCA TCT ACT TTA GAA AGT GGG GTC CCA TCA AGG TTC AGC GGC
 Y   K   A   S   T   L   E   S   G   V   P   S   R   F   S   G>
      __a___a___TRANSLATION OF 31G9 VL.SEQ [A]_a___a___a___a___a___a__^
200                     210                     220                     230                     240
  *                       *                       *                       *                       *
AGT GGA TCT GGG ACA GAT TTC ACT CTC ACC ATC AGC AGT CTG CAA CCT
 S   G   S   G   T   D   F   T   L   T   I   S   S   L   Q   P>
      __a___a___TRANSLATION OF 31G9 VL.SEQ [A]_a___a___a___a___a___a__^
250                     260                     270                     280
  *                       *                       *                       *
GAA GAT TTT GCA ACT TAC TAC TGT CAA CAG AGT TAC AGT ACC CCG TGG
 E   D   F   A   T   Y   Y   C   Q   Q   S   Y   S   T   P   W>
      __a___a___TRANSLATION OF 31G9 VL.SEQ [A]_a___a___a___a___a___a__^
290                     300                     310                     320
  *                       *                       *                       *
ACG TTC GGC CAA GGG ACC AAG CTG GAG ATC AAA CGT    (SEQ ID NO:13)
 T   F   G   Q   G   T   K   L   E   I   K   R     (SEQ ID NO:14)
```

Figure 1 (b) Light chains of antibodies to TGFbeta1 isolated by chain shuffling

FIG. 1(b) (i) 7A3 VL

Sequence Range: 1 to 342

```
                    10             20             30             40
                     *              *              *              *
         GAC ATC GTG ATG ACC CAG TCT CCA GAC TCC CTG GCT GTG TCT CTG GGC
          D   I   V   M   T   Q   S   P   D   S   L   A   V   S   L   G>
    a    a    a    TRANSLATION OF 7A3 VL.SEQ [A]    a    a    a    a    a
    50             60             70             80             90
     *              *              *              *              *
         GAG AGG GCC ACC ATC AAC TGC AAG TCC AGC CAG AGT CTT TTA TAC AGC
          E   R   A   T   I   N   C   K   S   S   Q   S   L   L   Y   S>
    a    a    a    TRANSLATION OF 7A3 VL.SEQ [A]    a    a    a    a    a
    100            110            120            130            140
     *              *              *              *              *
         TAC AAC AAG ATG AAC TAC TTA GCT TGG TAC CAG CAG AAA CCA GGA CAG
          Y   N   K   M   N   Y   L   A   W   Y   Q   Q   K   P   G   Q>
    a    a    a    TRANSLATION OF 7A3 VL.SEQ [A]    a    a    a    a    a
    150            160            170            180            190
     *              *              *              *              *
         CCT CCT AAG CTG CTC ATT AAC TGG GCA TCT ACC CGG GAA TCC GGG GTC
          P   P   K   L   L   I   N   W   A   S   T   R   E   S   G   V>,
    a    a    a    TRANSLATION OF 7A3 VL.SEQ [A]    a    a    a    a    a
    200            210            220            230            240
     *              *              *              *              *
         CCT GAC CGA TTC AGT GGC AGC GGG TCT GGG ACA GAT TTC ACT CTC ACC
          P   D   R   F   S   G   S   G   S   G   T   D   F   T   L   T>
```

```
                                TRANSLATION OF 7A3 VL.SEQ [A]
         250          260          270          280
          *            *            *            *
ATC AGC AGC CTG CAG GCT CAG GAA GAT GTG GCA GTT TAT TAC TGT CAG CAA
 I   S   S   L   Q   A   E   D   V   A   V   Y   Y   C   Q   Q
                                TRANSLATION OF 7A3 VL.SEQ [A]
         290          300          310          320          330
          *            *            *            *            *
TAT TAT GCA ACT CCT CTG ACG TTC GGC CAC GGG ACC AAG GTG GAA ATC
 Y   Y   A   T   P   L   T   F   G   H   G   T   K   V   E   I
                                TRANSLATION OF 7A3 VL.SEQ [A]
         340
          *
AAA CGT   (SEQ ID NO: 15)
 K   R>   (SEQ ID NO:16)
```

FIG. 1(b)(ii) 10A6 VL

Sequence Range: 1 to 357

```
         10           20           30           40
          *            *            *            *
CAC GTT ATA CTG ACT CAG GAC CCT GCT GTG TCT CTG GCC GTG GGA CAG
 H   V   I   L   T   Q   D   P   A   V   S   L   A   V   G   Q
                                TRANSLATION OF 10A6 VL.SEQ [A]
         50           60           70           80           90
          *            *            *            *            *
ACA GTC AGG ATC ACG TGC CAA GGA GAC AGC CTC AAA AGC TAC TAT GCA
 T   V   R   I   T   C   Q   G   D   S   L   K   S   Y   Y   A
                                TRANSLATION OF 10A6 VL.SEQ [A]
        100          110          120          130          140
```

```
                    *         *         *         *         *         *
AGT TGG TAC CAG CAG AAG CCA GGA CAG GCC CCT GTA CTT GTC ATC TAT
 S   W   Y   Q   Q   K   P   G   Q   A   P   V   L   V   I   Y >
___a___a___TRANSLATION OF 10A6 VL.SEQ [A]_a___a___a___a___a___a___ >
     150             160             170       180            190
      *               *               *         *              *

GGT GAA AAC AGC CGG CCC TCC GGG ATC CCA GAC CGA TTC TCT GGC TCC
 G   E   N   S   R   P   S   G   I   P   D   R   F   S   G   S >
___a___a___TRANSLATION OF 10A6 VL.SEQ [A]_a___a___a___a___a___a___ >
     200             210             220            230       240
      *               *               *              *         *

AGC TCA GGA AAC ACA GCT TCC TTG ACC ATC ACT GGG GCT CAG GCG GAA
 S   S   G   N   T   A   S   L   T   I   T   G   A   Q   A   E >
___a___a___TRANSLATION OF 10A6 VL.SEQ [A]_a___a___a___a___a___a___ >
          250             260             270       280
           *               *               *         *

GAT GAA GCT GAT TAT TAC TGT AAC TCC CGG GAC AGC AGT GGT ACC CAT
 D   E   A   D   Y   Y   C   N   S   R   D   S   S   G   T   H >
___a___a___TRANSLATION OF 10A6 VL.SEQ [A]_a___a___a___a___a___a___ >
 290             300             310             320
  *               *               *               *

CTA GAA GTG TTC GGC GGA GGG ACC AAG CTG ACC GTC CTA GGT (SEQ ID NO:17)
 L   E   V   F   G   G   G   T   K   L   T   V   L   G    (SEQ ID NO:18)
___a___a___TRANSLATION OF 10A6 VL.SEQ [A]_a___a___a___a___ >
      *         *         *         *
```

Figure 1 (c) Antibodies to TGFbeta1 isolated from CDR3 spiking experiment

FIG. 1(c) (i) 27C1 VH

Sequence Range: 1 to 369

10        20        30        40

```
        *         *         *         *         *         *         *
CAG GTG CAA CTG GTG GAG TCT GGG GGA GGC GTG CAG CCT GGG AGG
 Q   V   Q   L   V   E   S   G   G   G   V   Q   P   G   R>    TRANSLATION OF 27C1 VH.SEQ [A]
    a   a   a   a   a   a   a   a   a   a   a   a   a   a   a
         *         *         *         *         *
        50        60        70        80        90
         *         *         *         *         *
TCC CTG AGA CTC TCC TGT GCA GCC TCT GGA TTC ACC TTC AGT AGC TAT
 S   L   R   L   S   C   A   A   S   G   F   T   F   S   S   Y>    TRANSLATION OF 27C1 VH.SEQ [A]
    a   a   a   a   a   a   a   a   a   a   a   a   a   a   a
         *         *         *         *         *
        100       110       120       130       140
         *         *         *         *         *
GAC ATG CAC TGG GTC CGC CAG CCT CCA GCC AAG GGG CTG GAG TGG GTG
 D   M   H   W   V   R   Q   P   P   A   K   G   L   E   W   V>    TRANSLATION OF 27C1 VH.SEQ [A]
    a   a   a   a   a   a   a   a   a   a   a   a   a   a   a
         *         *         *         *         *
        150       160       170       180       190
         *         *         *         *         *
GCA GTT ATA TCA TAT GAT GGA AGT AGT AAA TAC TAT GCA GAC TCC GTG
 A   V   I   S   Y   D   G   S   S   K   Y   Y   A   D   S   V>    TRANSLATION OF 27C1 VH.SEQ [A]
    a   a   a   a   a   a   a   a   a   a   a   a   a   a   a
         *         *         *         *         *
        200       210       220       230       240
         *         *         *         *         *
AAG GGC CGA TTC ACC ATC TCC AGA GAC AAT TCC AAG AAC ACG CTG TAT
 K   G   R   F   T   I   S   R   D   N   S   K   N   T   L   Y>    TRANSLATION OF 27C1 VH.SEQ [A]
    a   a   a   a   a   a   a   a   a   a   a   a   a   a   a
         *         *         *         *         *
        250       260       270       280
         *         *         *         *
CTG CAA ATG AAC AGC CTG AGA GCT GAG GAC ACG GCT GTG TAT TAC TGT
 L   Q   M   N   S   L   R   A   E   D   T   A   V   Y   Y   C>    TRANSLATION OF 27C1 VH.SEQ [A]
    a   a   a   a   a   a   a   a   a   a   a   a   a   a   a
         *         *         *         *
        290       300       310       320       330
         *         *         *         *         *
```

```
GCG CGA ACT GGT GAA TAT AGT GGC TAC GAC ACG AGT GGT GTG GAG CTC
 A   R   T   G   E   Y   S   G   Y   D   T   S   G   V   E   L  >
_a_____a_____a_____TRANSLATION OF 27C1 VH.SEQ [A]_a_____a_____a_____a_____a___>

340                  350                  360
    *                    *                    *
TGG GGG CAA GGG ACC ACG GTC ACC GTC TCC TCA                    (SEQ ID NO:11)
 W   G   Q   G   T   T   V   T   V   S   S  >                 (SEQ ID NO:12)
_a_____TRANSLATION OF 27C1 VH.SEQ [A]_____a___>
```

Figure 2 Sequences of antibodies specific for TGFbeta2

(a) Antibodies to TGFbeta 2 isolated directly from repertoires

FIG 2.(a) (i) 2A-H11 VH (also known as 6H1 VH)

Sequence Range: 1 to 345

```
              10         20         30         40
               *          *          *          *
     GAG GTG CAG CTG GTG GAG TCT GGG GGA GGC GTG CAG CCT GGG AGG
      E   V   Q   L   V   E   S   G   G   G   V   Q   P   G   R>
     _a___a___a___TRANSLATION OF 6H1 VH.SEQ [A]_a___a___a___a__^

50         60         70         80         90
       *          *          *          *          *
     TCC CTG AGA CTC TCC TGT GCA GCG TCT GGA TTC ACC TTC AGT AGC TAT
      S   L   R   L   S   C   A   A   S   G   F   T   F   S   S   Y>
     _a___a___a___TRANSLATION OF 6H1 VH.SEQ [A]_a___a___a___a__^

100        110        120        130        140
      *          *          *          *          *
     GGC ATG CAC TGG GTC CGC CAG GCT CCA GGC AAG GGG CTG GAG TGG GTG
      G   M   H   W   V   R   Q   A   P   G   K   G   L   E   W   V>
     _a___a___a___TRANSLATION OF 6H1 VH.SEQ [A]_a___a___a___a__^

150        160        170        180        190
      *          *          *          *          *
     GCA GTT ATA TGG TAT GAT GGA AGT AAT AAA TAC TAT GCA GAC TCC GTG
      A   V   I   W   Y   D   G   S   N   K   Y   Y   A   D   S   V>
     _a___a___a___TRANSLATION OF 6H1 VH.SEQ [A]_a___a___a___a__^

200        210        220        230        240
      *          *          *          *          *
     AAG GGC CGA TTC ACC ATC TCC AGA GAC AAT TCC AAG AAC ACG CTG TAT
      K   G   R   F   T   I   S   R   D   N   S   K   N   T   L   Y>
     _a___a___a___TRANSLATION OF 6H1 VH.SEQ [A]_a___a___a___a__^
```

```
                         250                 260                 270                 280
                          *                   *                   *                   *
CTG CAA ATG GAC AGC CTG AGA GCC GAG GAC ACG GCC GTG TAT TAC TGT
 L   Q   M   D   S   L   R   A   E   D   T   A   V   Y   Y   C    TRANSLATION OF 6H1 VH.SEQ [A]_a__a__a__a__a__a__a__a__a__a__a__a__a__a__a__a>

290                 300                 310                 320                 330
          *                   *                   *                   *                   *
GGA AGA ACG GAG CTG GAG TCT AGT TTG TGG GGC CAA GGC ACC CTG GTC ACC
 G   R   T   E   L   E   S   S   L   W   G   Q   G   T   L   V   T    TRANSLATION OF 6H1 VH.SEQ [A]_a__a__a__a__a__a__a__a__a__a__a__a__a__a__a__a__a>

340
          *
GTC TCC TCA    (SEQ ID NO:5)
 V   S   S>    (SEQ ID NO:6)
_a__a__a>

FIG 2.(a)(ii) 2A-A9 (also known as 11E6 VH)

Sequence Range: 1 to 350

10                  20                  30                  40
                           *                   *                   *                   *
GAG ATT CAG CTG GTG GAG TCT GGG GGA GGC GTG GTC CAG CCT GGG AGA
 E   I   Q   L   V   E   S   G   G   G   V   V   Q   P   G   R    TRANSLATION OF 11E6 VH.SEQ [A]_a__a__a__a__a__a__a__a__a__a__a__a__a__a__a__a>

50                  60                  70                  80                  90
           *                   *                   *                   *                   *
TCC CTG AGA CTC TCC TGT GCA GCC TCT GGA TTC ACC TTC AGT AGC TAT
 S   L   R   L   S   C   A   A   S   G   F   T   F   S   S   Y    TRANSLATION OF 11E6 VH.SEQ [A]_a__a__a__a__a__a__a__a__a__a__a__a__a__a__a__a__a>

100                 110                 120                 130                 140
          *                   *                   *                   *                   *
```

```
GCT ATG CAC TGG GTC CGC CAG GCT CCA GCC AAG GGG CTG GAG TGG GTG
 A   M   H   W   V   R   Q   A   P   A   K   G   L   E   W   V  >
         a       a       TRANSLATION OF 11E6 VH.SEQ [A]_a___a___a___a___a___^
     *       150       *       160       *       170       *       180       *       190

GCA GTT ATA TCA TAT GAT GGA AGC AAT AAA TAC TAC GCA GAC TCC GTG
 A   V   I   S   Y   D   G   S   N   K   Y   Y   A   D   S   V  >
___a___a       TRANSLATION OF 11E6 VH.SEQ [A]_a___a___a___a___a___^
         *       200       *       210       *       220       *       230       *       240

AAG GGC CGA TTC ACC ATC TCC AGA GAC AAT TCC AAG AAC ACG CTG TAT
 K   G   R   F   T   I   S   R   D   N   S   K   N   T   L   Y  >
___a___a       TRANSLATION OF 11E6 VH.SEQ [A]_a___a___a___a___a___^
         *       250       *       260       *       270       *       280

CTG CAA ATG AAC AGC CTG AGA GCT GAG GAC ACG GCC GTG TAT TAC TGT
 L   Q   M   N   S   L   R   A   E   D   T   A   V   Y   Y   C  >
___a___a       TRANSLATION OF 11E6 VH.SEQ [A]_a___a___a___a___a___^
     *       290       *       300       *       310       *       320       *       330

GCA AGA GCG GGG TTG GAA ACG TGG GGC CAA GGA ACC CTG GTC ACC
 A   R   A   G   L   E   T   W   G   Q   G   T   L   V   T  >
___a___a       TRANSLATION OF 11E6 VH.SEQ [A]_a___a___a___a___a___^
         *       340       *       350

GTC TCC TCA AGT GG        (SEQ ID NO:36)
 V   S   S   S   G  >     (SEQ ID NO:37)
         TRANSLATION_a___^
```

FIG 2.(a)(iii) Gold11-VH

Sequence Range: 1 to 369

```
         10         20         30         40
          *          *          *          *
CAG GTC ACC TTG AAG GAG TCT GGG GGA AGC GTG GTC CAG CCT GGG AGG
 Q   V   T   L   K   E   S   G   G   S   V   V   Q   P   G   R>
 a___a___a___a_TRANSLATION OF GOLD11-VH [A]___a___a___a___a___^

50         60         70         80         90
  *          *          *          *          *
TCC CTG AGA CTC TCC TGT GCA GCC TCT GGA TTC ACC TTC AGT AGC TAT
 S   L   R   L   S   C   A   A   S   G   F   T   F   S   S   Y>
 a___a___a___a_TRANSLATION OF GOLD11-VH [A]___a___a___a___a___^

100        110        120        130        140
  *          *          *          *          *
GGC ATG CAC TGG GTC CGC CAG GCT CCA GGC AAG GGG CTG GAG TGG GTG
 G   M   H   W   V   R   Q   A   P   G   K   G   L   E   W   V>
 a___a___a___a_TRANSLATION OF GOLD11-VH [A]___a___a___a___a___^

150        160        170        180        190
  *          *          *          *          *
GCA GTT ATA TCA TAT GAT GGA AGT AAT AAA TAC TAT GCA GAC TCC GTG
 A   V   I   S   Y   D   G   S   N   K   Y   Y   A   D   S   V>
 a___a___a___a_TRANSLATION OF GOLD11-VH [A]___a___a___a___a___^

200        210        220        230        240
  *          *          *          *          *
AAG GGC CGA TTC ACC ATC TCC AGA GAC AAT TCC AAG AAC ACG CAG TAT
 K   G   R   F   T   I   S   R   D   N   S   K   N   T   Q   Y>
 a___a___a___a_TRANSLATION OF GOLD11-VH [A]___a___a___a___a___^

250        260        270        280
  *          *          *          *
```

```
                                                                                    CTG CAA ATG AAC AGC CTG AGA GCT GAA GAC ACG GCA GAG TAT TAC TGT
                                                                                     L   Q   M   N   S   L   R   A   E   D   T   A   E   Y   Y   C>
                                                                                    _a__a__a__a_TRANSLATION OF GOLD11-VH [A]__a__a__a__a__a__a_>

290              300              310              320              330
 *                *                *                *                *
GCG AGA ACT GGG GAA TAT AGT GGC CAC GCA TCT ACT GGA GAG AAC GTC
 A   R   T   G   E   Y   S   G   H   A   S   T   G   E   N   V>
_a__a__a_TRANSLATION OF GOLD11-VH [A]__a__a__a__a__a__a_>

340              350              360
 *                *                *
TGG GGC CGG GGC ACC CTG GTC ACC GTC TCG AGT           (SEQ ID NO:115)
 W   G   R   G   T   L   V   T   V   S   S>          (SEQ ID NO:116)
_a__TRANSLATION OF GOLD11-VH [A]__a__a_>
```

FIG 2.(a)(iv) <u>Gold11-VL</u>

Sequence Range: 1 to 336

```
                 10               20               30               40
 *                *                *                *                *
TCC TAT GTG CTG ACT CAC CCC CCC TCA GTG TCT GGG ACC CCC GGG CAG
 S   Y   V   L   T   H   P   P   S   V   S   G   T   P   G   Q>
_a__a__a_TRANSLATION OF GOLD11-VL [A]__a__a__a__a__a__a_>

50               60               70               80               90
 *                *                *                *                *
AGA GTC ACC ATC TCT TGT TCT GGA AGC AGA TCC AAC ATC GGC AGT AAT
 R   V   T   I   S   C   S   G   R   S   N   I   G   S   N>
_a__a__a_TRANSLATION OF GOLD11-VL [A]__a__a__a__a__a__a_>

100              110              120              130              140
 *                *                *                *                *
ACT GTA AAG TGG TAT CAG CAG CTC CCA GGA ACG CCC CCC AAA CTC CTC
 T   V   K   W   Y   Q   Q   L   P   G   T   P   P   K   L   L>
```

FIG 2.(a)(v)
1-G2

```
                  150               160               170               180               190
         *         *         *         *         *         *         *         *         *
                                      ATC TAT GGC AAT GAT CAG CGG CCC TCA GGG ATC CCT GAC CGA TTC TCT
                                       I   Y   G   N   D   Q   R   P   S   G   I   P   D   R   F   S  >
    _a____a____a____a__TRANSLATION OF GOLD11-VL [A]_a____a____a____a____a____a____a____a____a____a____a__

200               210               220               230               240
         *         *         *         *         *         *         *         *         *
         GGC TCC AAG TCT GGC ACC TCA GCC TCC CTG GCC ATC ACT GGG GTC CAG
         G   S   K   S   G   T   S   A   S   L   A   I   T   G   V   Q  >
    _a____a____a____a__TRANSLATION OF GOLD11-VL [A]_a____a____a____a____a____a____a____a____a____a__

250               260               270               280
         *         *         *         *         *         *         *         *
         GCT GAA GAC GAG GCT GAC TAT TAC TGC CAG TCA TAT GAC AGC AGC CTG
         A   E   D   E   A   D   Y   Y   C   Q   S   Y   D   S   S   L  >
    _a____a____a____a__TRANSLATION OF GOLD11-VL [A]_a____a____a____a____a____a____a____a____a____a__

290               300               310               320               330
         *         *         *         *         *         *         *         *         *
         AGG GGT TCG AGG GTC TTC GGA ACT GGG ACC AAG GTC ACC GTC CTA GGT   (SEQ ID NO:117)
         R   G   S   R   V   F   G   T   G   T   K   V   T   V   L   G  > (SEQ ID NO:118)
    _a____a____a____a__TRANSLATION OF GOLD11-VL [A]_a____a____a____a____a____a____a____a____a____a__

Sequence Range: 1 to 381
                  10                20                30                40
         *         *         *         *         *         *         *         *         *
         CAG GTA CAA CCT CAG CAG CAG TCT GGG GGA GAG GTG AAG CAG CCT GGG GCC
         Q   V   Q   P   Q   Q   Q   S   G   G   E   V   K   Q   P   G   A  >
    _a____a____a____a__TRANSLATION OF 1-G2-VII [A]_a____a____a____a____a____a____a____a____a____a____a__
                  50                60                70                80                90
```

```
                    *          *          *          *          *          *          *
          TCC GTG AAG GTT TCC TGT AAG GCG TCT GGA TAC ACC TTC ACC AGC TTC
           S   V   K   V   S   C   K   A   S   G   Y   T   F   T   S   F>
         a__a__a_ TRANSLATION OF 1-G2-VH [A]__a__a__a__a__a__a__a__a__a__a__
            *          *          *          *          *          *
           100        110        120        130        140
            *          *          *          *          *          *
          TAT ATG AAC TGG GTG CGA CAG GCC CCC GGA CAA GGG CTT GAG TGG ATG
           Y   M   N   W   V   R   Q   A   P   G   Q   G   L   E   W   M>
         a__a__a_ TRANSLATION OF 1-G2-VH [A]__a__a__a__a__a__a__a__a__a__a__
            *          *          *          *          *          *
           150        160        170        180        190
            *          *          *          *          *          *
          GGA ATA ATC AGC CCT CGT GGT ACG ACA AGT TAC GCA CAG AAC TTC
           G   I   I   S   P   R   G   T   T   S   Y   A   Q   N   F>
         a__a__a_ TRANSLATION OF 1-G2-VH [A]__a__a__a__a__a__a__a__a__a__a__
            *          *          *          *          *          *
           200        210        220        230        240
            *          *          *          *          *          *
          CAG GGC AGA GTC ACC ATG ACC AGG GAC ACG TCC ACA AGC ACA GTC TAC
           Q   G   R   V   T   M   T   R   D   T   S   T   S   T   V   Y>
         a__a__a_ TRANSLATION OF 1-G2-VH [A]__a__a__a__a__a__a__a__a__a__a__
            *          *          *          *          *          *
           250        260        270        280
            *          *          *          *          *          *
          ATG GAG CTG AGC AGC CTG AGA TCT GAG GAC ACG GCC GTG TAT TAT TGT
           M   E   L   S   S   L   R   S   E   D   T   A   V   Y   Y   C>
         a__a__a_ TRANSLATION OF 1-G2-VH [A]__a__a__a__a__a__a__a__a__a__a__
            *          *          *          *          *          *
           290        300        310        320        330
            *          *          *          *          *          *
          GCG ATA ATT GGG GGT ACT ACT ATG AGA GTA GGG GGG CCC GAT GCT TTT
           A   I   I   G   G   T   T   M   R   V   G   G   P   D   A   F>
         a__a__a_ TRANSLATION OF 1-G2-VH [A]__a__a__a__a__a__a__a__a__a__a__
            *          *          *          *          *
           340        350        360        370        380
```

FIG 2.(a)(vi)
1-H6

Sequence Range: 1 to 381

```
                                                                                                        (SEQ ID NO:119)
GAT ATC TGG GGC CAA GGG ACA ATG GTC ACC GTC TCT TCA                                                     (SEQ ID NO:120)
 D   I   W   G   Q   G   T   M   V   T   V   S   S  >
 a___a___a__TRANSLATION OF 1-G2-VH [A]_a___a___a___a_____>

10                  20                  30                  40
           *                   *                   *                   *
GAG GTG CAG CTG GTG GAG TCT GGG GGA GGC GTG GTC CAG CCT GGG AGG
 E   V   Q   L   V   E   S   G   G   G   V   V   Q   P   G   R  >
 a___a___a__TRANSLATION OF 1-H6 VH [A]_a___a___a___a_____>

50                  60                  70                  80                  90
           *                   *                   *                   *                   *
TCC CTG AGA CTC TCC TGT GCA GCG TCT GGA TTC ACC TTC AGG AAC TAT
 S   L   R   L   S   C   A   A   S   G   F   T   F   R   N   Y  >
 a___a___a__TRANSLATION OF 1-I16 VH [A]_a___a___a___a_____>

100                 110                 120                 130                 140
           *                   *                   *                   *                   *
GGC ATG CAC TGG GTC CGC CAG GCT CCA GGC AAG GGG CTG GAG TGG GTG
 G   M   H   W   V   R   Q   A   P   G   K   G   L   E   W   V  >
 a___a___a__TRANSLATION OF 1-I16 VH [A]_a___a___a___a_____>

150                 160                 170                 180                 190
           *                   *                   *                   *                   *
GCA GTT ATA TGG TAT GAT GGA AGT AAT AAA TAC TAT GCA GAC TCC GTG
 A   V   I   W   Y   D   G   S   N   K   Y   Y   A   D   S   V  >
 a___a___a__TRANSLATION OF 1-I16 VH [A]_a___a___a___a_____>

200                 210                 220                 230                 240
           *                   *                   *                   *                   *
AAG GGC CGA TTC ACC ATC TCC AGA GAC AAT TCC AAG AAC ACG CTG TAT
```

```
        K   G   R   F   T   I   S   R   D   N   S   K   N   T   L   Y >
      __a___a___a___ TRANSLATION OF 1-H6 VH [A] __a___a___a___a___a__ >
            *       250       *       260       *       270       *       280       *
      CTG CAA ATG AAC AGC CTG AGA GTC GAG GAC ACG GCT GTT TAT TAC TGT
        L   Q   M   N   S   L   R   V   E   D   T   A   V   Y   Y   C >
      __a___a___a___ TRANSLATION OF 1-H6 VH [A] __a___a___a___a___a__ >
290       *       300       *       310       *       320       *
      GCG AGA AGA TGG TAT GGT GGC AGT GGT TAT TGG GGC CAC TTC TAC TCC
        A   R   R   W   Y   G   G   S   G   Y   W   G   H   F   Y   S >
      __a___a___a___ TRANSLATION OF 1-H6 VH [A] __a___a___a___a___a__ >
      340       *       350       *       360       *       370       *       380
      TAC ATG GAC GGC TGG GGC AAA GGG ACC AAG GTC ACC GTC TCC TCA  (SEQ ID NO:121)
        Y   M   D   G   W   G   K   G   T   K   V   T   V   S   S >    (SEQ ID NO:122)
      __a___a___a___ TRANSLATION OF 1-H6 VH [A] __a___a___a___a__ >
```

Figure 2(b)(i)

```
          10             20                  30              40
GAT GTT GTG ATG ACT CAG TCT CCA TCC CTG TCT GCA TCT GTA GGA
 D   V   V   M   T   Q   S   P   S   L   S   A   S   V   G>

50             60              70              80              90
GAC AGA GTC ACC ATC ACT TGC CGG GCC AGT CAG GGC ATT AGC AAT TAT
 D   R   V   T   I   T   C   R   A   S   Q   G   I   S   N   Y>

100            110            120            130            140
TTA GCC TGG TAT CAG CAA AAA CCA GGG AAA GCC CCT AAG CTC CTG ATC
 L   A   W   Y   Q   Q   K   P   G   K   A   P   K   L   L   I>

150            160            170            180            190
TAT AAG GCA TCT ACT TTA GAA AGT GGG GTC CCA TCA AGG TTC AGT GGC
 Y   K   A   S   T   L   E   S   G   V   P   S   R   F   S   G>

200            210            220            230            240
AGT GGA TCT GGG ACA GAA TTC ACT CTC ACA ATC AGC AGC CTG CAA CCT
 S   G   S   G   T   E   F   T   L   T   I   S   S   L   Q   P>

250            260            270            280
GAA GAT TTT GCA ACT TAC TAC TGT CAA CAG AGT TAC AGT ACC CCT CGA
 E   D   F   A   T   Y   Y   C   Q   Q   S   Y   S   T   P   R>

290            300            310            320            330
ACG TTC GGC CAA GGG ACC AAA GTG GAT ATC AAA CGT    (SEQ ID NO:38)
 T   F   G   Q   G   T   K   V   D   I   K   R     (SEQ ID NO:39)
```

Figure 2(b)(ii)

```
                       10                  20                  30                    40
TCG TCT GAG CTG ACT CAG GAC CCT GCT GTG TCT GTG GCC TTG GGA CAG
 S   S   E   L   T   Q   D   P   A   V   S   V   A   L   G   Q
 50                  60                  70                  80                    90
ACA GTC AGG ATC ACA TGC CAA GGA GAC AGC CTC AGA AGC TAT TAT GCA
 T   V   R   I   T   C   Q   G   D   S   L   R   S   Y   Y   A
100                 110                 120                 130                   140
AGC TGG TAC CAG CAG AAG CCA GGA CAG GCC CCT GTA CTT GTC ATC TAT
 S   W   Y   Q   Q   K   P   G   Q   A   P   V   L   V   I   Y
150                 160                 170                 180                   190
GGT AAA AAC AAC CGG CCC TCA GGG ATC CCA GAC CGA TTC GCT GGC TCC
 G   K   N   N   R   P   S   G   I   P   D   R   F   A   G   S
200                 210                 220                 230                   240
AAC TCA GGA AAC ACA GCT TCC TTG ACC ATC ACT GGG GCT CAG GCG GAG
 N   S   G   N   T   A   S   L   T   I   T   G   A   Q   A   E
250                 260                 270                 280
GAT GAG GCT GAC TAT TAC TGT AGC TCC CGG GAC AGC AGT GGT AAC CAT
 D   E   A   D   Y   Y   C   S   S   R   D   S   S   G   N   H
290                 300                 310                 320
GTG GTT TTC GGC GGA GGG ACC AAG CTG ACC GTC CTA GGT    (SEQ ID NO:40)
 V   V   F   G   G   G   T   K   L   T   V   L   G>   (SEQ ID NO:41)
```

Figure 2(b)(iii)

```
         10                  20                  30                40
TCG TCT GAG CTG ACT CAG GAC CCT GCT GTG TCT GTG GCC TTG GGA CAG
 S   S   E   L   T   Q   D   P   A   V   S   V   A   L   G   Q 50              60                  70                  80                  90
ACA GTC AGG ATC ACA TGC CAA GGA GAC AGC CTC AGA AGC TAT TAT GCA
 T   V   R   I   T   C   Q   G   D   S   L   R   S   Y   Y   A 100             110                 120                 130             140
AGC TGG TAC CAG CAG AAG CCA GGA CAG GCC CCT GTA CTT GTC ATC TAT
 S   W   Y   Q   Q   K   P   G   Q   A   P   V   L   V   I   Y 150                 160                 170                 180         190
GGT AAA AAC AAC CGG CCC TCA GGG ATC CCA GAC CGA TTC TCT GGC TCC
 G   K   N   N   R   P   S   G   I   P   D   R   F   S   G   S 200                 210                 220                 230             240
AGC TCA GGA AAC ACA GCT TCC TTG ACC ATC ACT GGG GCT CAG GCG GAA
 S   S   G   N   T   A   S   L   T   I   T   G   A   Q   A   E 250                 260                 270                 280
GAT GAG GCT GAC TAT TAC TGT AAC TCC CGG GAC AGC AGT AGT ACC CAT
 D   E   A   D   Y   Y   C   N   S   R   D   S   S   S   T   H 290             300                 310                 320             330
CGA GGG GTG TTC GGC GGA GGG ACC AAG CTG ACC GTC CTA GGT           (SEQ ID NO:42)
 R   G   V   F   G   G   G   T   K   L   T   V   L   G           (SEQ ID NO:43)
```

Figure 2(b)(iv)

```
          10              20              30              40
GAA GTT GTG CTG ACT CAG TCT CCA TCC CTG TCT GCA TCT GTA GGA
 E   V   V   L   T   Q   S   P   S   L   S   A   S   V   G >
50              60              70              80              90
GAC AGA GTC ACC ATC ACT TGC CGG GCA AGT CAG GGC ATT GGA GAT GAT
 D   R   V   T   I   T   C   R   A   S   Q   G   I   G   D   D >
100             110             120             130             140
TTG GGC TGG TAT CAG CAG AAG CCA GGG AAA GCC CCT ATC CTC CTG ATC
 L   G   W   Y   Q   Q   K   P   G   K   A   P   I   L   L   I >
150             160             170             180             190
TAT GGT ACA TCC ACT TTA CAA AGT GGG GTC CCG TCA AGG TTC AGC GGC
 Y   G   T   S   T   L   Q   S   G   V   P   S   R   F   S   G >
200             210             220             230             240
AGT GGA TCT GGG ACA GAT TTC ACT CTC ACC ATC AAC AGC CTG CAG CCT
 S   G   S   G   T   D   F   T   L   T   I   N   S   L   Q   P >
250             260             270             280
GAA GAT TTT GCA ACT TAT TAC TGT CTA CAA GAT TCC AAT TAC CCG CTC
 E   D   F   A   T   Y   Y   C   L   Q   D   S   N   Y   P   L >
290             300             310             320
ACT TTC GGC GGA GGG ACA CGA CTG GAG ATT AAA CGT  (SEQ ID NO:44)
 T   F   G   G   G   T   R   L   E   I   K   R   (SEQ ID NO:45)
```

Figure 2(b)(v)

```
         10                  20                  30                  40
TCG TCT GAG CTG ACT CAG GAC CCT GCT GTG TCT GTG GCC TTG GGA CAG
 S   S   E   L   T   Q   D   P   A   V   S   V   A   L   G   Q>

50                  60                  70                  80                  90
ACA GTC AGG ATC ACA TGC CAA GGA GAC AGC CTC AGA AAC TAT TAT GCA
 T   V   R   I   T   C   Q   G   D   S   L   R   N   Y   Y   A>

100                 110                 120                 130                 140
AAC TGG TAC CAG CAG AAG CCA GGA CAG GCC CCT GTA CTT GTC ATC TAT
 N   W   Y   Q   Q   K   P   G   Q   A   P   V   L   V   I   Y>

150                 160                 170                 180                 190
GGT AAA AAC AAC CGG CCC TCA GGG ATC CCA GAC CGA TTC TCT GGC TCC
 G   K   N   N   R   P   S   G   I   P   D   R   F   S   G   S>

200                 210                 220                 230                 240
AGC TCA GGG AAC ACA GCT TCC TTG ACC ATC ACT GGG GCT CGG GCG GAA
 S   S   G   N   T   A   S   L   T   I   T   G   A   R   A   E>

250                 260                 270                 280
GAT GAG GGT GTC TAT TAC TGT AAC TCC CGG GAC AGC AGT GGT GCG GTT
 D   E   G   V   Y   Y   C   N   S   R   D   S   S   G   A   V>

290                 300                 310                 320
TTC GGC GGA GGG ACC AAG CTG ACC GTC CTA GGT              (SEQ ID NO:46)
 F   G   G   G   T   K   L   T   V   L   G              (SEQ ID NO:47)
```

Sequence Range: 1 to 324

```
                10               20               30               40
                 *                *                *                *
        GAA GTT GTG CTG ACT CAG TCT CCA TCC CTG TCT GCA TCT GTA GGA
         E   V   V   L   T   Q   S   P   S   L   S   A   S   V   G>
    _a___a___a___TRANSLATION OF 11E6 VL.SEQ [A]_a___a___a___a___a___>

50               60               70               80               90
         *                *                *                *                *
        GAC AGA GTC ACC ATC ACT TGC CGG GCA AGT CAG GGC ATT GGA GAT GAT
         D   R   V   T   I   T   C   R   A   S   Q   G   I   G   D   D>
    _a___a___a___TRANSLATION OF 11E6 VL.SEQ [A]_a___a___a___a___a___>

100              110              120              130              140
         *                *                *                *                *
        TTG GGC TGG TAT CAG CAG AAG CCA GGG AAA GCC CCT ATC CTC CTG ATC
         L   G   W   Y   Q   Q   K   P   G   K   A   P   I   L   L   I>
    _a___a___a___TRANSLATION OF 11E6 VL.SEQ [A]_a___a___a___a___a___>

150              160              170              180              190
         *                *                *                *                *
        TAT GGT ACA TCC ACT TTA CAA AGT GGG GTC CCG TCA AGG TTC AGC GGC
         Y   G   T   S   T   L   Q   S   G   V   P   S   R   F   S   G>
    _a___a___a___TRANSLATION OF 11E6 VL.SEQ [A]_a___a___a___a___a___>

200              210              220              230              240
         *                *                *                *                *
        AGT GGA TCT GGA ACA GAT TTC ACT CTC ACC ATC AAC AGC CTG CAG CCT
         S   G   S   G   T   D   F   T   L   T   I   N   S   L   Q   P>
    _a___a___a___TRANSLATION OF 11E6 VL.SEQ [A]_a___a___a___a___a___>

250              260              270              280
         *                *                *                *
        GAA GAT TTT GCA ACT TAT TAC TGT CTA CAA GAT TCC AAT TAC CCG CTC
         E   D   F   A   T   Y   Y   C   L   Q   D   S   N   Y   P   L>
    _a___a___a___TRANSLATION OF 11E6 VL.SEQ [A]_a___a___a___a___a___>

290              300              310              320
         *                *                *                *
        ACT TTC GGC GGA GGG ACA CGA CTG GAG ATT AAA CGT        (SEQ ID NO:123)
         T   F   G   G   G   T   R   L   E   I   K   R>       (SEQ ID NO:124)
    _a___TRANSLATION OF 11E6 VL.SEQ [A]_a___a___>
```

(SEQ ID NOS: 19-35)

| | |
|---|---|
| PARENT (1-B2) | A R T G E Y S G Y D S S G V D V W |
| 27-C1 | A R T G E Y S G Y D T S G V E L W |
| 27-D7 | A R T R E Y S G H D S S G V D D W |
| 27-E10 | A R T G P F S G Y D S S G E D V R |
| 27-H1 | A R T E E Y S G Y D S S G V D V W |
| 27-E2 | A Q T R E Y T G Y D S S G V D V W |
| 28-A11 | A R T E E Y S G F D S T G E D V W |
| 28-E12 | A R T E E F S G Y D S S G V D V W |
| 28-H10 | A R T G E Y S G Y H S S G V D V R |
| 31-G2 | A R T E E F S G Y D S S G V D V W |
| 30-B6 | A R A G P F S G Y D S S G E D V R |
| 30-E9 | A R T G P F S G Y D S S G E D V W |
| 30-F6 | A R T E E F S G Y D S S G V D V W |
| 30-D2 | A R T G E Y S G Y D S S G E L V W |
| 31-A2 | A R T E E F S G Y D S T G E E V W |
| 31-E11 | A R T E E F S G Y D S S G V D V W |
| 31-F1 | A R T G E Y S G Y D S S G E D V W |

```
         10               20               30               40
TCG TCT GAG CTG ACT CAG GAC CCT GCT GTG TCT GTG GCC TTG GGA CAG
 S   S   E   L   T   Q   D   P   A   V   S   V   A   L   G   Q 50               60               70               80               90
ACA GTT AGG ATC ACT TCC CAA GGA GAC AGT ATC CTC AGA AGC TAT TAC ACA
 T   V   R   I   T   S   Q   G   D   S   I   L   R   S   Y   Y 100              110              120              130              140
AAC TGG TTT CAG CAG AAG CCA GGA CAG CCC CCT CTA CTT GTC GTC TAT
 N   W   F   Q   Q   K   P   G   Q   P   P   L   L   V   V   Y 150              160              170              180              190
GCT AAA AAT AAG CGG CCC TCA GGG ATC CCA GAC CGA TTC TCT GGC TCC
 A   K   N   K   R   P   S   G   I   P   D   R   F   S   G   S 200              210              220              230              240
AGC TCA GGA AAC ACA GCT TCC TTG ACC ATC ACT GGG GCT CAG GCG GAA
 S   S   G   N   T   A   S   L   T   I   T   G   A   Q   A   E 250              260              270              280
GAT GAG GCT GAC TAT TAC TGT CAT TCC CGG GAC AGC AGT AAC CAT
 D   E   A   D   Y   Y   C   H   S   R   D   S   S   N   H 290              300              310              320
GTG CTT TTC GGC GGA GGG ACC AAG CTG ACC GTC CTA GGT  (SEQ ID NO:48)
 V   L   F   G   G   G   T   K   L   T   V   L   G   (SEQ ID NO:49)
```

(SEQ ID NOS: 50-52)

```
              H
              i
              n
              d
              I
              I
              I   (SEQ ID NO:50) ---
        aagcttgccgccaccatggactggacctggcgcgtgttttgcctgctcgccgtggcccct
   1    ---------+---------+---------+---------+---------+---------+  60
        ttcgaacggcggtggtacctgacctggaccgcgcacaaaacggacgagcggcaccgggga a         K   L   A   A   T   M   D   W   T   W   R   V   F   C   L   L   A   V   A   P   -
                 (SEQ ID NO:51)---
                                                                B
                                                                s
              S                              P                  t
              f                              s                  E
              i                              t                  I
              I                              I                  I
        ggggcccacagccaggtgcaactgcagcagtccggtgccaagggaccacggtcaccgtct
   61   ---------+---------+---------+---------+---------+---------+ 120
        ccccgggtgtcggtccacgttgacgtcgtcaggccacggttccctggtgccagtggcaga a         G   A   H   S   Q   V   Q   L   Q   Q   S   G   A   K   G   P   R   S   P   S   -
                             B       E
                             a       c
                             m       o
                             H       R
                             I       I
        cctcaggtgagtggatccgaattc
  121   ---------+---------+---- 144
        ggagtccactcacctaggcttaag
                                    --- (SEQ ID NO:52)
   a         P   Q   V   S   G   S   E   F   -
```

FIGURE 5

(SEQ ID NOS: 53-57)

```
                              H
                              i
                              n
                              d
                              I
                              I
                              I    (SEQ ID NO:53) ---
         aagcttcgccaccatgggatggagctgtatcatcctcttcttggtagcaacagctacagg
    1    ----------+----------+----------+----------+----------+----------+    60
         ttcgaagcggtggtaccctacctcgacatagtaggagaagaaccatcgttgtcgatgtcc (SEQ ID NO:54)   M  G  W  S  C  I  I  L  F  L  V  A  T  A  T taagggctcacagtagcaggcttgaggtctggacatatatatgggtgacaatgacatcc
   61    ----------+----------+----------+----------+----------+----------+   120
         attcccgagtgtcatcgtccgaactccagacctgtatatatacccactgttactgtagg A                          S
                                   p                          a
                                   a                          c
                                   L                          I
                                   I
         actttgcctttctctccacaggtgtgcactccgacattgagctcacccagtctccagaca
   121   ----------+----------+----------+----------+----------+----------+   180
         tgaaacggaaagagaggtgtccacacgtgaggctgtaactcgagtgggtcagaggtctgt (SEQ ID NO:55)          G  V  H  S  D  I  E  L B
                 X                                                  a
                 h                                                  m
                 o                                                  H
                 I                                                  I
         aagctcgagctgaaacgtgagtagaatttaaactttgcttcctcaattggatcc
   181   ----------+----------+----------+----------+-----   234
         ttcgagctcgactttgcactcatcttaaatttgaaacgaaggagttaacctagg
                                                                --- (SEQ ID NO:57)
(SEQ ID NO:56)   L  E  L  K
```

FIGURE 7

Fig.12.
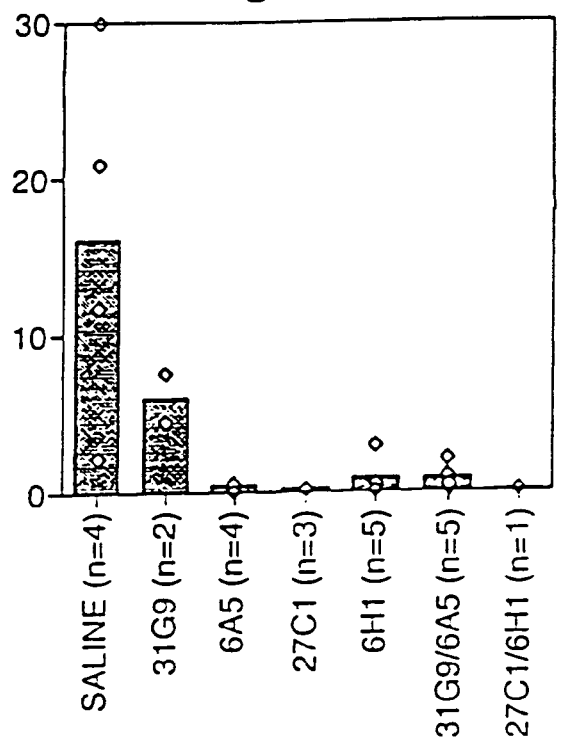
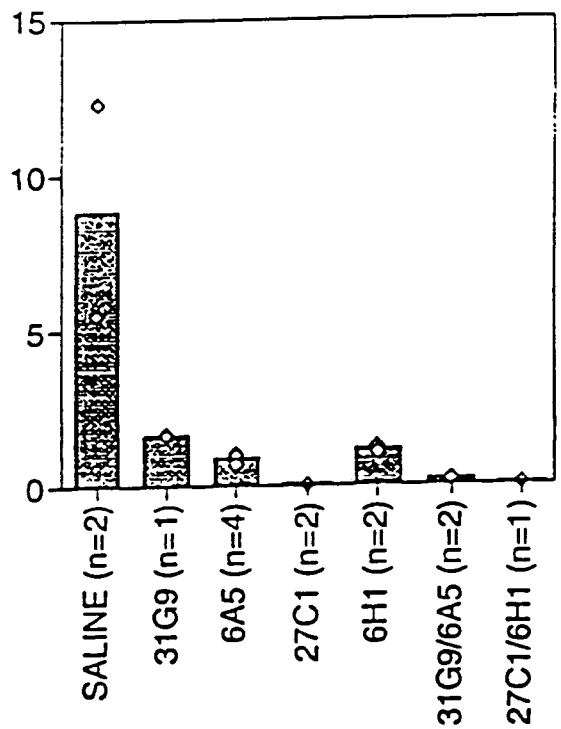

Figure 14

```
         10              20              30              40
GAA ATT GTG CTG ACT CAG CCA TCC TCC CTG TCT GCA TCT GTA GGA
 E   I   V   L   T   Q   P   S   S   L   S   A   S   V   G>

50              60              70              80              90
GAC AGA GTC ACC ATC ACT TGC CGG GCA AGT CAG GGC ATT GGA GAT GAT
 D   R   V   T   I   T   C   R   A   S   Q   G   I   G   D   D>

100             110             120             130             140
TTG GGC TGG TAT CAG CAG AAG CCA GGG AAA GCC CCT ATC CTC CTG ATC
 L   G   W   Y   Q   Q   K   P   G   K   A   P   I   L   L   I>

150             160             170             180             190
TAT GGT ACA TCC ACT TTA CAA AGT GGG GTC CCG TCA AGG TTC AGC GGC
 Y   G   T   S   T   L   Q   S   G   V   P   S   R   F   S   G>

200             210             220             230             240
AGT GGA TCT GGG ACA GAT TTC ACT CTC ACC ATC AAC AGC CTG CAG CCT
 S   G   S   G   T   D   F   T   L   T   I   N   S   L   Q   P>

250             260             270             280
GAA GAT TTT GCA ACT TAT TAC TGT CTA CAA GAT TCC AAT TAC CCG CTC
 E   D   F   A   T   Y   Y   C   L   Q   D   S   N   Y   P   L>

290     300             310             320
ACT TTC GGC GGA GGG ACA CGA CTG GAG ATT AAA CGT        (SEQ ID NO:58)
 T   F   G   G   G   T   R   L   E   I   K   R>       (SEQ ID NO:59)
```

Figure 19

```
         10              20              30              40
GAG GTG CAG CTG GTG GAG TCT GGG GGA GGC GTG GTC CAG CCT GGG AGG
 E   V   Q   L   V   E   S   G   G   G   V   V   Q   P   G   R
 50              60              70              80              90
TCC CTG AGA CTC TCC TGT GCA GCG TCT GGA TTC ACC TTC AGT AGC TAT
 S   L   R   L   S   C   A   A   S   G   F   T   F   S   S   Y
        100             110             120             130             140
GGC ATG CAC TGG GTC CGC CAG GCT CCA GGC AAG GGG CTG GAG TGG GTG
 G   M   H   W   V   R   Q   A   P   G   K   G   L   E   W   V
        150             160             170             180             190
GCA GTT ATA TGG TAT GAT GGA AGT AAT AAA TAC TAT GCA GAC TCC GTG
 A   V   I   W   Y   D   G   S   N   K   Y   Y   A   D   S   V
        200             210             220             230             240
AAG GGC CGA TTC ACC ATC TCC AGA GAC AAT TCC AAG AAC ACG CTG TAT
 K   G   R   F   T   I   S   R   D   N   S   K   N   T   L   Y
        250             260             270             280
CTG CAA ATG GAC AGC CTG AGA GCC GAG GAC ACG GCC GTG TAT TAC TGT
 L   Q   M   D   S   L   R   A   E   D   T   A   V   Y   Y   C
        290             300             310             320             330
GGA AGA ACG CTG GAG TCT AGT TTG TGG GGC CAA GGG ACC CTG GTC ACC
 G   R   T   L   E   S   S   L   W   G   Q   G   T   L   V   T
        340
GTC TCC TCA  (SEQ ID NO:60)
 V   S   S   (SEQ ID NO:61)
```

Figure 19 (ii)

```
         10              20              30              40
TCG TCT GAG CTG ACT CAG GAC CCT GCT GTG TCT GTG GCC TTG GGA CAG
 S   S   E   L   T   Q   D   P   A   V   S   V   A   L   G   Q 50              60              70              80              90
ACA GTC AGG ATC ACA TGC CAA GGA GAC AGC CTC AGA AGC TAT TAT GCA
 T   V   R   I   T   C   Q   G   D   S   L   R   S   Y   Y   A 100             110             120             130             140
AGC TGG TAC CAG CAG AAG CCA GGA CAG GCC CCT GTA CTT GTC ATC TAT
 S   W   Y   Q   Q   K   P   G   Q   A   P   V   L   V   I   Y 150             160             170             180             190
GGT AAA AAC AAC CGG CCC TCA GGG ATC CCA GAC CGA TTC TCT GGC TCC
 G   K   N   N   R   P   S   G   I   P   D   R   F   S   G   S 200             210             220             230             240
AGC TCA GGA AAC ACA GCT TCC TTG ACC ATC ACT GGG GCT CAG GCG GAA
 S   S   G   N   T   A   S   L   T   I   T   G   A   Q   A   E 250             260             270             280
GAT GAG GCT GAC TAT TAC TGT AAC TCC CGG GAC AGC AGT AGT ACC CAT
 D   E   A   D   Y   Y   C   N   S   R   D   S   S   S   T   H 290             300             310             320             330
CGA GGG GTG TTC GGC GGA GGG ACC AAG CTG ACC GTC CTA GGT    (SEQ ID NO:62)
 R   G   V   F   G   G   G   T   K   L   T   V   L   G    (SEQ ID NO:63)
```

Figure 19 (iii)

```
        10                  20                  30                  40
TCG TCT GAG CTG ACT CAG GAC CCT GCT GTG TCT GTG GCC TTG GGA CAG
 S   S   E   L   T   Q   D   P   A   V   S   V   A   L   G   Q 50                 60                  70                  80                  90
ACA GTC AGG ATC ACA TGC CAA GGA GAC AGC CTC AGA AGC TAT TAT GCA
 T   V   R   I   T   C   Q   G   D   S   L   R   S   Y   Y   A 100                 110                 120                 130                 140
AGC TGG TAC CAG CAG AAG CCA GGA CAG GCC CCT GTA CTT GTC ATC TAT
 S   W   Y   Q   Q   K   P   G   Q   A   P   V   L   V   I   Y 150                 160                 170                 180                 190
GGT AAA AAC AAC CGG CCC TCA GGG ATC CCA GAC CGA TTC GCT GGC TCC
 G   K   N   N   R   P   S   G   I   P   D   R   F   A   G   S 200                 210                 220                 230                 240
AAC TCA GGA AAC ACA GCT TCC TTG ACC ATC ACT GGG GCT CAG GCG GAG
 N   S   G   N   T   A   S   L   T   I   T   G   A   Q   A   E 250                 260                 270                 280
GAT GAG GCT GAC TAT TAC TGT AGC TCC CGG GAC AGC AGT GGT AAC CAT
 D   E   A   D   Y   Y   C   S   S   R   D   S   S   G   N   H 290                300                 310                 320
GTG GTT TTC GGC GGA GGG ACC AAG CTG ACC GTC CTA GGT    (SEQ ID NO:64)
 V   V   F   G   G   G   T   K   L   T   V   L   G    (SEQ ID NO:65)
```

Figure 19(iv)

```
         10              20              30              40
GAT GTT GTG ATG ACT CAG TCT CCA TCC TCC CTG TCT GCA TCT GTA GGA
 D   V   V   M   T   Q   S   P   S   S   L   S   A   S   V   G 50              60              70              80              90
GAC AGA GTC ACC ATC ACT TGC CGG GCC AGT CAG GGC ATT AGC AAT TAT
 D   R   V   T   I   T   C   R   A   S   Q   G   I   S   N   Y 100             110             120             130             140
TTA GCC TGG TAT CAG CAA AAA CCA GGG AAA GCC CCT AAG CTC CTG ATC
 L   A   W   Y   Q   Q   K   P   G   K   A   P   K   L   L   I 150             160             170             180             190
TAT AAG GCA TCT ACT TTA GAA AGT GGG GTC CCA TCA AGG TTC AGT GGC
 Y   K   A   S   T   L   E   S   G   V   P   S   R   F   S   G 200             210             220             230             240
AGT GGA TCT GGG ACA GAA TTC ACT CTC ACA ATC AGC AGT CTG CAA CCT
 S   G   S   G   T   E   F   T   L   T   I   S   S   L   Q   P 250             260             270             280
GAA GAT TTT GCA ACT TAC TAC TGT CAA CAG AGT TAC AGT ACC CCT CGA
 E   D   F   A   T   Y   Y   C   Q   Q   S   Y   S   T   P   R 290             300             310             320
ACG TTC GGC CAA GGG ACC AAA GTG GAT ATC AAA CGT              (SEQ ID NO:66)
 T   F   G   Q   G   T   K   V   D   I   K   R              (SEQ ID NO:67)
```

HUMAN ANTIBODIES SPECIFIC FOR TGFβ2

CROSS-REFERENCE TO RELATED APPLICATIONS

This application is a continuation-in-part of U.S. patent application Ser. No. 08/571,755 filed Dec. 13, 1995 (now abandoned) and a continuation of U.S. patent application Ser. No. 09/054,847 filed Apr. 3, 1998 (now abandoned) which is in turn a continuation of PCT/GB96/02450 filed on Oct. 7, 1996. Priority of all of the foregoing applications is claimed under 35 U.S.C. § 120. Each of the foregoing applications is incorporated by reference herein in its entirety.

BACKGROUND OF THE INVENTION

This invention relates to specific binding members for human transforming growth factor (TGFβ) and materials and methods relating thereto. In particular, it relates to specific binding members comprising antibody binding domains; for example, human antibodies. Human antibodies against human TGFβ may be isolated and utilised in the treatment of disease, particularly fibrotic disease and also immune/inflammatory diseases. The isolation of antiself antibodies from antibody segment repertoires displayed on phage has been described (A. D. Griffiths et al. EMBO J. 12, 725-734, 1993; A. Nissim et al. EMBO J. 13, 692-698, 1994; A. D. Griffiths et al. 13, 3245-3260, 1994; C. Barbas et al. Proc. Natl. Acad. Sci. USA 90, 10003-10007 1993; WO93/11236). However, the present invention provides specific antibodies against human TGFβ and further against particular isoforms of TGFβ, which antibodies have unexpected and advantageous properties.

TGFβ is a cytokine known to be involved in many cellular processes such as cell proliferation and differentiation, embryonic development, extracellular matrix formation, bone development, wound healing, hematopoiesis and immune and inflammatory responses (A. B. Roberts & M. Sporn 1990 pp419-472 in Handbook of Experimental Pharmacology eds M. B. Sporn & A. B. Roberts, Springer Heidelberg; J. Massague et al. Annual Rev. Cell Biol. 6, 597-646, 1990).

The accumulation of excessive extra-cellular matrix is associated with various fibrotic diseases. Thus there is a need to control agents such as TGFβ including TGFβ1 and TGFβ2 to prevent their deleterious effects in such diseases and this is one application of human antibodies to human TGFβ.

The modulation of immune and inflammatory responses by TGFbetas includes (i) inhibition of proliferation of all T-cell subsets (ii) inhibitory effects on proliferation and function of B lymphocytes (iii) down-regulation of natural-killer cell activity and the T-cell response (iv) regulation of cytokine production by immune cells (v) regulation of macrophage function and (vi) leucocyte recruitment and activation.

A further application of antibodies to TGFβ may be in the treatment of immune/inflammatory diseases such as rheumatoid arthritis, where these functions need to be controlled.

It is a demanding task to isolate an antibody fragment specific for TGFβ of the same species. Animals do not normally produce antibodies to self antigens, a phenomenon called tolerance (G. J. Nossal Science 245, 147-153, 1989). In general, vaccination with a self antigen does not result in production of circulating antibodies. It is therefore difficult to raise human antibodies to human self antigens. There are also in addition, ethical problems in vaccinating humans. In relation to the raising of non-human antibodies specific for TGFβ, there are a number of problems. TGFβ is an immunosuppressive molecule and further, there is strong conservation of sequence between human and mouse TGFβ molecules. Mouse and human TGFβ1 only differ by one amino acid residue, an alanine (human) to serine (mouse) change at a buried residue (R. Derynck et al. J. Biol. Chem. 261, 4377-4379, 1986). Mouse and human TGFβ2 only differ at three residues; residue 59 (T mouse, S human); residue 60 (K mouse, R human) and residue 94 (N mouse; K human). This makes it difficult to raise antibodies in mice against human TGFβ. Further, any antibodies raised may only be directed against a restricted set of epitopes.

Polyclonal antibodies binding to human TGFβ (human TGFβ1 and human TGFβ2) against both neutralising and non-neutralising epitopes have been raised in rabbit (Danielpour et al. Growth Factors 2 61-71, 1989; A. Roberts et al. Growth Factors 3, 277-286, 1990), chicken (R&D Systems, Minneapolis) and turkey (Danielpour et al. J. Cell Physiol. 138, 79-86, 1989). Peptides representing partial TGFβ sequences have also been used as immunogens to raise neutralising polyclonal antisera in rabbits (W. A Border et al. Nature 346, 371-374, 1990; K. C. Flanders Biochemistry 27, 739-746, 1988; K. C. Flanders et al, Growth Factors 3, 45-52, 1990). In addition there have been limited reports of isolation of mouse monoclonals against TGFβ. Following immunisation with bovine TGFβ2 (identical to human TGFβ2), three non-neutralising monoclonal antibodies were isolated that are specific for TGFβ2 and one neutralising antibody that is specific for TGFβ1 and TGFβ2 (J. R. Dasch et al. J. Immunol. 142, 1536-1541, 1989). In another report, following immunisation with human TGFβ1, neutralising antibodies were isolated which were either specific for TGFβ1 or cross-reacted with TGFβ1, TGFβ2 and TGFβ3 (C. Lucas et al. J. Immunol. 145, 1415-1422, 1990). A neutralising mouse monoclonal antibody which binds both TGFβ2 and TGFβ3 isoforms is available commercially from Genzyme Diagnostics.

The present specification discloses the first isolation of human antibodies directed against human TGFβ, including human TGFβ1 and human TGFβ2. A mouse monoclonal antibody directed against human TGFβ1 is available from R&D Systems. This antibody only weakly neutralises TGFβ1 in a neutralisation assay. Neutralising mouse monoclonal antibodies have also been generated from mice immunised with human TGFβ1 peptides comprising amino acid positions 48 to 60 (antibody reactive with TGFβ1, TGfβ2 and TGFβ3) and amino acid positions 86-101 (antibody specific for TGFβ1; M. Hoefer & F. A. Anderer Cancer Immunol. Immunother. 41, 302-308, 1995).

Phage antibody technology (WO92/01047; PCT/GB92/00883; PCT/GB92/01755; WO93/11236) offers the ability to isolate directly human antibodies against human TGFβ. In application WO93/11236 the isolation of antiself antibodies from phage display libraries was disclosed and it was suggested that antibodies specific for TGFβ could be isolated from phage display libraries.

The present application shows that antibodies of differing specificities for TGFβ molecules may be isolated. TGFβ1, TGFβ2 and TGFβ3 are a closely related group of cytokines. They are dimers consisting of two 112 amino acid monomers joined by an interchain disulphide bridge. TGFβ1 differs from TGFβ2 by 27 mainly conservative changes and from TGFβ3 by 22 mainly conservative changes. These differences have been related to the 3D structure (M. Schlunegger & M. G. Grutter Nature 358, 430-434, 1992).

The present applicants have isolated inter alia antibodies which are essentially specific for TGFβ1 (very low cross-reactivity with TGFβ2); antibodies which are essentially specific for TGFβ2 (very low cross-reactivity TGFβ1); and antibodies which bind both TGFβ1 and TGFβ2. Hence, these three different types of antibodies, each type with distinctive binding specificities must recognise different epitopes on the TGFβ molecules. These antibodies have low cross-reactivity with TGFβ3 as assessed by binding studies using biosensor assays (e.g. BIACore™), ELISA and radioreceptor assays. The most extensively studied antibody, 6B1 IgG4, shows 9% cross-reactivity with TGFβ3 as compared with TGFβ2, as determined by their relative dissociation constants, determined using a biosensor.

TGFβ isoforms are initially exported from cells as inactive, latent forms (R. Pircher et al, Biochem. Biophys. Res. Commun. 136, 30-37, 1986; L. M. Wakefield et al., *Growth Factors* 1, 203-218, 1989). These inactive forms are activated by proteases in plasma to generate the active form of TGFβ. It is this active form of TGFβ2 which binds to receptors promoting the deposition of extracellular matrix and the other biological effects of TGFβ. The active form of TGFβ represents a relatively low proportion of TGFβ that is in the plasma. Therefore, for a neutralising antibody against TGFβ to be most effective at preventing fibrosis the antibody should recognise the active but not the latent form. In Example 6, it is demonstrated that a preferred antibody of this invention ("6B1 IgG4 ") recognises the active but not the latent form of TGFβ2.

The epitope of 6B1 IgG4 has been identified using a combination of peptide display libraries and inhibition studies using peptides from the region of TGFβ2 identified from phage selected from the peptide phage display library. This is described in Examples 11 and 14. The sequence identified from the peptide library is RVLSL (SEQ ID NO: 1) and represents amino acids 60 to 64 of TGFβ2 (Example 11). The antibody 6B1 IgG4 has also been shown to bind to a peptide corresponding to amino acids 56 to 69 of TGFβ2 (TQHSRVLSLYNTIN) (SEQ ID NO: 2) with a three amino acid (CGG) extension at the N-terminus. Although, RVLSL is the minimum epitope, 6B1 IgG4 is likely to bind to further adjacent amino acids. Indeed, if the epitope is three dimensional there may be other non-contiguous sequences to which the antibody will bind. 6B1 IgG4 shows much weaker binding to the peptide corresponding to amino acids 56 to 69 of TGFβ1 (CGGTQYSKVLSLYNQHN) (SEQ ID NO: 3).

The results of Example 14 support the assignment of the epitope of 6B1 IgG4 on TGFβ2 to the aminoacids in the region of residues 60 to 64. The peptide used in this example, residues 56 to 69, corresponds to the amino acids of alpha helix H3 (M. P. Schlunegger & M. G. Grutter Nature 358 430-434, 1992; also known as the α3 helix (S. Daopin et al Proteins: Structure, Function and Genetics 17 176-192, 1993). TGFβ2 forms a head-to-tail dimer with the alpha helix H3 (also referred to as the heel) of one subunit forming an interface with finger regions (including residues 24 to 37 and residues in the region of amino acids 91 to 95; also referred to as fingers 1 and 2) from the other subunit (S. Daopin et al supra). It has been proposed that the primary structural features which interact with the TGFβ2 receptor consist of amino acids at the C-terminal end of the alpha helix H3 from one chain together with residues of fingers 1 and 2 of the other chain (D. L. Griffith et al Proc. Natl. Acad. Sci. USA 93 878-883, 1996). The identification of an epitope for 6B1 IgG4 within the alpha helix H3 of TGFβ2 is consistent with 6B1 IgG4 preventing receptor binding and neutralising the biological activity of TGFβ2.

As noted above if the epitope for 6B1 IgG4 is three dimensional there may be other non-contiguous amino acids to which the antibody may bind.

There is earlier advice that antibodies directed against this region of TGFβ2 may be specific for TGFβ2 and neutralise its activity. Flanders et al (Development 113 183-191, 1991) showed that polyclonal antisera could be raised in rabbits against residues 50 to 75 of mature TGFβ2 and that these antibodies recognised TGFβ2 but the TGFβ1 in Western blots. In an earlier paper, K. C. Flanders et al (Biochemistry 27 739-746, 1988) showed that polyclonal antisera raised in rabbits against amino acids 50 to 75 of TGFβ1 could neutralise the biological activity of TGFβ1. The antibody isolated in this application 6B1 IgG4 is a human antibody directed against the amino acids in this region which neutralises the biological activity of human TGFβ2. It is surprising that such a neutralising antibody against TGFβ2 can be isolated in humans (where immunisation with a peptide cannot be used for ethical reasons) directly from a phage display antibody repertoire.

The knowledge that the residues of the alpha helix H3 form a neutralising epitope for TGFβ2 means that phage displaying neutralising antibodies are obtainable by selection from phage antibody repertoires by binding to a peptide from this region coupled to a carrier protein such as bovine serum albumin or keyhole limpet haemocyanin. This approach may be applied to select antibodies which are capable of neutralising the biological activity of TGFβ1 by selecting on the peptide TQYSKVLSLYNQHN (SEQ ID NO: 125) coupled to a carrier protein. It is possible that such an approach may be extended to peptides from receptor binding regions of TGFβ isoforms, other than the H3 alpha helix.

It has further been demonstrated by the present inventors that antibodies specific for TGFβ are obtainable by isolation from libraries derived from different sources of immunoglobulin genes: from repertoires of natural immunoglobulin variable domains, e.g. from immunised or non-immunised hosts; and synthetic repertoires derived from germline V genes combined with synthetic CDR3s. The properties of these antibodies in single chain Fv and whole IgG4 format are described.

As noted above WO93/11236 suggested that human antibodies directed against human TGFβ could be isolated from phage display libraries. Herein it is shown that the phage display libraries from which antiself antibodies were isolated in WO93/11236 may be utilised as a source of human antibodies specific for particular human TGFβ and TGFβ isoforms. For instance, in example 1 of the present application, the antibody 1A-E5 specific for TGFβ1 and the antibodies 2A-H11 and 2A-A9 specific for TGFβ2 were isolated from the "synthetic library" described in examples 5 to 7 of WO93/11236 and in Nissim et al. (1994; supra). Also, the phage display library derived from peripheral blood lymphocytes (PBLs) of an unimmunised human (examples 1 to 3 of WO93/11236) was the source for the antibody 1B2 specific for TGFβ1. Phage display libraries made subsequently utilising antibody genes derived from human tonsils and bone marrow, have also provided sources of antibodies specific for human TGFβ. Thus human TGFβ is an example of a human self antigen to which antibodies may be isolated from "large universal libraries". Human antibodies against human TGFβ with improved properties can be obtained by chain shuffling for instance combining the VH domains of antibodies derived from one library with the VL domains of another library thus expanding the pool of VL partners tested for each VH domain. For instance, the antibodies 6B1, 6AH, 6A5 and 6H1 specific for TGFβ2 utilise the 2A-H11 VH domain isolated from the "synthetic library" combined with a light chain from the PBL library.

Thus the VH and VL domains of antibodies specific for TGFβ can be contributed from phage display libraries derived from rearranged V genes such as those in PBLs, tonsil and bone marrow and from V domains derived from cloned germline V segments combined with synthetic CDRs. There are also shown to be a diverse range of antibodies which are specific for TGFβ1 or TGFβ2. The antibodies which have been isolated both against TGFβ1 and TGFβ2 have mainly utilised V genes derived from VH germlines of the VH3 family. A wider variety of light chain variable regions have been used, of both the lambda and kappa types.

Individual antibodies which have been isolated have unexpectedly advantageous properties. For example, the antibodies directed against TGFβ2 (6H1, 6A5 and 6B1) have been shown to bind to TGFβ2 with slow off-rates (off-rate constants $k_{off}$ of the order of $10^{-3}$ $s^{-1}$ and dissociation constants of less than $10^{-8}M$) to neutralise TGFβ2 activity in in vitro assays and to be potent in in vivo applications. The antibody 6B1 IgG4 has been shown to bind specifically to TGFβ2 in immunohistochemistry in mammalian tissues and not to cross-react with other antigens in human tissues. The properties of these antibodies may make them particularly suitable for therapeutic applications. The fact that these antibodies share the same heavy chain, shows that VH domains can be effective with a number of different light chains, although there may be differences in potency or subtle changes of epitope with different light chains. As shown in Examples 3 and 4 and Tables 4 and 5, 6B1 IgG4 is the most potent antibody in neutralising TGFβ2 activity in the radioreceptor assay and the TF1 proliferation assay. Its properties may however be expected to be qualitatively similar to the antibodies 6A5 and 6H1 with which it shares a common VH domain. Thus the reduction in neural scarring observed on treatment with 6A5 single chain Fv and 6H1 IgG4 shown in Example 5 would be expected to be reproduced with 6B1. The antibodies directed against TGFβ1 (1AE5, 1AH6 particularly 1B2 and their derivatives) also have unexpectedly advantageous properties. Antibody 27C1/10A6 derived from 1B2 by chain shuffling, spiking and conversion into whole antibody IgG4, has been shown to be potent in an in vitro scarring model. The VH domain of this antibody was derived by site directed "spiking" mutagenesis from the parent antibody 7A3. A large number of spiked clones were obtained which show similar properties in in vitro assays. There can be a number of changes in CDR3 of the VH compared to 27C1, for instance, 28A-H11 differs in 7 of the 14 positions, 2 of which are non-conservative changes. Thus there may be up to 50% of the residues in the VH CDR3 changed without affecting binding properties.

Antibodies specific for human TGFβ, including human TGFβ1 and human TGFβ2, have been shown to be effective in animal models for the treatment of fibrotic diseases and other diseases such as rheumatoid arthritis where TGFβ is overexpressed. Antibodies against TGFβ have been shown to be effective in the treatment of glomerulonephritis (W. A Border et al. Nature 346, 371-374, 1990); neural scarring (A. Logan et al. Eur. J. Neurosci. 6, 355-363, 1994); dermal scarring (M. Shah et al. Lancet 339, 213-214 1992; M. Shah et al. J. Cell Science 107, 1137-1157, 1994; M. Shah et al. 108, 985-1002, 1995); lung fibrosis (S. N. Giri et al. Thorax 48, 959-966, 1993); arterial injury (Y. G. Wolf, L. M. Rasmussen & E. Ruoslahti J. Clin. Invest. 93, 1172-1178, 1994) and rheumatoid arthritis (Wahl et al J. Exp. Medicine 177, 225-230, 1993). It has been suggested that TGFβ3 acts antagonistically to TGFβ1 and TGFβ2 in dermal scarring (M. Shah et al. 1995 supra.). Therefore, antibodies to TGFβ1 or TGFβ2 with apparent low cross-reactivity to TGFβ3, as assessed by binding studies using a biosensor assay (e.g. BIACore™), ELISA or a radioreceptor assay, as disclosed in this application, that is to say antibodies which bind preferentially to TGFβ1 or TGFβ2 compared with TGFβ3, should be advantageous in this and other conditions such as fibrotic conditions in which it is desirable to counteract the fibrosis promoting effects of TGFβ1 and TGFβ2. An antibody which cross-reacts strongly with TGFβ3 has however had an effect in an animal model of rheumatoid arthritis (Wahl et al., 1993, supra).

There are likely to be applications further to the above mentioned conditions, as there are several other in vitro models of disease where antibodies against TGFβ have shown promise of therapeutic efficacy. Of particular importance may be the use of antibodies against TGFβ for the treatment of eye diseases involving ocular fibrosis, including proliferative retinopathy (R. A. Pena et al. (ref. below), retinal detachment and post glaucoma (P. T. Khaw et al., *Eye* 8 188-195, 1994) drainage surgery. Connor et al. (*J. Clin. Invest* 83 1661-1666, 1989) showed that much higher levels of TGFβ2 were present in vitreous aspirates from patients with intraocular fibrosis associated with proliferative retinopathy compared with patients with uncomplicated retinal detachment without ocular fibrosis and that the biological activity of this TGFβ2 could be neutralised with antibodies directed against TGFβ2. Moreover, Pena et al. (*Invest. Ophthalmology. Vis. Sci.* 35: 2804-2808, 1994) showed that antibodies against TGFβ2 inhibit collagen contraction stimulated by TGFβ2. Contraction of the vitreous gel by fibroblasts and other cell types plays a critical role in the proliferative retinopathy disease process, a process thought to be mediated by TGFβ2.

There is other evidence pointing to TGFβ2 being the most important TGFβ isoform promoting intraocular fibrosis. TGFβ2 has been shown to be the predominant isoform of TGFβ in the neural retina, retinal pigment epithelium-choroid and vitreous of the human eye (Pfeffer et al. *Exp. Eye Res.* 59: 323-333, 1994) and found in human aqueous humour in specimens from eyes undergoing cataract extraction with intraocular lens implantation (Jampel et al. *Current Eye Research* 9: 963-969, 1990). Non-transformed human retinal pigment epithelial cells predominantly secrete TGFβ2 (Kvanta *Opthalmic Res.* 26: 361-367, 1994).

Other diseases which have potential for treatment with antibodies against TGFβ include adult respiratory distress syndrome, cirrhosis of the liver, post myocardial infarction, post angioplasty restenosis, keloid scars and scleroderma. The increase level of expression of TGFβ2 in osteoporosis (Erlenbacher et al. *J. Cell Biol.* 132: 195-210, 1996) means that this is a disease potentially treatable by antibodies directed against TGFβ2.

The use of antibodies against TGFβ for the treatment of diseases has been the subject of patent applications for fibrotic disease (WO91/04748); dermal scarring (WO92/17206); macrophage deficiency diseases (PCT/US93/00998); macrophage pathogen infections (PCT/US93/02017); neural scarring (PCT/US93/03068); vascular disorders (PCT/US93/03795); prevention of cataracts (WO95/13827). The human antibodies against human TGFβ disclosed in this application should be valuable in these conditions.

It is shown herein that the human antibodies both against human TGFβ1 and against human TGFβ2 can be effective in the treatment of fibrosis in animal models of neural scarring and glomerulonephritis in either single chain Fv and whole antibody format. This is the first disclosure of the effectiveness of antibodies directed only against TGFβ2 as sole treatment in these indications, although some effectiveness of antibodies against TGFβ2 only has been observed in a lung fibrosis model (Giri et al. Thorax 48, 959-966, 1993 supra). The effectiveness of the human antibodies against human TGFβ in treatment of fibrotic disease has been determined by measuring a decrease in the accumulation of components of the extracellular matrix, including fibronectin and laminin in animal models.

The evidence of efficacy of the antibodies against TGFβ2 and TGFβ1 describe herein in prevention of neural scarring in the animal model experiment means that these antibodies are likely to be effective in other disease states mediated by TGFβ. For comparison, antisera isolated from turkeys directed against TGFβ isoforms by Danielpour et al. (*Cell Physiol.* 138: 79-86, 1989) have been shown to be effective in the prevention of dermal scarring (Shah et al. *J. Cell Science* 108: 985-1002, 1995), neural scarring (Logan et al., supra) and in in vitro experiments relating to proliferative retinopathy (Connor et al., supra).

Terminology

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is homologous to, an antibody binding domain. These proteins can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), eg prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, Embo Journal, 10, 3655-3659, (1991).

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Neutralisation

This refers to the situation in which the binding of a molecule to another molecule results in the abrogation or inhibition of the biological effector function of another molecule.

Functionally Equivalent Variant Form

This refers to a molecule (the variant) which although having structural differences to another molecule (the parent) retains some significant homology and also at least some of the biological function of the parent molecule, e.g. the ability to bind a particular antigen or epitope. Variants may be in the form of fragments, derivatives or mutants. A variant, derivative or mutant may be obtained by modification of the parent molecule by the addition, deletion, substitution or insertion of one or more amino acids, or by the linkage of another molecule. These changes may be made at the nucleotide or protein level. For example, the encoded polypeptide may be a Fab fragment which is then linked to an Fc tail from another source. Alternatively, a marker such as an enzyme, flourescein, etc, may be linked.

Substantial Part

A molecule may comprise only a part of the sequence referred to. The part sequence will be of sufficient length to substantially retain the function of interest of the full-length sequence.

Comprise

This is generally used in the sense of inclusiveness, that is to say permitting the presence of one or more features or components.

The present invention generally provides a specific binding member comprising an antibody antigen binding domain. More particularly it provides a specific binding member for TGFβ, and even more particularly the isoforms TGFβ1 and TGFβ2.

The present invention provides a specific binding member which comprises a human antibody antigen binding domain specific for TGFβ and more particularly for TGFβ1 and/or TGFβ2 and which has low cross reactivity with TGFβ3. The cross-reactivity may be as assessed using any or all of the following assays: biosensor (e.g. BIACore™), ELISA and radioreceptor. The present invention provides specific binding member which comprises a human antibody antigen binding domain specific for TGFβ1 and/or TGFβ2 which binds preferentially to these isoforms compared with TGFβ3.

The TGFβ may be human TGFβ.

The specific binding member may be in the form of an antibody fragment such as single chain Fv (scFv). Other types of antibody fragments may also be utilised such as Fab, Fab', F(ab')$_2$, Fabc, Facb or a diabody (G. Winter & C. Milstein Nature 349, 293-299, 1991; WO94/13804). The specific binding member may be in the form of a whole antibody. The whole antibody may be in any of the forms of the antibody isotypes e.g. IgG, IgA, IgE, and IgM and any of the forms of the isotype subclasses eg IgG1 or IgG4.

The specific binding member may also be in the form of an engineered antibody eg bispecific antibody molecules (or fragments such as F(ab')$_2$) which have one antigen binding arm (i.e. specific binding domain) against TGFβ and another arm against a different specificity. Indeed the specific binding members directed against TGFβ1 and/or TGFβ2 described herein may be combined in a bispecific diabody format. For example the antibodies 31G9 directed against TGFβ1 and 6H1 directed against TGFβ2 may be combined to give a single dimeric molecule with both specificities.

The binding domain may comprise part or all of a VH domain encoded by a germ line gene segment or a rearranged gene segment. The binding domain may comprise part or all of either a VL kappa domain or a VL lambda domain.

The binding domain may be encoded by an altered or variant form of a germ line gene with one or more nucleotide alterations (addition, deletion, substitution and/or insertion), e.g. about or less than about 25, 20, 15, 10 or 5 alterations, 4, 3, 2 or 1, which may be in one or more frameworks and/or CDR'S.

The binding domain may comprise a VH3 gene sequence of one of the following germ lines; the DP49 germ line; the DP53 germ line; the DP50 germ line; the DP46 germ line; or a re-arranged form thereof.

A preferred VH domain for anti-TGFβ2 specific binding members according to the present invention is that of 6H1 VH, whose sequence is shown in FIG. 2(a)(i) (SEQ ID NO: 6). 6H1 may be paired with a variety of VL domains, as exemplified herein. Amino acid sequence variants of 6H1 VH may be employed.

The specific binding member may neutralise the in vitro and/or in vivo effect of TGFβ that is one or more of the isoforms, particularly TGFβ1 and/or TGFβ2.

The specific binding member may be a high affinity antibody. Preferred affinities are discussed elsewhere herein.

The binding domain may comprise part or all of a VH domain having either an amino acid sequence as shown in FIG. 1(a)(i) (SEQ ID NO: 8), (ii) (SEQ ID NO: 111), (iii) (SEQ ID NO: 112) or (iv) (SEQ ID NO: 10) or FIG. 1(c)(i) (SEQ ID NO: 12) or a functionally equivalent variant form of a said amino acid sequence.

The binding domain may comprise part or all of a VH domain encoded by either a nucleotide sequence as shown in FIG. 1(a)(i) (SEQ ID NO: 7), (ii) (SEQ ID NO: 113), (iii) (SEQ ID NO: 114) or (iv) (SEQ ID NO: 9) or FIG. 1(c)(i) (SEQ ID NO: 11) or a functionally equivalent variant form of a said nucleotide sequence.

The binding domain may comprise part or all of a VL domain having either an amino acid sequence as shown in FIG. 1(a)(v) (SEQ ID NO: 14) or FIG. 1(b) (SEQ ID NOS: 16, 18) or a functionally equivalent variant form of a said amino acid sequence.

The binding domain may comprise part or all of a VL domain encoded by either a nucleotide sequence as shown in FIG. 1(a)(v) (SEQ ID NO: 13) or FIG. 1(b) (SEQ ID NOs: 15, 17) or a functionally equivalent variant form of a said nucleotide sequence.

The binding domain may comprise part or all of a VH domain having a variant form of the FIG. 1(a)(i) amino acid (SEQ ID NO: 8), the variant form being one of those as provided by FIG. 3 (SEQ ID NOS: 19 to 35).

The binding domain may comprise part or all of a VH domain having either an amino acid sequence as shown in FIG. 2(a)(i) (SEQ ID NO: 6) or (ii) (SEQ ID NO: 37), (iii) (SEQ ID NO: 116), (v) (SEQ ID NO: 120), (vi) (SEQ ID NO: 122) or a functionally equivalent variant form of a said amino acid sequence.

The binding domain may comprise part or all of a VH domain encoded by either a nucleotide sequence as shown in FIG. 2(a)(i) (SEQ ID NO:5) or (ii) (SEQ ID NO: 36), (iii) (SEQ ID NO: 115), (v) (SEQ ID NO: 119), (vi) (SEQ ID NO: 121) or a functionally equivalent variant form of a said nucleotide sequence.

The binding domain may comprise part or all of a VL domain having either an amino acid sequence as shown in any of FIG. 2(a)(iv) (SEQ ID NO:118) or 2(b)(i) to (vi) (SEQ ID NOS: 39, 41, 43, 45, 47, 124) or functionally equivalent variant form of a said amino acid sequence.

The binding domain may comprise part or all of a VL domain encoded by either a nucleotide sequence as shown in any of FIGS. 2(a)(iv) (SEQ ID NO:117) 2(b)(i) to (vi), (SEQ ID NOS: 38, 40, 42, 44, 46, 123) or a functionally equivalent variant form of a said nucleotide sequence.

The binding domain may be specific for both TGFβ1 and TGFβ2. The binding domain may be specific for both human TGFβ1 and human TGFβ2. The specific binding member may be in the form of scFv.

The binding domain may comprise part or all of a VL domain having either an amino acid sequence as shown in FIG. 4 (SEQ ID NO: 49) or a functionally equivalent variant form of said amino acid sequence. The binding domain may comprise part or all of a VL domain encoded by either the nucleotide sequence as shown in FIG. 4 (SEQ ID NO: 48) or a functionally equivalent variant form of said nucleotide sequence.

In particular, the binding domain may comprise one or more CDR (complementarity determining region) with an amino acid sequence shown in any of the figures. In a preferred embodiment, the binding domain comprises one or more of the CDRs, CDR1, CDR2 and/or CDR3 shown in the Figures, especially any of those shown in italics in FIG. 19 (SEQ ID NOS: 126, 127, 128, 129, 130, 131, 132, 133, 134, 135, 136, 137).

In a preferred embodiment, the binding domain comprises a VH CDR3 sequence as shown, especially as shown in italics in FIG. 19 (SEQ ID NOS: 128, 131, 134, 137). Functionally equivalent variant forms of the CDRs are encompassed by the present invention, in particular variants which differ from the CDR sequences shown by addition, deletion, substitution or insertion of one or more amino acids and which retain ability to bind the antigen and optionally one or more of the preferred characteristics for specific binding members of the present invention as disclosed herein. The specific binding member may comprise all or part of the framework regions shown flanking and between the CDRs in the Figures, especially FIG. 19 (SEQ ID NOS: 61, 63, 65, 67), or different framework regions including modified versions of those shown.

So-called "CDR-grafting" in which one or more CDR sequences of a first antibody is placed within a framework of sequences not of that antibody, e.g. of another antibody is disclosed in EP-B-0239400.

The present invention also provides a polypeptide with a binding domain specific for TGFβ which polypeptide comprises a substantial part or all of either an amino acid sequence as shown in any of FIG. 1(a) (SEQ ID NOS:8, 10, 14, 111, 112), FIG. 1(b) (SEQ ID NOS: 16, 18), FIG. 1(c) (SEQ ID NO: 12), FIG. 2(a) (SEQ ID NOS: 6, 37, 116, 118, 120, 122), FIG. 2(b) (SEQ ID NOS: 39, 41, 43, 45, 47, 124), FIG. 4 (SEQ ID NO:49) or a functionally equivalent variant form of a said amino acid sequence. The polypeptide may comprise a substantial part or all of an amino acid sequence which is a functionally equivalent variant form of the FIG. 1(a)(i) (SEQ ID NO: 8) amino acid sequence, the variant being one of those variants as shown in FIG. 3 (SEQ ID NOS: 19 to 35).

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion), maybe less than about 20 alterations, less than about 15 alterations, less than about 10 alterations or less than about 5 alterations, 4, 3, 2 or 1. Alterations may be made in one or more framework regions and/or one or more CDR's.

A specific binding member according to the invention may be one which competes for binding to TGFβ1 and/or TGFβ2 with any specific binding member which both binds TGFβ1 and/or TGFβ2 and comprises part of all of any of the sequences shown in the Figures. Competition between binding members may be assayed easily in vitro, for example by tagging a specific reporter molecule to one binding member which can be detected in the presence of other untagged binding member(s), to enable identification of specific binding members which bind the same epitope or an overlapping epitope.

Preferred specific binding members for TGFβ1 compete for binding to TGFβ1 with the antibody CS37, discussed in more details elsewhere herein.

Preferred specific binding members for TGFβ2 compete for binding to TGFβ2 with the antibody 6B1 discussed in more detail else where herein. They may bind the epitope RVLSL (SEQ ID NO: 1) or a peptide comprising the amino acid sequence RVLSL (SEQ ID NO: 1), particularly such a peptide which adopts an α-helical conformation. They may bind the peptide TQHSRVLSLYNTIN (SEQ ID NO: 2) In testing for this, a peptide with this sequence plus CGG at the N-terminus may be used. Specific binding members according to the present invention may be such that their binding for TGFβ2 is inhibited by a peptide comprising RVLSL (SEQ ID NO: 1), such as a peptide with the sequence TQHSRVLSLYNTIN (SEQ ID NO: 2). In testing for this, a peptide with this sequence plus CGG at the N-terminus may be used.

TQHSRVLSLYNTIN (SEQ ID NO: 2) corresponds to the alpha helix H3 (residues 56-69) of TGFβ2, as discussed elsewhere herein. The equivalent region in TGFβ1 has the sequence TQYSKVLSLYNQHN (SEQ ID NO: 125). Anti-TGFβ1 antibodies which bind this region are of particular interest in the present invention, and are obtainable for example by panning a peptide with this sequence (or with CGG at the N-terminus) against a phage display library. Specific binding members which bind the peptide may be selected by means of their binding, and may be neutralising for TGFβ1 activity. Binding of such specific binding members to TGFβ1 may be inhibited by the peptide TQYSKVLSLYNQHN (SEQ ID NO: 125) (optionally with CGG at the N-terminus).

A specific binding member according to the present invention which is specific for TGFβ2 may show no or substantially no binding for the latent form of TGFβ2, e.g.

be specific for the active form of TGFβ2. 6B1 is shown in Example 6 to have this property.

6B1 is particularly suitable for therapeutic use in the treatment of fibrotic disorders because it has the following advantageous properties. 6B1 binds to TGFβ2 with a dissociation constant of 2.3 nM in the single chain form and 0.89 nM for the whole antibody form, 6B1 IgG4 (Example 13). The antibody 6B1 IgG4 neutralises the biological activity of TGFβ2 in an antiproliferation assay ($IC_{50}$ 2n M; examples 7 and 10) and in a radioreceptor assay ($IC_{50}$ less than 1 nM; Table 6). The antibody binds to the peptide TQHSRVLSLYNTIN (SEQ ID NO: 2) ($TGF\beta2_{56-69}$) from the alpha helix H3 of TGFβ2 and recognises the corresponding peptide from TGFβ1 more weakly. 6B1 recognises the active but not the latent form of TGFβ2 (Example 6), recognises TGFβ2 in mammalian tissues by ICC and does not bind non-specifically to other human tissues (Example 12). The antibody preferentially binds to TGFβ2 as compared to TGFβ3, the cross-reactivity with TGFβ3 being 9% as determined by the ratio of the dissociation constants.

The other antibodies described in this application which contain the 6H1 VH domain, 6H1 and 6A5 have similar properties. The dissociation constants of were determined to be 2 nM for 6B1 IgG4 (Example 2) and 0.7 nM for 6A5 single chain Fv (Table 1). 6H1 IgG4 neutralises the biological activity of TGFβ2 with $IC_{50}$ values of 12 to 15 nM (Examples 7 and 10). 6A5 and 6H1 inhibit receptor binding of TGFβ2 in a radioreceptor assay with $IC_{50}$ values of about 1 nM in the single chain Fv format and 10 nM or below in the whole antibody, IgG4 format. Both 6H1 IgG4 and 6A5 scFv were shown to be effective in the prevention of neural scarring (Example 5).

Therefore for the first human antibodies directed against TGFβ2 are provided which have suitable properties for treatment of diseases characterised by the deleterious presence of TGFβ2. Such antibodies preferably neutralise TGFβ2 and preferably have a dissociation constant for TGFβ2 of less than about 100 nM, more preferably about 10 nM, more preferably below about 5 nM. The antibodies preferentially bind to TGFβ2 as compared to TGFβ3, preferably have less than 20% cross-reactivity with TGFβ3 (as measured by the ratio of the dissociation constants) and preferably have less than about 10% cross-reactivity.

The antibody preferably recognises the active but not the latent form of TGFβ2.

For antibodies against TGFβ1, the properties desired for an antibody to be effective in treatment of fibrotic disease are similar. Such antibodies preferably neutralise TGFβ1 and have a dissociation constant for TGFβ1 of less than about 100 nM, more preferably below about 10 nM, more preferably below about 5 nM. The antibodies preferentially bind to TGFβ1 as compared to TGFβ3, preferably have less than about 20% cross-reactivity with TGFβ3 (as measured by the ratio of the dissociation constants) and more preferably have less than about 10% cross-reactivity.

The antibody preferably recognises the active but not the latent form of TGFβ1. The antibody 31G9 has a dissociation constant of 12 nM (Table 5). The antibodies CS37 scFv and 27C1/10A6 IgG4 show $IC_{50}$ values in a radioreceptor assay of 8 nM and 9 nM respetively, indicating a dissociation contstant in the low nanomolar range. 27C1/10A6 IgG4 was shown to be effective in a neural scarring model. Cross-reactivity of antibodies of the 1B2 lineage with TGFβ3 is very low (Example 9).

In addition to an antibody sequence, the specific binding member may comprise other amino acids, e.g. forming a peptide or polypeptide, or to impart to the molecule another functional characteristic in addition to ability to bind antigen. For example, the specific binding member may comprise a label, an enzyme or a fragment thereof and so on.

The present invention also provides a polynucleotide which codes for a polypeptide with a binding domain specific for TGFβ which polynucleotide comprises a substantial part or all of a nucleotide sequence which codes for either an amino acid sequence as shown in any one of FIG. 1(a) (SEQ ID NOS: 8, 10, 14, 111, 112), FIG. 1(b) (SEQ ID NOS: 16, 18), FIG. 1(c) (SEQ ID NO: 12), FIG. 2(a) (SEQ ID NOS: 6, 37, 116, 118, 120, 122), FIG. 2(b) (SEQ ID NOS: 39, 41, 43, 45, 47, 124), FIG. 4 (SEQ ID NO: 49) or a functionally equivalent variant form of a said amino acid sequence. The polynucleotide may code for a polypeptide with a binding domain specific for TGFβ which polynucleotide comprises a substantial part or all of a nucleotide sequence which codes for an amino acid sequence which is a functionally equivalent variant form of the FIG. 1(a)(i) amino acid sequence (SEQ ID NO:8), the variant being one of those as shown in FIG. 3 (SEQ ID NOS: 19 to 35). The polynucleotide may code for a polypeptide with a binding domain specific for TGFβ which polynucleotide comprises a substantial part or all of a either a nucleotide sequence as shown in any of FIG. 1(a) (SEQ ID NOS: 7, 9, 13, 113, 114), FIG. 1(b) (SEQ ID NOS: 15, 17), FIG. 1(c) (SEQ ID NO: 11), FIG. 2(a) (SEQ ID NOS: 5, 36, 115, 117, 119, 121), FIG. 2(b) (SEQ ID NOS: 38, 40, 42, 44, 46, 123), FIG. 4 (SEQ ID NO: 48) or a functionally equivalent variant form of said nucleotide sequence. The polynucleotide may code for a polypeptide with a binding domain specific for TGFβ which polynucleotide comprises a substantial part or all a nucleotide sequence which codes for a variant form of the FIG. 1(a)(i) amino acid sequence (SEQ ID NO: 8), the variant being one of those as shown in FIG. 3 (SEQ ID NOS: 19 to 35).

The present invention also provides constructs in the form of plasmids, vectors, transcription or expression cassettes which comprise least one polynucleotide as above.

The present invention also provides a recombinant host cell which comprises one or more constructs as above.

A specific binding member according to the present invention may be made by expression from encoding nucleic acid. Nucleic acid encoding any specific binding member as provided itself forms an aspect of the present invention, as does a method of production of the specific binding member which method comprises expression from encoding nucleic acid thereof. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. The term "isolate" encompasses all these possibilities.

The nucleic acid may encode any of the amino acid sequences shown in any of the Figures, or any functionally equivalent form. The nucleotide sequences employed may be any of those shown in any of the Figures, or may be a variant, allele or derivative thereof. Changes may be made at the nucleotide level by addition, substitution, deletion or insertion of one or more nucleotides, which changes may or may not be reflected at the amino acid level, dependent on the degeneracy of the genetic code.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

The expression of antibodies and antibody fragments in prokaryotic cells such as *E. coli* is well established in the art. For a review, see for example Pluckthun, A. Bio/Technology 9: 545-551 (1991). Expression in eukaryotic cells in culture is also available to those skilled in the art as an option for production of a specific binding member, see for recent reviews, for example Reff, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Following production of a specific binding member it may be used for example in any of the manners disclosed herein, such as in the formulation of a composition, pharmaceutical or a diagnostic product, such as a kit comprising in addition to the specific binding member one or more reagents for determining binding of the member to cells, as discussed. A composition may comprise at least one component in addition to the specific binding member.

The present invention also provides pharmaceuticals which comprise a specific binding member as above, optionally with one or more excipients.

The present invention also provides the use of a specific binding member as above in the preparation of a medicament to treat a condition in which it is advantageous to counteract the fibrosis promoting effects of TGFβ. The condition may be a fibrotic condition characterized by an accumulation in a tissue of components of the extracellular matrix. The components of the extracellular matrix may be fibronectin or laminin.

The condition may be selected from the group consisting of:
glomerulonephritis
neural scarring
dermal scarring
ocular scarring
lung fibrosis
arterial injury
proliferative retinopathy
retinal detachment
adult respiratory distress syndrome
liver cirrhosis
post myocardial infarction
post angioplasty restenosis
keloid scarring
scleroderma
vascular disorders
cataract
glaucoma
proliferative retinopathy.

The condition may be neural scarring or glomerulonephritis.

The present invention also provides the use of a specific binding member as above, in the preparation of a medicament to treat an immune/inflammatory disease condition in which it is advantageous to counteract the effects of TGFβ. Illustrative conditions are rheumatoid arthritis, macrophage deficiency disease and macrophage pathogen infection.

The present invention also provides a method which comprises administering to a patient a therapeutically effective amount of a specific binding member as above in order to treat a condition in which it is advantageous to counteract the fibrosis promoting effects of TGFβ. Fibrotic conditions are listed above.

The present invention also provides a method which comprises administering to a patient a prophylactically effective amount of a specific binding member as above in order to prevent a condition in which it is advantageous to prevent the fibrosis promoting effects of TGFβ. Fibrotic conditions are listed above.

The present invention also provides methods which comprise administering to patients prophylactically and/or therapeutically effective amounts of a specific binding member as above in order to prevent or treat an immune/inflammatory disease condition in which it is advantageous to counteract the effects of TGFβ. Illustrative conditions are stated above.

Thus, various aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals, which may be any mammal, particularly rodent, e.g. mouse, horse, pig, sheep, goat, cattle, dog, cat or human. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Further aspects of the invention and embodiments will be apparent to those skilled in the art. In order that the present invention is fully understood, the following examples are provided by way of exemplification only and not by way of limitation.

BRIEF DESCRIPTION OF DRAWINGS

FIG. 1 shows the DNA and protein sequences of antibodies specific for TGFβ1. FIG. 1(a) shows the amino acid and encoding nucleic acid sequences of antibody variable domains of antibodes to TGFβ1 isolated directly from repertoires: FIG. 1(a)(i)—1B2 VH (also known as 7A3 VH) (SEQ ID NOS: 7, 8); FIG. 1(a)(ii)—1A-E5 VH (SEQ ID NOS: 113, 111); FIG. 1(a)(iii)—1A-H6VH (SEQ ID NOS: 114, 112); FIG. 1(a)(iv)—31G9 VH (SEQ ID NOS: 9, 10); FIG. 1(a)(v)—31G9 VL (SEQ ID NOS: 13, 14). FIG. 1(b) shows the amino acid and encoding nucleic acid sequences of antibody light chain variable domains of antibodies to TGFβ1 isolated by chain shuffling: FIG. 1(b)(i)—7A3 VL (SEQ ID NOS: 15, 16); FIG. 1(b)(ii)—10A6 VL (SEQ ID NOS: 17, 18). FIG. 1(c)(i) shows the amino acid and encoding nucleic acid sequences for 27C1 VH (SEQ ID NOS: 11, 12), from an antibody to TGFβ1 isolated from a CDR3 spiking experiment.

FIG. 2 shows the DNA and protein sequences of antibodies specific for TGFβ2. FIG. 2(a) shows amino acid and encoding nucleic acid sequences for variable domains of antibodies to TGFβ2 isolated directly from repertoires: FIG. 2(a)(i)—2A-H11 VH (also known as 6H1 VH) (SEQ ID NOS: 5, 6); FIG. 2(a)(ii)—2A-A9 VH (also known as 11E6 VH) (SEQ ID NOS: 36, 37); FIG. 2(a)(iii)—Gold 11-VH (SEQ ID NOS: 115, 116); FIG. 2(a)(iv)—Gold 11-VL (SEQ ID NOS: 117, 118); FIG. 2(a)(v)—1-G2 (SEQ ID NOS: 119, 120); and FIG. 2(a)(vi)—1-H6 (SEQ ID NOS: 121, 122). FIG. 2(b) shows amino acid and encoding nucleic acid sequences of antibody variable domains of antibodies specific for TGFβ2 isolated following chain shuffling: FIG. 2(b)(i)—6H1 VL (SEQ ID NO: 38, 39); FIG. 2(b)(ii)—6A5 VL (SEQ ID NOS: 40, 41); FIG. 2(b)(iii)—6B1 VL (SEQ ID NOS: 42, 43); FIG. 2(b)(iv) 11E6 VL (SEQ ID NOS: 44, 45); (v) FIG. 2(b)(v)—14F12 VL (SEQ ID NOS: 46, 47); FIG. 2(b)(vi)—6H1VL (SEQ ID NOS: 123, 124).

FIG. 3 shows the protein sequences of VH CDR3 of clones derived from 1B2 by 'spiking' mutagenesis (SEQ ID NOS: 19 to 35). Differences from 1B2 VH CDR3 are in bold.

FIG. 4 shows the DNA and protein sequence of the VL domain of VT37, cross-reactive between TGFβ1 and TGFβ2 (SEQ ID NOS: 48, 49).

FIG. 5 shows the DNA sequence and encoded amino acid sequence in the region of the heavy chain VH leader from the vector vhcassette2 (SEQ ID NOS: 50 to 52). Restriction enzymes HindIII, SfiI, PstI, BstEII, BamHI and EcoRI cut at the points indicated.

FIG. 7 shows the DNA sequence, including intron, and encoded amino acid sequence in the region of the light chain VL leader for the vector vlcassette1 (vlcassette CAT1) (SEQ ID NOS: 53 to 57). Restrcition enzymes HindIII, ApaLI, SacI, XhoI and BamHI cut at the sites indicated (ApaLI within the leader).

FIG. 12 shows the effect of treatment of animals with antibodies on neural scarring as measured by the deposition of (FIG. 12(a)) fibronectin and (FIG. 12(b)) laminin detected using integrated fluorescence intensity. The graphs show scatter plots of individual animal data points. The bar graph shows the mean integrated fluorescence intensity of the group.

FIG. 13(a) shows cross-reactivty of 6B1 IgG4 to a panel of non-specific antigens and TGFβ's, plotting OD405 nm for each antigen: 1—interleukin 1; 2—human lymphotoxin (TNFβ); 3—human insulin; 4—human serum albumin; 5—ssDNA; 6—oxazolone-bovine serum albumin; 7—keyhole limpet haemocyanin; 8—chicken egg white trypsin inhibitor; 9—chymotrypsinogen; 10—cytochrome C; 11—GADPH; 12—ovalbumin; 13—hen egg lysozyme; 14—bovine serum albumin; 15—TNFα; 16—TGFβ1; 17—TGFβ2; 18—TGFβ3; 19—PBS only. FIG. 13(b) shows the OD405 nm for the antibody 6A5 IgG4 against the same panel of antigens. For both FIG. 13(a) and FIG. 13(b), antigens 1 to 15 were used for coating the plate at a concentration of 10 µg/ml in PBS. The TGFbetas were coated at 0.2 µg/ml in PBS. Coating was performed at 4° C. overnight. 100 µg of each antigen was used per well and duplicates of each antigen for each IgG to be tested. IgG samples were incubated with the coated antigens at 37° C. for 2 hours after blocking with 2%. marvel-PBS. The labelled second antibody was a mouse anti-human Fc1 alkaline phosphatase conjugated and the substrate used to detect bound second antibody was PNPP at 1 mg/ml with the absorbance read at 405 nm.

FIG. 19 shows amino acid and encoding DNA sequences of regions of antibodies directed against TGFβ showing CDR sequences in italics: FIG. 19(i) 2A-H11 VH (also known as 6H1 VH) (SEQ ID NOS: 60, 61) with CDR1 (SEQ ID NO: 126), CDR 2 (SEQ ID NO: 127) and CDR3 (SEQ ID NO: 128) in italics; FIG. 19(ii) 6B1 VL (SEQ ID NOS: 62, 63) with CDR1 (SEQ ID NO: 129), CDR2 (SEQ ID NO: 130) and CDR3 (SEQ ID NO: 131) in italics; FIG. 19(iii) 6A5 VL (SEQ ID NOS: 64, 65) with CDR1 (SEQ ID NO: 132), CDR2 (SEQ ID NO: 133) and CDR3 (SEQ ID NO: 134) in italics and FIG. 19(iv) 6H1 VL (SEQ ID NOS: 66, 67) with CDR1 (SEQ ID NO: 135), CDR2 (SEQ ID NO: 136) and CDR3 (SEQ ID NO: 137) in italics.

Figure 6:
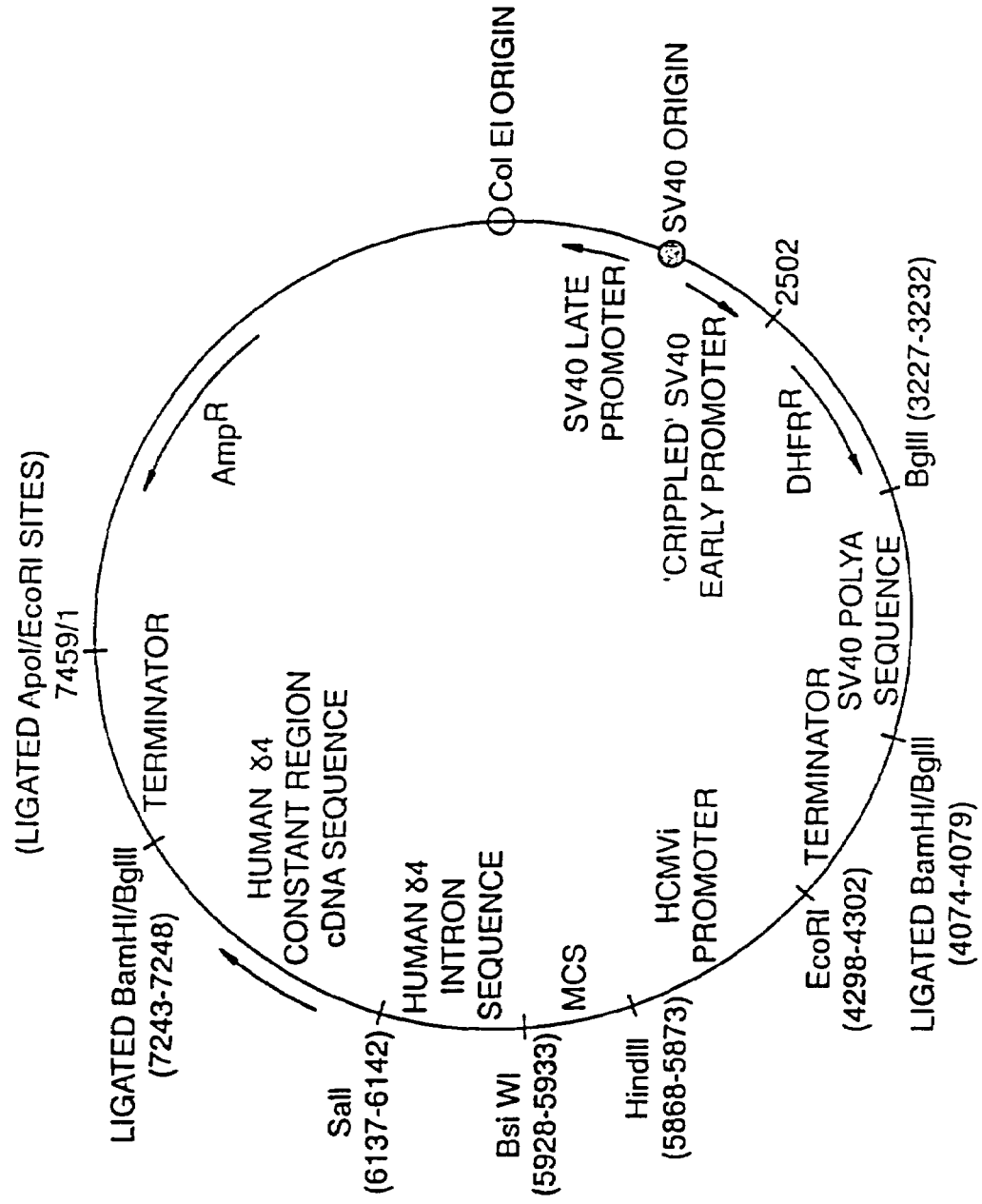
FIG. 6 shows a map of the vector pG4D100 (not to scale). Multiple cloning site (MCS): 5'-HindIII-PacI-BamHI-(XanI)-(PmlI)-(NheI)-AscI-(BssHII)-XhoI-PmeI-BsiWI-3'. Restriction sites shown in brackets are not unique.

All documents mentioned herein are incorporated by reference.

BRIEF DESCRIPTION OF THE INVENTION

LIST OF EXAMPLES

Example 1—Isolation of antibodies specific for TGFβ1, antibodies specific for TGFβ2 and antibodies specific for TGFβ1 and TGFβ2.

Example 2—Construction of cell lines expressing whole antibodies.

Example 3—Neutralisation of TGFβ activity by antibodies assessed using in vitro assays.

Example 4—Inhibition by antibodies of TGFβ binding to receptors.

Example 5—Prevention of neural scarring using antibodies against TGFβ.

Example 6—Determination of Binding of 6B1 IgG4 to Active or Latent Form of TGFβ$_2$.

Example 7—Neutralisation by antibodies directed against TGFβ2 of the inhibitory effect of TGFβ isoforms on cells proliferation.

Example 8—Inhibition by antibodies directed against TGFβ2 of binding of other TGFβ isoforms to receptors measured in a radioreceptor assay.

Example 9—Assessment of TGFβ1 antibodies for potential therapeutic use.

Example 10—Construction of a high expressing cell line for 6B1 IgG4 using the glutamine synthase selection system and assessment in a neutralisation assay.

Example 11—Determination of the epitope on TGFβ2 for the antibody 6B1 using a peptide phage display library.

Example 12—Determination of the binding of 6B1 IgG4 to tissues by immunocytochemistry (ICC).

Example 13—Determination of the kinetic parameters of 6B1 IgG4 and single chain Fv for binding to TGFβ2.

Example 14—Binding of a Peptide Corresponding to Residues 56 to 69 of TGFβ2 to 6B1 IgG4.

Example 15—Prevention of glomerulonephritis using antibodies against TGFbeta.

EXAMPLE 1

Isolation and Characterisation of Antibodies Binding to TGFβ1 and TGFβ2

Identification and Characterisation of Antibodies to Human TGFβ1 by Selection of Naive and Synthetic Phage Antibody Repertoires Antibody Repertoires The following antibody repertoires were used:
1. Peripheral blood lymphocyte (PBL) library derived from unimmunized human (Marks, J. D., Hoogenboom, H. R. Bonnert, T. P., McCafferty, J., Griffiths, A. D. & Winter, G. (1991) J. Mol. Biol. 222, 581-597).
2. Synthetic library (Nissim, A., Hoogenboom, H. R., Tomlinson, I. M., Flynn, G., Midgley, C., Lane, D. and Winter, G. (1994) EMBO J. 13, 692-698) derived from cloned human germline VH genes and synthetic CDR3s with a fixed light chain.
3. Tonsil library derived from the tonsils of unimmunised humans. Tonsil B cells were isolated from freshly removed (processed within 2 hours) whole tonsils provided by Addenbrookes Hospital, Hills Road, Cambridge, U.K. Each tonsil was processed as follows. Tonsils were placed in a petri dish containing 5 ml of PBS and macerated with a scalpel blade to release the cells. The suspension was transferred to a fresh tube and large debris allowed to sediment under gravity for 5 minutes. The cell suspension was then overlaid onto 10 mls of Lymphoprep in a 50 ml polypropylene tube (Falcon) and centrifuged at 1000×g 20 minutes at room temperature (no brake) and cells at the interface harvested with a glass pipette. These were diluted to a final volume of 50 ml in RPMI medium at 37° C. and centrifuged at 500×g for 15 minutes at room temperature. The supernatant was aspirated and the cells washed another two times with RPMI.

Polyadenylated RNA was prepared from pelleted cells using the "Quickprep™ mRNA Kit" (Pharmacia Biotech, Milton Keynes, U.K.). The entire output of cells from one tonsil (ca. 1×10⁶ cells) was processed using one Oligo (dT)—Cellulose Spun column and processed exactly as described in the accompanying protocol. MRNA was ethanol precipitated as described and resuspended in 40 ml RNase free water.

The cDNA synthesis reaction was set up using the "First-Strand cDNA Synthesis" Kit (Pharmacia Biotech, Milton Keynes, U.K.) as follows:

| RNA | 20 µl (heated to 67° C. 10 minutes before use) |
|---|---|
| 1st strand buffer | 11 µl |
| DTT solution | 1 µl |
| pd(N)₆ primer | 1 µl |

After gentle mixing, the reaction was incubated at 37° C. for 1 hour.

Human VH genes were amplified from tonsil cDNA using the nine family-based back primers (VH 1b/7a -6a back Sfi, which introduce a SfiI site at the 5'-end, Table 1) together with an equimolar mixture of the four JH forward primers (JH 1-2, 3, 4-5, 6, for; Marks et al., 1991 supra). Thus, nine primary PCR amplifications were performed. Each reaction mixture (50 µl) comprised 2 µl cDNA template, 25 pmol back primer, 25 pmol forward primers, 250 µM dNTPs, 1.5 mM MgCl₂, 50 mM KCl, 10 mM Tris-HCL pH 8.3 and 2.5 u of Taq polymerase (Boehringer). The reaction mixture was overlaid with mineral (paraffin) oil and was cycled 30 times (94° C. for 1 min, 55° C. for 1 min, 72° C. for 1 min) using a Techne thermal cycler. The products were purified on a 1% (w/v) agarose gel, isolated from the gel using "Geneclean" (Bio 101 Inc.) and resuspended in 15 µl of water. The amplified VH genes were recombined with human VL genes derived from PBLs (Marks et al., 1991 supra) together with the (Gly₄, Ser)₃ linker (Huston, J. S., et al. 1988 Proc Natl Acad Sci USA. 85: 5879-83) by PCR assembly (Marks et al, 1991 supra). The VH-linker-VL antibody constructs were cloned into the SfiI and NotI sites of the phagemid vector, pCANTAB6 (McCafferty, J., et al. 1994 Appl. Biochem. Biotech. 47: 157-173) to give a library of 6×10⁷ clones.

4. Large single chain Fv library derived from lymphoid tissues including tonsil, bone marrow and peripheral blood lymphocytes.

Polyadenylated RNA was prepared from the B-cells of various lymphoid tissues of 43 non-immunised donors using the "Quickprep mRNA Kit" (Pharmacia). First-strand cDNA was synthesized from mRNA using a "First-strand cDNA synthesis" kit (Pharmacia) using random hexamers to prime synthesis. V-genes were amplified using family-specific primers for VH, Vκ and Vλ genes as previously described (Marks et al., supra) and subsequently recombined together with the (Gly₄, Ser)₃ scFv linker by PCR assembly. The VH-linker-VL antibody constructs were cloned into the SfiI and NotI sites of the phagemid vector, PCANTAB 6. Ligation, electroporation and plating out of the cells was as described previously (Marks et al, 1991 supra). The library was made ca. 1000× larger than that described previously by bulking up the amounts of vector and insert used and by performing multiple electroporations. This generated a scFv repertoire that was calculated to have ca. 1.3×10¹⁰ individual recombinants which by Bst NI fingerprinting were shown to be extremely diverse.

a. Induction of Phage Antibody Libraries

The four different phage antibody repertoires above were selected for antibodies to TGFβ-1. The VH synthetic (Nissim et al., 1994 supra), tonsil, 'large', scFv and PBL (Marks et al., 1991 supra) repertoires were each treated as follows in order to rescue phagemid particles. 500 ml prewarmed (37° C.) 2YTAG (2YT media supplemented with 100 µg/ml ampicillin and 2% glucose) in a 2 l conical flask was inoculated with approximately 3×10¹⁰ cells from a glycerol stock (−70° C.) culture of the appropriate library. The culture was grown at 37° C. with good aeration until the OD$_{600nm}$ reached 0.7 (approximately 2 hours). M13K07 helper phage (Stratagene) was added to the culture to a multiplicity of infection (moi) of approximately 10 (assuming that an OD$_{600nm}$ of 1 is equivalent to 5×10⁸ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2YTAK (2YT media supplemented with 100 µg/ml ampicillin and 50 µg/ml kanamycin), and the culture incubated overnight at 30° C. with good aeration (300 rpm). Phage particles were purified and concentrated by three polyethylene glycol (PEG) precipitations (Sambrook, J., Fritsch, E. F., & Maniatis, T. (1990). Molecular Cloning—A Laboratory Manual. Cold Spring Harbour, N.Y.) and resuspended in PBS to 10¹² transducing units (tu)/ml (ampicillin resistant clones).

b. Panning of Phage Antibody Library on TGFβ-1

Phage induced from the four repertoires were each separately panned on TGFβ1. A 75 mm ×12 mm immuno tube (Nunc; Maxisorp) was coated with 2 ml of recombinant human TGFβ1 (0.5 ug/ml, Genzyme) in PBS overnight at 4° C. After washing 3 times with PBS, the tube was filled with 3% MPBS (3% 'Marvel' skimmed milk powder, 1×PBS) and incubated for 2 hours at 37° C. for blocking. The wash was repeated, phagemid particles ($10^{13}$ tu) in 2 ml of 3% MPBS were added and the tube incubated stationary at 37° C. for 1 hour. The tube was washed 20 times with PBST (0.1%), then 20 times with PBS. Bound phage particles were eluted from the tube by adding 2 ml of 100 mM triethylamine, and incubating the tube stationary at room temperature for 10 minutes. The eluted material was immediately neutralised by pipetting into a tube containing 1 ml 1M Tris.HCl (pH7.4). Phage were stored at 4° C. 1.5 ml of the eluted phage were used to infect 20 ml of logarithmically growing *E. coli* TG1 (Gibson, T. J. (1984). PhD thesis. University of Cambridge, UK.). Infected cells were grown for 1 hour at 37° C. with light aeration in 2YT broth, and then plated on 2YTAG medium in 243 mm×243 mm dishes (Nunc). Plates were incubated overnight at 30° C. Colonies were scraped off the plates into 10 ml of 2YT broth and 15% (v/v) glycerol added for storage at −70° C.

Glycerol stock cultures from the first round of panning of each of the four repertoires on TGFβ1 were each rescued using helper phage to derive phagemid particles for the second round of panning. 250 µl of glycerol stock was used to inoculate 50 ml 2YTAG broth, and incubated in a 250 mL conical flask at 37° C. with good aeration until the $OD_{600nm}$ reached 0.7 (approximately 2 hours). M13K07 helper phage (moi=10) was added to the culture which was then incubated stationary at 37° C. for 15 minutes followed by 45 minutes with light aeration (200 rpm) at the same temperature. The culture was centrifuged and the supernatant drained from the cell pellet. The cells were resuspended in 50 ml prewarmed 2YTAK, and the culture incubated overnight at 30° C. with good aeration. Phage particles were purified and concentrated by PEG precipitation (Sambrook et al., 1990 supra) and resuspended in PBS to 1013 tu/ml.

Phage induced from the first round of panning of each of the three repertoires, was selected a second time essentially as described above except that the panning tube was coated with only 1 ml of TGFβ1 (0.5 ug/ml, Genzyme), and the volume of phage added to the tube similarly reduced. After extensive washing, bound phage were eluted from the tube using 1 ml of 100 mM triethylamine, and neutralised by the addition of 0.5 ml 1M Tris.HCl (pH7.4) as earlier described. The process of phage growth and panning was repeated over a third and a fourth round of selection.

c. Growth of Single Selected Clones for Immunoassay

Individual colonies from the third and fourth round selections were used to inoculate 100 µl 2YTAG into individual wells of 96 well tissue culture plates (Corning). Plates were incubated at 30° C. overnight with moderate shaking (200 rpm). Glycerol to 15% was added to each well and these master plates stored at—70° C. until ready for analysis.

d. ELISA to Identify Anti-TGFβ1 scFv

Clones specific for TGFβ1 were identified by ELISA, using scFv displayed on phage or soluble scFv.

i. Phage ELISA

Cells from the master plates were used to inoculate fresh 96 well tissue culture plates containing 100 µl 2YTAG per well. These plates were incubated at 37° C. for 6-8 hours or until the cells in the wells were growing logarithmically (OD600 0.2-1.0). M13K07 was added to each well to an moi of 10 and incubated stationary for 15 min then 45 min with gentle shaking (100 rpm), both at 37° C. The plates were centrifuged at 2000 rpm for 10 min and the supernatant eluted. Each cell pellet was resuspended in 100 µl 2YTAK and incubated at 30° C. overnight.

Each plate was centrifuged at 2000 rpm and the 100 µl supernatant from each well recovered and blocked in 20 µl 18% M6PBS (18% skimmed milk powder, 6×PBS), stationary at room temperature for 1 hour. Meanwhile, flexible microtitre plates which had been blocked overnight stationary at 4° C. with either 50 µl 0.2 µg/ml TGFβ1 in PBS or 50 µl PBS alone (giving an uncoated control plate), were washed 3 times in PBS and blocked for 2 h stationary at 37° C. in 3MPBS. These plates were then washed three times with PBS and 50 µl preblocked phage added to each well of both the TGFβ1-coated or uncoated plate. The plates were incubated stationary at 37° C. for 1 h after which the phage were poured off. The plates were washed by incubating for 2 min in PBST three times followed by incubating for 2 min in PBS three times, all at room temperature.

To each well of both the TGFβ1-coated and the uncoated plate, 50 µl of a 1 in 10, 000 dilution of sheep anti-fd antibody (Pharmacia) in 3MPBS was added and the plates incubated at 37° C. stationary for 1 h. Each plate was washed as described above and 50 µl of a 1 in 5, 000 dilution donkey anti-sheep alkaline phosphatase conjugate (Sigma) in 3MPBS added and incubated stationary at 37° C. for 1 h. Plates were washed as described as above followed by two rinses in 0.9% NaCl. Alkaline phosphatase activity was visualised using either the chromagenic substrate pNPP (Sigma) or the Ampak system (Dako). The absorbance signal generated by each clone was assessed by measuring the optical density at either 405 nm (pNPP) or 492 nm (Ampak) using a microtitre plate reader. Clones were chosen for further analysis if the ELISA signal generated on the TGFβ1-coated plate was at least double that on the uncoated plate.

ii. Soluble ELISA

Cells from the master plates were used to inoculate fresh 96 well tissue culture plates containing 100 µl 2YTAG per well. These plates were incubated at 30° C. for 8 hours then centrifuged at 2000 rpm for 10 min and the supernatant eluted. Each cell pellet was resuspended in 100 µl 2YTA (2YT media supplemented with 100 ug/ml ampicillin) containing 10 mM IPTG (isopropyl-B-D-thiogalactopyranoside) and incubated at 30° C. overnight.

Each plate was centrifuged at 2000 rpm and the 100 µl supernatant from each well recovered and blocked in 20 µl 18% M6PBS stationary at room temperature for 1 hour. Meanwhile, flexible microtitre plates which had been blocked overnight stationary at 4° C. with either 50 µl 0.2 µg/ml TGFβ-1 in PBS or 50 µl PBS alone, were washed 3 times in PBS and blocked for 2 h stationary at 37° C. in 3% MPBS. These plates were then washed three times with PBS and 50 µl preblocked soluble scFv added to each well of both the TGFβ1-coated or uncoated plate. The plates were incubated stationary at 37° C. for 1 h after which the scFv solutions were poured off. The plates were washed by incubating for 2 min in PBST (PBS containing 1% Tween) three times followed by incubating for 2 min in PBS three times, all at room temperature.

To each well of both the TGFβ1-coated and the uncoated plate, 50 µl of a 1 in 200 dilution of the anti-myc tag murine antibody 9E10 (Munro, S. & Pelham, H. R. B. (1986) Cell 46, 291-300) in 3MPBS was added and the plates incubated at 37° C. stationary for 1 h. Each plate was washed as described above and 50 µl of a 1 in 5, 000 dilution goat anti-mouse alkaline phosphatase conjugate (Pierce) in 3MPBS added and incubated stationary at 37° C. for 1 h. Plates were washed as described above followed by two rinses in 0.9% NaCl. Alkaline phosphatase activity was visualised using either the chromagenic substrate pNPP (Sigma) or the Ampak system (Dako). The absorbance signal generated by each clone was assessed by measuring the optical density at either 405 nm (pNPP) or 492 nm (Ampak) using a microtitre plate reader. Clones were chosen for further analysis if the ELISA signal generated on the TGFβ1-coated plate was at least double that on the uncoated plate.

iii. Specificity ELISA

Clones identified as binding TGFβ-1 rather an uncoated well, as described above, were further analysed for fine specificity. Specificity ELISA's were carried out using scFv either displayed on phage or in solution as described above, except that 5 ml of media in 50 ml Falcon tubes were inoculated with each clone and grown to generate the phage or soluble scFv used in the ELISA. Microtitre plate wells were coated with 50 µl of either 0.2 µg/ml TGFβ1, 0.2 µg/ml TGFβ-2, 10 µg/ml bovine serum albumin (BSA) or PBS (the uncoated well). After preblocking both the phage (or soluble scFv) and the microtitre plates, 50 µl blocked phage (or soluble scFv) from each clone was added to a well coated with either TGFβ-1, TGFβ-2, BSA or an uncoated well. As above, alkaline phosphatse activity was visualised using either the chromagenic substrate pNPP (Sigma) or the Ampak system (Dako). Clones were considered to be specific for TGFβ-1 if the ELISA signal generated in the TGFβ-1 coated well was at least five-fold greater than the signal on either TGFβ-2, BSA or an uncoated well.

iv. Specificity Determination by BIACore™

The antibodies were also shown to be specific for TGFβ1 compared to TGFβ2 (obtained from R&D Systems Abingdon) by relative binding to the BIACore™ sensor chips coated with the appropriate antigen. TGFβ1 and TGFβ2 were immobilised by amine coupling to Biosensor CM5 sensorchips (Pharmacia) according to the manufacturers instructions. Single chain Fv fragments (35 µl; purified by immobilized metal affinity chromatography as described in example 4) were injected over the immobilized antigen at a flow rate of 5 µl/min. The amount of TGFβ bound was assessed as the total increase in resonance units (RUs) over this period. For 31G9 scFv an increase of 1059RUs was found with a TGFβ1 chip and 72 RUs was found with a TGFβ2 chip. Thus binding is much stronger to TGFβ1 than TGFβ2.

e. Sequencing of TGFβ1-Specific ScFv Antibodies

The nucleotide sequence of the TGFβ1 specific antibodies was determined by first using vector-specific primers to amplify the inserted DNA from each clone. Cells from an individual colony on a 2YTAG agar plate were used as the template for a polymerase chain reaction (PCR) amplification of the inserted DNA using the primers pUC19reverse and fdtetseq (Table 1).

Amplification conditions consisted of 30 cycles of 94° C. for 1 min, 55° C. for 1 min and 72° C. for 2 min, followed by 10 min at 72° C. The PCR products were purified using a PCR Clean-up Kit (Promega) in to a final volume of 50 µl H20. Between 2 and 5 µl of each insert preparation was used as the template for sequencing using the Taq Dye-terminator cycle sequencing system (Applied Biosystems). The primers mycseq10 and PCR-L-Link were used to sequence the light chain of each clone and PCR-H-Link and pUC19reverse to sequence the heavy chain (Table 1).

f. Sequence and Source of the Initial TGFβ1-Specific ScFv Antibodies

Four different TGFβ1 specific antibodies were isolated from the selections using the four libraries described above. Each clone name, its origin and its heavy and light chain germline are given below. The complete sequence of the VH domain genes of clones 1-B2 (SEQ ID NO: 7) and 31-G9 (SEQ ID NO: 9) are given in FIG. 1(a), together with the VL domain gene, from scFv 31-G9 (SEQ ID NO: 13).

| CLONE | LIBRARY SOURCE | VH GERMLINE | VL ISOTYPE |
|-------|----------------|-------------|------------|
| 1-B2  | PBL            | VH3 DP49    | VKappa     |
| 1A-E5 | Synthetic VH   | VH3 DP53    | VLambda    |
| 1A-H6 | Tonsil         | VH3 DP50    | VLambda    |
| 31-G9 | large scFv     | VH3 DP49    | VLambda    |

Thus these initial isolates were obtained from libraries derived from different sources-both natural V genes of unimmunized humans and synthetic libraries from cloned germline V genes together with synthetic CDRs.

2. Affinity Maturation of the Initial TGFβ1-Specific ScFv Antibodies a. Light Chain Shuffling of the TGFβ1-Specific ScFv Antibody 1-B2 i. Construction of Repertoires

The heavy chain of clone 1-B2 was recombined with the complete repertoire of light chains derived from the PBL and large (tonsil-derived) scFv repertoires. The 1-B2 heavy chain was amplified by PCR using the primers HuJh4-5For (Table 1) and pUC19reverse. Amplification conditions consisted of 30 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

The PBL and tonsil light chains were amplified by PCR using the primers fdtetseq and a mix of RL1, 2 & 3 (Table 1). Amplification conditions consisted of 30 cycles of 94° C. for 1 min, 55° C. for 1 min and 72° C. for 1 min, followed by 10 min at 72° C. The PCR product was separated through a 1% agarose-TAE gel, the band representing the amplified VL excised, and eluted from the agarose gel using the Geneclean Kit (Bio 101).

Approximately 50 ng amplified 1-B2 heavy chain and 50 ng of either amplified PBL-derived or amplified tonsil-derived light chains were combined and precipitated with sodium acetate and ethanol using 25 µg glycogen as a carrier. The precipitated DNA was pelleted by centrifugation at 13, 000 rpm in a microfuge, air dried and resuspended in 26 µl H20. This was used in an assembly amplification after the addition of reaction buffer to 1×, dNTP's to 200 nM and 5 units Taq polymerase. Amplification conditions consisted of 20 cycles of 94° C. for 1 min, 60° C. for 1 min and 72° C. for 1 min 30 s, followed by 10 min at 72° C. 10 µl of each assembly was used as the template in a 'pull-through' amplification with the primers fdtetseq and pUC19reverse. Amplification conditions consisted of 25 cycles of 94° C. for 1 min, 60° C. for 1 min and 72° C. for 1 min 30 s, followed by 10 min at 72° C.

The pull-through amplification product was separated through 1% agarose-TAE and the band representing the pull-through VH-VL excised and eluted using the Geneclean Kit. This was digested with the restriction endonucleases SfiI and NotI (NEB) and ligated (Amersham ligation system) into the phagemid vector pCantab 6, previously digested with Sfi 1 and NotI. The ligation product was used to transform electrocompetent TG1 cells, plated out on 2YTAG plates and incubated overnight at 30° C. Approximately $1\times10^5$ individual clones were generated from the light chain-shuffle of the 1-B2 heavy chain with the PBL-derived light chains and approximately $1\times10^6$ for the shuffle with the tonsil-derived light chains.

ii. Selection of Light Chain Shuffle Repertoires

The two light chain-shuffle repertoires were selected for TGFβ1-specific antibodies. Phagemid particles were recovered from each repertoire as described earlier for the initial libraries. Recovered phage were preblocked for 1 h in a final volume of 100 µl 3MPBS. Approximately $10^{11}$ tu phage were used in the first round selection and between $10^9$ and $10^{10}$ for subsequent selections. For the first round selections, biotinylated TGFβ1 to a final concentration of 100 nM was added to the preblocked phage and incubated stationary at 37° C., for 1 h.

For each selection, 100 µl Dynabeads suspension (Dynal) was separated on a magnet and the beads recovered and preblocked for 2 h in 1 ml 3MPBS. The beads were recovered on a magnet and resuspended in the phagemid/biotinylated TGFβ1 mixture and incubated at room temperature for 15 min while being turned end-over-end. The beads were captured on a magnet and washed four times with PBST followed by three washes in PBS. After each wash, the beads were captured on a magnet and resuspended in the next wash. Finally, half of the beads were resuspended in 10 µl 50 mM DTT (the other half of the beads stored at 4° C. as a back-up) and incubated at room temperature for 5 min. The whole bead suspension was then used to infect 5 ml logarithmically-growing TG1 cells. This was incubated at 37° C., stationary for 15 min then with moderate shaking for 45 min, plated on 2YTAG plates and incubated overnight at 30° C.

Colonies were scraped off the plates into 10 ml of 2YT broth and 15% (v/v) glycerol added for storage at −70° C. A 250 µl aliqout of each plate scrape was used to inoculate 2YTAG and phagemid particles rescued as described earlier. For each repertoire, three rounds of selection using biotinylated TGFβ1 was performed, essentially identical to the first round selection described above. All selections were at 100 nM TGFβ1 except for the third round selection of the tonsil-derived light chain repertoire where the concentration of biotinylated TGFβ1 in the selection was reduced to 50 nM.

iii. Identification of TGFβ1-Specific ScFv Antibodies from Light Chain Shuffle Repertoires ScFv antibodies specific to TGFβ1 were identified by both phage and soluble ELISA, and sequenced, as described earlier. Three new TGFβ1-specific scFv antibodies were identified, two with PBL-derived light chains and one with a tonsil-derived light chain. All three had the 1B2 heavy chain sequence (DP49), described earlier. The sequences are summarised below and the complete sequence of each VL domain gene is given in FIG. 1(b) (SEQ ID NOS: 15, 17).

| CLONE | VL SOURCE | VH GERMLINE | VL ISOTYPE |
|-------|-----------|-------------|------------|
| 7-A3  | PBL       | DP49 (1B2)  | VKappa     |
| 10-A6 | PBL       | DP49 (1B2)  | VLambda    |
| 14-A1 | Tonsil    | DP49 (1B2)  | VLambda    |

Thus the VH domain 1B2 derived from the PBL library can be combined with VL domains derived from both PBL and tonsil libraries.

b. CDR3 'Spiking' of the TGFβ1-Specific ScFv Antibody 1B2 i. Construction of 'Spiked' Repertoire

An 84 mer mutagenic oligonucleotide primer, 1B2 mutVHCDR3, was first synthesized (see Table 1). This primer was 'spiked' at 10%; i.e. at each nucleotide position there is a 10 probability that a non-parental nucleotide will be incorporated. The 1-B2 heavy chain was amplified by PCR using the primers pUC19reverse and 1B2 mutVH-CDR3. Amplification conditions consisted of 30 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

The parental 1B2 light chain was amplified by PCR using the primers fdtetseq and RL3 (Table 1). Amplification conditions consisted of 30 cycles of 94° C. for 1 min, 55° C. for 1 min and 72° C. for 1 min, followed by 10 min at 72° C. The PCR product was separated through a 1% agarose-TAE gel, the band representing the amplified VL excised, and eluted from the agarose gel using the Geneclean Kit (Bio 101).

Approximately 50 ng amplified 'spiked' 1-B2 heavy chain and 50 ng of amplified parental 1B2 light chain were combined and precipitated with sodium acetate and ethanol using 25 µg glycogen as a carrier. The precipitated DNA was pelleted by centrifugation at 13,000 rpm in a microfuge, air dried and resuspended in 26 µl H20. This was used in an assembly amplification after the addition of reaction buffer to 1×, dNTP's to 200 nM and 5 units Taq polymerase. Amplification conditions consisted of 25 cycles of 94° C. for 1 min, 65° C. for 4 min. Five µl of each assembly was used as the template in a 'pull-through' amplification with the primers fdtetseq and pUC19reverse. Amplification conditions consisted of 30 cycles of 94° C. for 1 min, 55° C. for 2 min and 72° C. for 1 min, followed by 10 min at 72° C.

The pull-through amplification product was separated through 1% agarose-TAE and the band representing the pull-through 'spiked' VH-VL excised and eluted using the Geneclean Kit. This was digested with the restriction endonucleases SfiI and NotI (NEB) and ligated (Amersham ligation system) into the phagemid vector pcantab 6, previously digested with SfiI and NotI. The ligation product was used to transform electrocompetent TG1 cells, plated out on 2YTAG plates and incubated overnight at 30° C. Approximately $4\times10^6$ individual clones were generated from this VH CDR3 'spiking' of the 1-B2 VH CDR3.

ii. Selection of 1B2 CDR3 Spike Repertoire

The repertoire was selected for new TGFβ1-specific scFv antibody by one round of panning on 1 µg/ml TGFβ1 followed by two rounds of selection with biotinylated TGFβ1 at 50 nM using methods as described earlier.

iii. Identification of TGFβ1-Specific ScFv Antibodies from the 1B2 CDR3 Spike Repertoire ScFv antibodies specific to TGFβ1 were identified by both phage and soluble and phage ELISA, and sequenced, as described earlier. Clone 27C1 was isolated from the spiked repertoire. It is virtually identical to clone 1B2 but with three differences in the heavy chain CDR3. The complete sequence of clone 27C1 is given in FIG. 1(c). The 27C1 VH domain was combined with the 10A6 VL domain in the construction of the whole antibody 27C1/10A6 IgG4 (example 2). The properties of this antibody are described in more detail in examples 2 to 6. In addition to 27C1, a large number of other antibodies were isolated with up to 7 of the 14 amino acids differing in CDR3 of the VH domain (FIG. 3). These had a similar preference for binding TGFβ1 compared to TGFβ2.

3. Identification and Characterisation of Antibodies to Human TGFβ-2 by Selection of Naive and Synthetic Phage Antibody Repertoires a. Induction of Phage Antibody Libraries Two different phage antibody repertoires were selected for antibodies to TGFβ2. The VH synthetic (Nissim et al., 1994) and tonsil (constructed as described earlier) repertoires were each treated as described for TGFβ1 to rescue phagemid particles.

b. Panning of Phage Antibody Library on TGFβ2

Phage induced from the two repertoires were each separately panned on TGFβ2 as described earlier for TGFβ1 but using 0.5 µg/ml TGFβ2 as the coating antigen.

c. Identification and Sequencing of TGFβ2-Specific ScFv Antibodies

Individual colonies from the third and fourth round selections were screened by both phage and soluble ELISA as described earlier for TGFβ1 but using flexible microtitre plates coated with TGFβ2 at 0.2 µg/ml rather than TGFβ1. Clones were chosen for further analysis if the ELISA signal generated on the TGFβ2-coated plate was at least double that on the uncoated plate. For the specificity ELISA, as described earlier for TGFβ1, clones were considered to be specific for TGFβ2 if the ELISA signal generated in the TGFβ2 coated well was at least five-fold greater than the signal on either TGFβ1, BSA or an uncoated well.

d. Sequence and Source of the Initial TGFβ2-Specific ScFv Antibodies

Different TGFβ2 specific antibodies were isolated from the selections using the two libraries described above. Each clone name, its origin and its heavy and light chain germline are given below. The complete sequence of 2A-H11 (SEQ ID NOS: 5, 6), 2A-A9 (SEQ ID NOS: 36, 37), Gold11-VH (SEQ ID NOS: 115, 116), Gold11-VL (SEQ ID NOS: 117, 118), 1-G2 (SEQ ID NOS: 119, 120) and 1-H6 (SEQ ID NOS: 121, 122) are given in FIG. 2(a).

| CLONE | LIBRARY SOURCE | VH GERMLINE | VL ISOTYPE |
|---|---|---|---|
| 1-G2 | Tonsil | | |
| 1-H6 | Tonsil | DP49 | |
| 2A-H11 | Synthetic VH | DP50 | VLambda |
| 2A-A9 | Synthetic | DP46 | VLambda |
| Gold-11 | Large scFv | | Vlambda |

Thus human antibodies binding to human TGFβ2 have been isolated from different sources, both natural Vgenes of unimmunised humans and synthetic libraries from cloned germline V genes together with synthetic CDRs.

4. Light Chain Shuffling of the TGFβ2-Specific ScFv Antibodies 2A-H11 and 2A-A9 a. Construction of Repertoires

The heavy chain of clones 2A-H11 and 2A-A9 were recombined with the complete repertoire of light chains derived from the PBL and large (tonsil-derived) scFv repertoires as described earlier for the TGFβ1-specific scFv antibody 1-B2. Both repertoires generated from the recombination with the PBL light chain repertoire were approximately $1 \times 10^5$, those generated from the recombination with the tonsil light chain repertoire were approximately $1 \times 10^6$.

b. Selection of Light Chain Shuffle Repertoires

The light chain-shuffle repertoires were selected for TGFβ2-specific antibodies using biotinylated TGFβ-2, as described earlier for the selection of the TGFβ1 light chain shuffle repertoires. For all of the first and second round selections, a concentrartion of 100 nM biotinylated TGFβ2 was used. For the third round selection of the PBL-derived light chain shuffle repertoire, biotinylated TGFβ2 was used at concentrations of 100 nM and 1 nM. For the third round selection of the tonsil-derived light chain shuffle repertoire, biotinylated TGFβ2 was used at a concentration of 50 nM.

c. Identification of TGFβ2-Specific ScFv Antibodies from Light Chain Shuffle Repertoires ScFv antibodies specific to TGFβ2 were identified by both phage and soluble ELISA, and sequenced, as described earlier. The sequences for identified TGFβ2-specific scFv antibodies are summarised below and the complete sequence of each clone is given in FIG. 2(b) (SEQ ID NOS: 38/39, 40/41, 42/43, 44/45, 46/47 and 123/124).

| CLONE | VL SOURCE | VH GERMLINE | VL ISOTYPE |
|---|---|---|---|
| 6-H1 | PBL | DP50 (2A-H11) | VKappa |
| 6-A5 | PBL | DP50 (2A-H11) | VLambda |
| 6-B1 | PBL | DP50 (2A-H11) | VLambda |
| 11-E6 | PBL | DP46 (2A-A9) | VKappa |
| 14-F12 | Tonsil | DP46 (2A-A9) | Vlambda | d. Specificity Determination by ELISA

Clones identified as binding TGFβ-2 rather an uncoated well, as described above, were further analysed for fine specificity. Specificity ELISA's were carried out using scFv either displayed on phage or in solution as described above, except that 5 ml of media in 50 ml Falcon tubes were inoculated with each clone and grown to generate the phage or soluble scFv used in the ELISA. Microtitre plate wells were coated with 50 µl of either 0.2 µg/ml TGFβ-1, 0.2 µg/ml TGFβ-2, 10 µg/ml bovine serum albumin (BSA) or PBS (the uncoated well). After preblocking both the phage (or soluble scFv) and the microtitre plates, 50 µl blocked phage (or soluble scFv) from each clone was added to a well coated with either TGFβ1, TGFβ2, BSA or an uncoated well. As above, alkaline phosphatse activity was visualised using either the chromagenic substrate pNPP (Sigma) or the Ampak system (Dako). Clones were considered to be specific for TGFβ2 if the ELISA signal generated in the TGFβ2 coated well was at least five-fold greater than the signal on either TGFβ1, BSA or an uncoated well. Cross-reactivity with unrelated antigens was determined more extensively for anti-TGFβ2 antibody in whole antibody format, see example 2. The cross-reactivity of 6B1 IgG4 and 6A5 IgG4 with TGFβ1 and TGFβ3 (obtained from R&D Systems, Abingdon) is also shown to be very low.

e. Specificity Determination by BIACore™

The antibodies were also shown to be specific for TGFβ2 compared to TGFβ1 by relative binding to the BIACore sensor chips coated with the appropriate antigen. TGFβ1 and TGFβ2 were immobilised by amine coupling to Biosensor CM5 sensorchips (Pharmacia) according to the manufacturers instructions. Single chain Fv fragments (35 μl; purified by immobilized metal affinity chromatography) were injected over the immobilized antigen at a flow rate of 5 μl/min. The amount of TGFβ bound was assessed as the total increase in resonance units (RUs) over this period. For the single chain Fv fragments 6H1, 6A5 and 14F12, these fragments gave a total of 686, 480 and 616 RUs respectively for the TGFβ1 coated sensor chip and 77, 71 and 115 RUs respectively for the TGFβ2 coated chip.

5. Building Higher Affinity Anti TGFβ1 Biological Neutralisers a. Recombining Heavy Chains Derived from High Affinity Anti-TGFβ1 scFv with Light Chains Derived from Anti-TGFβ1 and Anti-TGFβ2 scFv Showing Good Properties Antibodies derived by spiking CDR3 of the scFv antibody 1-B2 (section 2b) bind TGFβ1 with high affinity. To improve the chance of obtaining high affinity neutralising antibodies it was decided to chain shuffle VHs derived from high affinity anti-TGFβ1 scFv with VLs derived from scFv clones with promising properties and particularly with those capable of neutralising the activity of TGFβ2 in vitro.

Heavy chains were amplified by PCR from the repertoire of CDR3 spiked 1-B2 clones after selection on TGFβ1 (section 2a.ii) using the primers pUC19reverse and PCR-H-Link (Table 1). Amplification conditions consisted of 30 cycles of 94° C. for 1 min, 55° C. for 1 min and 72° C. for 1 min, followed by 10 min at 72° C. The PCR product was separated through a 1% agarose-TAE gel, the band representing the amplified VH excised, and eluted from the agarose gel using the Geneclean Kit (Bio 101).

Light chains were separately amplified by PCR from each of the anti TGFβ1 specific neutralisers (7-A3, 10-A6 and 14-A1; section 2a.iii) and each of the anti TGFβ2 specific neutralisers (6H1, 6A5, 6B1, 11E6 and 14F12; section 4c) using the primers fdtetseq1 and PCR-L-Link (Table 1). The same PCR conditions were used as described for the VH amplification. Each VL PCR product was then separately purified through a 1% agarose-TAE gel as described above. Purified products were finally mixed in approximately equimolar amounts (as estimated from an analytical agarose gel) to provide a VL 'pool'.

Approximately 50 ng amplified heavy chains and 50 ng of amplified pooled light chains were combined and precipitated with sodium acetate and ethanol using 25 μg glycogen as a carrier. The precipitated DNA was pelleted by centrifugation at 13, 000 rpm in a microfuge, air dried and resuspended in 23 μl H20. This was used in an assembly amplification after the addition of reaction buffer, dNTP's to 200 nM and 5 units Taq polymerase. Amplification conditions consisted of 20 cycles of 94° C. for 1 min, 55° C. for 1 min and 72° C. for 2 mins, followed by 10 min at 72° C. 5 μl of assembly was used as the template in a 50 ul 'pull-through' amplification with the primers fdtetseq and pUC19reverse. Amplification conditions consisted of 30 cycles of 94° C. for 1 min, 55° C. for 1 min and 72° C. for 2 mins, followed by 10 min at 72° C.

The pull-through amplification product was separated through 1% agarose-TAE and the band representing the pull-through VH-VL excised and eluted using the Geneclean Kit. This was digested with the restriction endonucleases SfiI and NotI (NEB) and ligated into the phagemid vector pcantab 6 (McCafferty et al. 1994 supra), previously digested with Sfi 1 and NotI, using the Amersham ligation system. The ligation product was used to transform electro-competent TG1 cells, plated out on 2YTAG plates and incubated overnight at 30° C. A repertoire of approximately $3\times10^6$ individual clones was generated.

b. Selection of Chain Shuffled Repertoire

The chain shuffled repertoire was selected by a single round of panning on TGFβ1 (1 ug/ml), as previously described (section 1b).

c. Identification of TGFβ1 Specific scFv Antibodies

ScFv antibodies specific to TGFβ1 were identified by phage ELISA and sequenced as described earlier (sections 1d.i and 1e). New TGFβ1 specific scFv antibodies were identified. Five new high affinity clones were isolated—CS32 which comprises 31G9 VH (SEQ ID NO: 10) and 7A3 VL (SEQ ID NO: 16); CS39 which comprises 31G9 VH (SEQ ID NO: 10) and 6H1 VL (SEQ ID NO: 39); CS37 which comprises 31G9 VH (SEQ ID NO: 10) and 11E6 VL (SEQ ID NO: 45) with an Ile for Val substitution at residue 2 (VL sequence given in FIG. 14; SEQ ID NO: 57); CS35 which comprises 31G9 heavy chain (SEQ ID NO: 10) with substitutions of Glu for Gln at residue 1, Gln for Glu at residue 5 and 14F12 VL (SEQ ID NO: 47); and CS38 which comprises 31G9 VH (SEQ ID NO: 10) with substitutions of Thr for Gln at residue 3, Glu for Gln at residue 5, Leu for Phe at residue 27, Ile for Asn at residue 56 and Arg for Gln at residue 105 and 6A5 VL (SEQ ID NO: 41).

d. Off-rate Determination for Single Chain Fv Fragments Binding to TGFβ1 and TGFβ2

The off-rates for binding to TGFβ1 or TGFβ2 of the single chain Fv fragments described in this example were determined as described by Karlsson et al (R. Karlsson et al, J. Immunol. Methods 145, 229-240, 1991). The results obtained are shown in Table 2, together with dissociation constants for those which have been determined. These results indicate that high affinity antibodies have been isolated.

6. Identification and Characterisation of an Antibody which Cross-Reacts with both Human TGFβ1 and TGFβ2 but not TGFβ3 by Selection of a Large ScFv Repertoire a. Panning of the Library and Identification of Binders The large scFv library (described earlier) was induced, phagemid particles rescued and panned as described earlier with the following modifications. For the first round of panning, $10^{12}$ tu library phage in 0.5 ml PBS were used (rather than the standard 2 ml), for the second round, $3.5\times10^9$ phage in 0.5 ml PBS were used. The immuno tube was coated with 10 μg TGFβ2 in 0.5 ml PBS for both the first and second round of selection. Individual colonies from the second selection were screened by ELISA using 0.2 μg/ml TGFβ1. Clones binding TGFβ1 were further screened on TGFβ2, TGFβ3, BSA and PBS. Clones were considered to be specific for both TGFβ1 and TGFβ2 if the ELISA signal generated in the TGFβ1 and the TGFβ2 coated wells were both at least five-fold greater than the signal on TGFβ3, BSA and an uncoated well.

c. Identification of a TGFβ1/TGFβ2 Cross-Reactive ScFv Antibody A single scFv antibody specific for both TGFβ1 and TGFβ2 was identified by both phage and soluble ELISA, and sequenced, as described earlier. The complete sequence of the VL domain of the antibody gene VT37 is given in FIG. 4 (SEQ ID NO: 48). The dissociation constant of this single chain Fv antibody was estimated by analysis using BIACore™ to be 4 nM for TGFβ1 and 7 nM for TGFβ2. Cross-reactivity for TGFβ3 was also determined. Purified VT37scFv at 8.3 µg/ml was passed over BIACore™ sensor chips coated with TGFβ1 (500RUs coated); TGFβ2 (450RUs coated) or TGFβ3 (5500RUs coated). The relative response for VT37 scFv binding was: TGFβ1-391RU bound; TGFβ2-261RU bound or TGFβ3-24RU bound. Thus this antibody binds strongly to TGFβ1 and TGFβ2 but binding to TGFβ3 is not detectable above background.

EXAMPLE 2

Construction of Cell Lines Expressing Whole Antibodies

For the construction of cell lines expressing IgG4 antibodies, variable domains were cloned into vectors expressing the human gamma 4 constant region for the VH domains or the human kappa or lambda constant regions for the VL domains.

To construct the whole antibody, 27C1/10A6 IgG4 (specific for TGFβ1), 27C1 VH DNA was prepared from the clone isolated above, in example 1. The VH gene was amplified by PCR using the oligonucleotides VH3BackSfiEu and VHJH6ForBam (Table 1) with cycles of 1 min at 94° C., 1 min at 55° C., 1.5 min at 72° C. Following digestion with SfiI and BamHI, the VH gene was cloned into the vector vhcassette2 (FIG. 5) digested with SfiI and BamHI. Ligated DNA was transformed into *E. coli* TG1. Ampicillin resistant colonies were obtained and those containing the correct insert identified by DNA sequencing.

Plasmid DNA from these colonies was prepared and the DNA digested with HindIII and BamHI. The HindIII-BamHI restriction fragment was ligated into the human IgG4 heavy chain expression vector pG4D100 (FIG. 6), which had been digested with HindIII and BamHI and the DNA transfected into *E. coli* TG1 by electroporation. The sequence of the VH gene insert was again verified by DNA sequencing.

For the light chain, the VL gene of 10A6, isolated in example 1, was first mutagenized to remove its internal BamHI site using site directed mutagenesis (Amersham RPN1523) with the oligonucleotide DeltaBamHI (SEQ ID NO: 89) (Table 1). The resulting VLDBamH1 gene was amplified by PCR using the oligonucleotides Vλ3/4Back-EuApa (SEQ ID NO: 90) and HuJλ2-3ForEuBam (SEQ ID NO: 91) (Table 1). Following digestion of the amplified insert with ApaLI and BamHI, the VL gene was cloned into the vector vlcassetteCAT1 (FIG. 7) digested with ApaLI and BamHI. Ligated DNA was transformed into *E. coli* TG1. Ampicillin resistant colonies were obtained and those containing the correct insert were identified by DNA sequencing.

Figure 8:
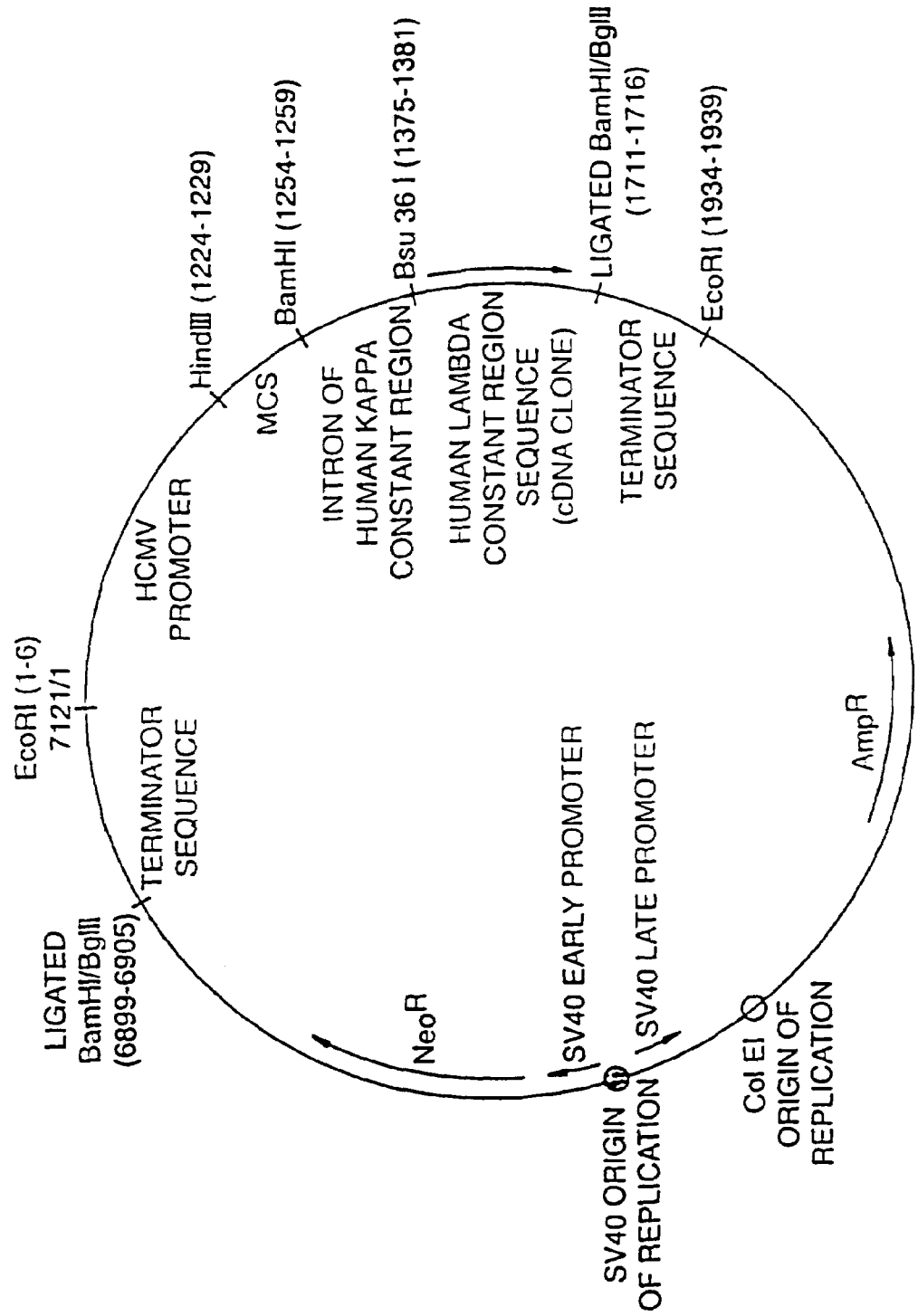
FIG. 8 shows a map of the vector pLN10 (not to scale). Multiple cloning site (MCS): 5'-HindIII-(SphI)-(PstI)-SalI-XbaI-BamHI-3' (1224-1259. Restriction sites shown in brackets are not unique.

Plasmid DNA from these colonies was prepared and the DNA digested with Hind III and BamHI. The HindIII-BamHI restriction fragment containing the leader sequence and the VL domain was ligated into the human lambda light chain expression vector, pLN10 (FIG. 8), which had been digested with HindIII and BamHI. Following electroporation, transformants in *E. coli* were checked by DNA sequencing.

Plasmid DNA was prepared from the pG4D100-27C1 clone and the pLN10-10A6 clone. This DNA was then co-transfected into DUKXB11 Chinese Hamster Ovary (CHO) cells by electroporation (290V; 960 µF). The cells were then grown for 2 days in non-selective medium (alpha-MEM plus nucleosides). Cells were then transferred to a selective medium (alpha-MEM plus 1 mg/ml G418 without nucleosides) and grown in 96 well plates. Colonies were then transferred to 24 well plates and samples assayed by sandwich ELISA for assembled human IgG4 antibody and by binding to TGFβ1 in ELISA (as in example 1). For the sandwich ELISA, goat anti-human IgG coated on to the ELISA plate and captured human IgG4 detected using goat antihuman lambda light chain alkaline phosphatase conjugate. High expressing cell lines were then derived by amplification of the inserted genes using selection in the presence of methotrexate (R. J. Kaufman Methods Enzymol. 185 537-566, 1990).

Figure 9:
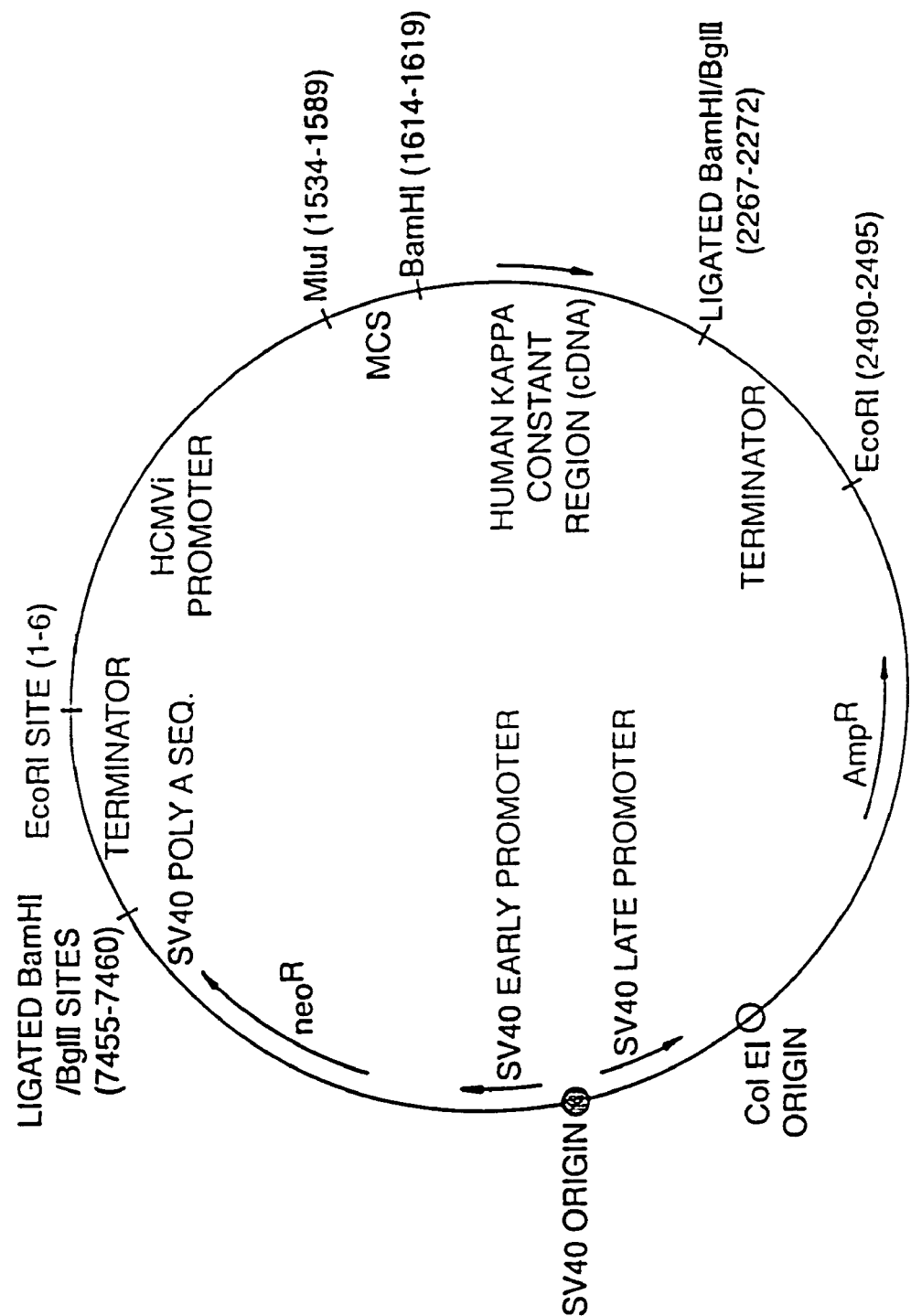
FIG. 9 shows a map of the vector pKN100 (not to scale). Multiple cloning site (MCS): 5'-MluI-(AvaI)-HindIII-(SphI)-(PstI)-SalI-XbaI-BamHI-3'. Restriction sites shown in brackets are not unique.

The whole antibody 6H1 IgG4 (specific for TGFβ2) was constructed in a similar way to the above construction of 27C1/10A6 IgG4. The 6H1 VH gene (example 2) was cloned into pG4D100 as for 27C1 above except that PCR amplification was performed with the oligonucleotides VH3BackSfiEu (SEQ ID NO: 87) and VHJH1-2FORBam (SEQ ID NO: 92). The 6H1 VL gene (example 2) was subcloned into vlcassetteCAT1 as above except that PCR amplification was performed with the oligonucleotides Vk2BackEuApa (SEQ ID NO: 93) and HuJk3FOREuBam (SEQ ID NO: 94). However, since the 6H1 VL is a kappa light chain the HindIII-BamHI fragment was subcloned into the human kappa light chain expression vector pKN100 (FIG. 9) which had been digested with HindIII and BamHI. High expressing cell lines were then isolated as described above. Clones expressing antibody were identified from culture plates by sandwich ELISA for assembled human IgG4 antibody (detected using goat anti-human kappa light chain conjugate and by binding to TGFβ2 in ELISA (as in example 2).

To construct the whole antibodies 6A5 IgG4 and 6B1 IgG4, the same 6H1 VH construct in pG4D100 was used as for 6H1IgG4 since these antibodies all have the same VH gene. The 6B1 and 6A5 genes were each subcloned into vlcassetteCAT1 as above for the 10A6 light chain except that PCR amplification was performed with the nucleotides Vλ3backEuApa (SEQ ID NO: 95) and HuJλ2-3ForEuBam (SEQ ID NO: 91). The HindIII-BamHI restriction fragment was then subcloned into pLN10 as above. Clones expressing antibody were identified from culture plates by sandwich ELISA for assembled human IgG4 antibody (detected using goat anti-human kappa light chain conjugate and by binding to TGFβ2 in ELISA (as in example 2).

Properties of Whole Antibody Constructs

Purification of Whole Antibodies

Serum-free supernatant from CHO cells producing the relevant IgG was clarified by centrifugation at 8000 rpm (Beckman JS2-21) prior to purification. The supernatant was applied to a HiTrap Protein A Sepharose prepacked affinity column from Pharmacia, either 1 or 5 ml size, with binding capacities of 25 or 120 mg respectively. Each IgG had a dedicated column to avoid any potential carry over of material from one purification to another. The column was equilibrated to phosphate buffered saline (PBS) with ten column volumes of 1×PBS prior to applying the supernatant. When all the supernatant had been applied to the column at a flow rate of 2-4 ml/minute, again, depending on the column size, the column was washed with ten column volumes of 1×PBS to remove any non-specifically bound material. Elution of the bound protein was achieved using 0.1M sodium acetate, adjusted to pH 3.3 with glacial acetic acid. The eluted material was collected in 8 fractions of 1.5 ml volume, and the amount of protein determined by measuring the absorbance at 280 nm, and multiplying this value by 0.7 to get a value in mg/ml. This was then neutralised with 0.5 ml of 1M Tris.HCl pH 9.0 per 1.5 ml fraction, and the protein-containing fractions pooled and dialysed against 1×PBS to buffer exchange the IgG. The column was returned to neutral pH by running ten column volumes of 1×PBS through, and was stored in 20% ethanol as a preservative until required again.

A sample was then run on 10-15% SDS-PAGE (Phast system, Pharmacia) and silver stained. This allowed an assessment of the purity of the IgG preparation. This was usually found to be about 80-90%, with only a couple of other bands prominent on the stained gel.

Binding Specificity by ELISA

Figure 13:
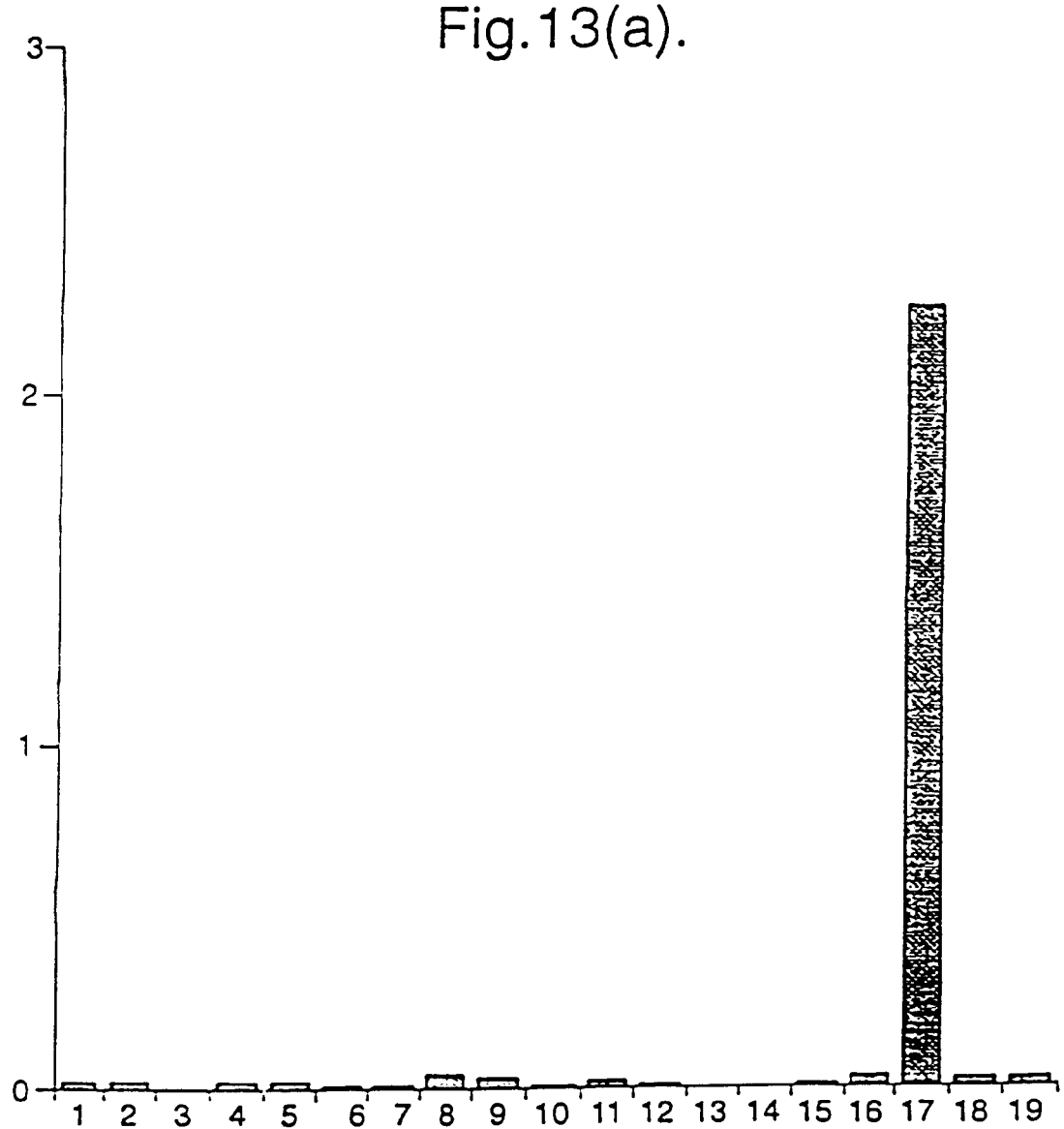
FIG. 13 shows the results of an ELISA to measure the cross-reactivity of the antibodies 6B1 IgG4 and 6A5 IgG4 with TGFβ isoforms and non-specific antigens.
Figure 14:
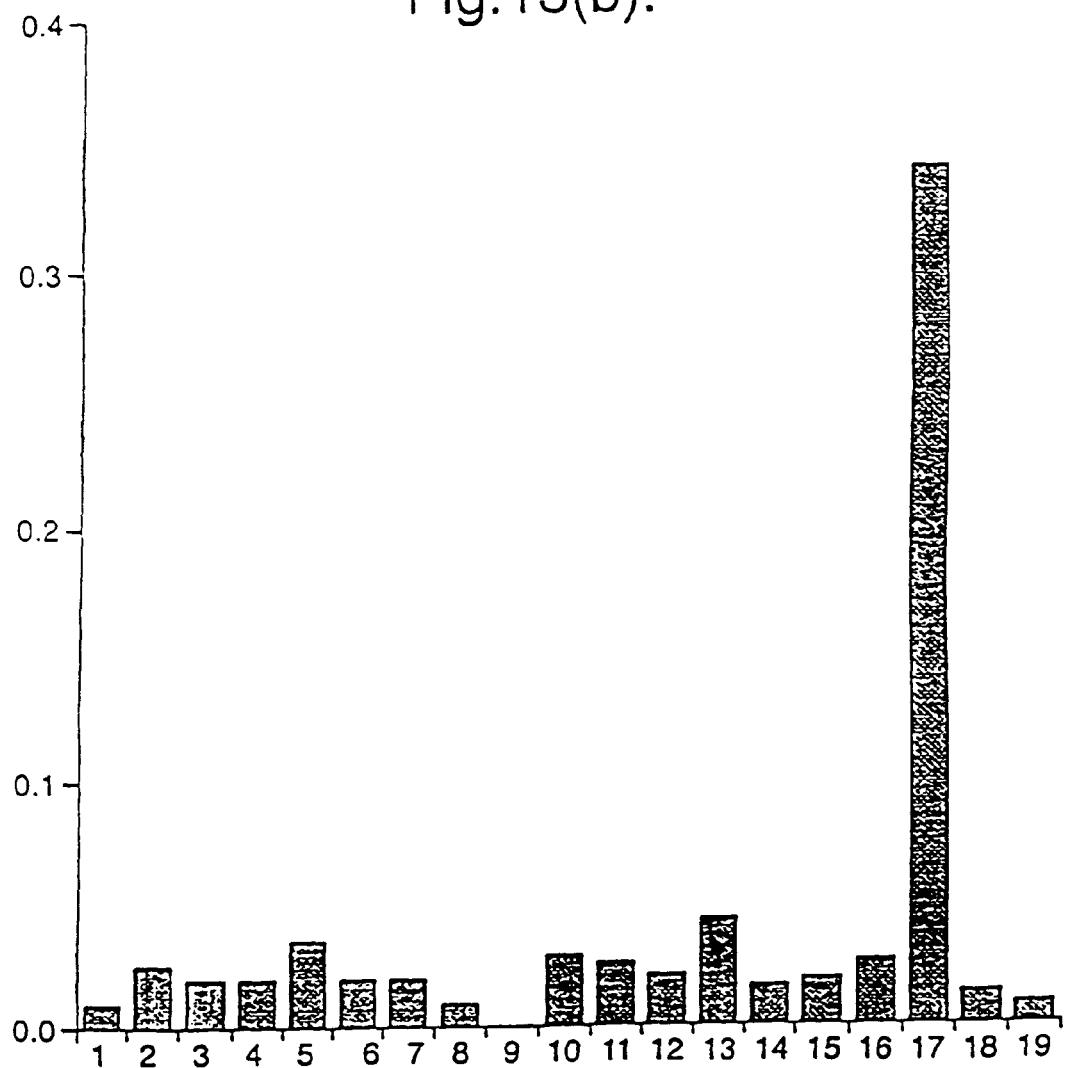
FIG. 14 shows the amino acid and encoding nucleic acid sequence for the VL domain of the TGFβ1-specific antibody CS37 (SEQ ID NOS: 58, 59).

The IgG4 antibodies 6B1 and 6A5 were shown to bind TGFβ2 with very low cross-reactivity to TGFβ1 and TGFβ3 and no detectable cross-reactivity with a range of non-specific antigens: interleukin-1; human lymphotoxin (TNFβ); human insulin; human serum albumin; single stranded DNA; oxazolone-bovine serum albumin; keyhole limpet haemocyanin; chicken egg white trypsin inhibitor; chymotrypsinogen; cytochrome c; glyceraldehyde phosphate dehydrogenase; ovalbumin; hen egg lysozyme; bovine serum albumin and tumour necrosis factor a—(TNFα) (FIGS. 13(a) and (b)). Likewise the antibodies 6B1, 6A5 and 6H1 IgG4 bound strongly to TGFβ2 coated on a BIACore™ sensor chip but not significantly to TGFβ1 or TGFβ3 coated chips.

Binding Properties of Whole Antibodies by BIACore™

The affinity constants of the above antibodies were determined by BIACore™, using the method of Karlsson et al. J. Immunol. Methods 145, 299-240, 1991 (supra) and found to be approximately 5 nM for 27C1/10A6 IgG4 for TGFβ1 and 2 nM for 6H1 IgG4 for TGFβ2. The antibody 27C1/10A6 IgG4 also shows some cross-reactivity with TGFβ2 coated onto Biosensor chips but the dissociation constant is approximately 10 fold or more higher for TGFβ2 compared to TGFβ1. There was no significant cross-reactivity with lysozyme coated onto a BIACore™ sensor chip. Neutralisation and inhibition of radioreceptor binding by IgG4 antibodies to TGFβ1 and TGFβ2 is described in examples 3 and 4.

EXAMPLE 3

Neutralisation by Antibodies of the Inhibitory Effect of TGFβ1 and TGFβ2 on Cell Proliferation The neutralising activity of the antibodies described in examples 1 and 2 were tested in a modification of a bioassay for TGFβ as described by Randall et al. (1993) J. Immunol Methods 164, 61-67. This assay is based on the ability of TGFβ1 and TGFβ2 to inhibit the interleukin-5 induced proliferation of the erythroleukaemia cell line, TF1 and being able to reverse this inhibition with specific TGFβ antibodies.

Method

Cells and Maintenance

The human erythroleukaemia cell line TF1 was grown in RPMI 1640 medium supplemented with 5% foetal calf serum, penicillin/streptomycin and 2 ng/ml rhGM-CSF in a humidified incubator containing 5% $CO_2$ at 37° C. Cultures were passaged when they reached a density of $2\times10^5$/ml and diluted to a density of $5\times10^5$/ml.

Cytokines and Antibodies rhGM-CSF and rhIL-5 were obtained from R&D systems, rhTGFβ2 was obtained AMS Biotechnology. Rabbit anti TGFβ2 antibody was from R&D Systems and Mouse anti-TGFβ1, 2, 3 was from Genzyme. Other antibodies against TGFβ2 were as described in examples 1&2.

Titration of Inhibition of Proliferation by TGFβ2

Doubling dilutions of TGFβ2 (800 pM-25 pM) for the construction of a dose response curve were prepared on a sterile microtitre plate in 100 μl of RPMI 1640 medium containing 5% foetal calf serum and antibiotics. All dilutions were performed at least in quadruplicate. Additional wells containing 100 μl of the above medium for reagent and cells only controls were also included.

TF1 cells were washed twice in serum free RPMI 1640 medium and resuspended in RPMI 1640 medium supplemented with 5% foetal calf serum, 100 U/ml penicillin and 100 μg/ml streptomycin and 4 ng/ml rhIL-5 at a density of $2.5\times10^5$/ml. Aliquots of 100 μl were added to the previously prepared dilution series and the plate incubated for 48 hr. in a humidified incubator containing 5% $CO_2$ at 37° C.

Cell proliferation was measured colourimetrically by addition of 40 μl CellTiter96 substrate (Promega), returning the plate to the incubator for a further 4 hr and finally determining the absorbance at 490 nm. The percentage inhibition for each concentration of TGFβ2 as compared to cell only wells was then calculated.

Assay for Neutralisation of TGFβ2 Inhibitory Activity by Anti-TGFβ2 Antibodies

Neutralisation of TGFβ2 was determined by making doubling dilutions in of each purified antibody in 100 μl of medium as above. TGFβ2 was added to each antibody dilution to give a final concentration equivalent to that which gave 50% inhibition in the titration described above. Each dilution was prepared in quadruplicate. Additional wells were prepared for antibody only, cells only and reagent controls. Cell preparation and determination of cell proliferation was performed as described above.

Results

TGFβ2 was shown to inhibit the proliferation of TF1 cells by 50% at a concentration of 50 pM. This concentration was used for all neutralisation experiments.

Figure 10:
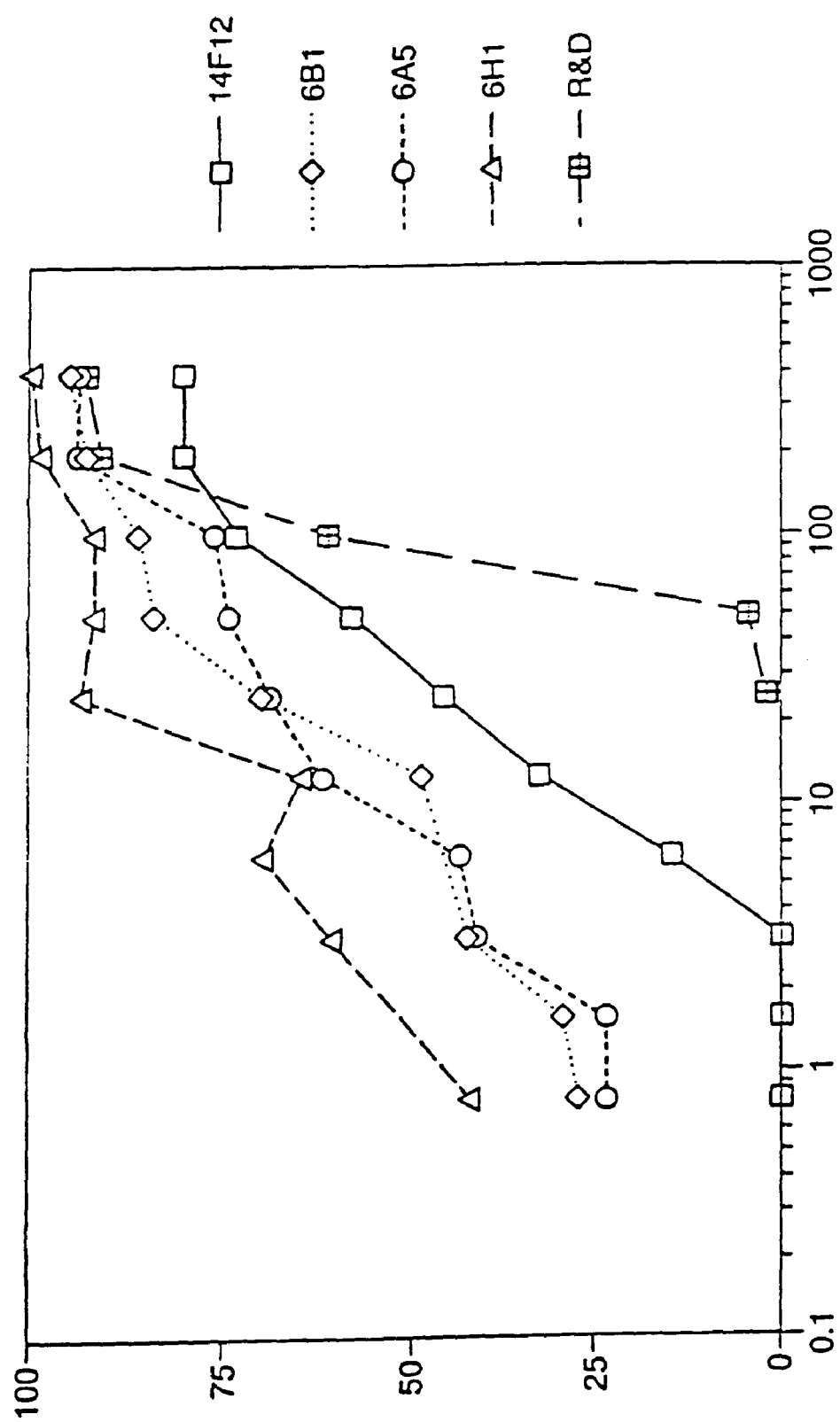
FIG. 10 shows the % neutralisation of TGFβ2 activity by single chain Fv antibodies in an assay using proliferation of the erythroleukaemia cell line, TF1 at different nM concentrations of scFv.
Figure 11:
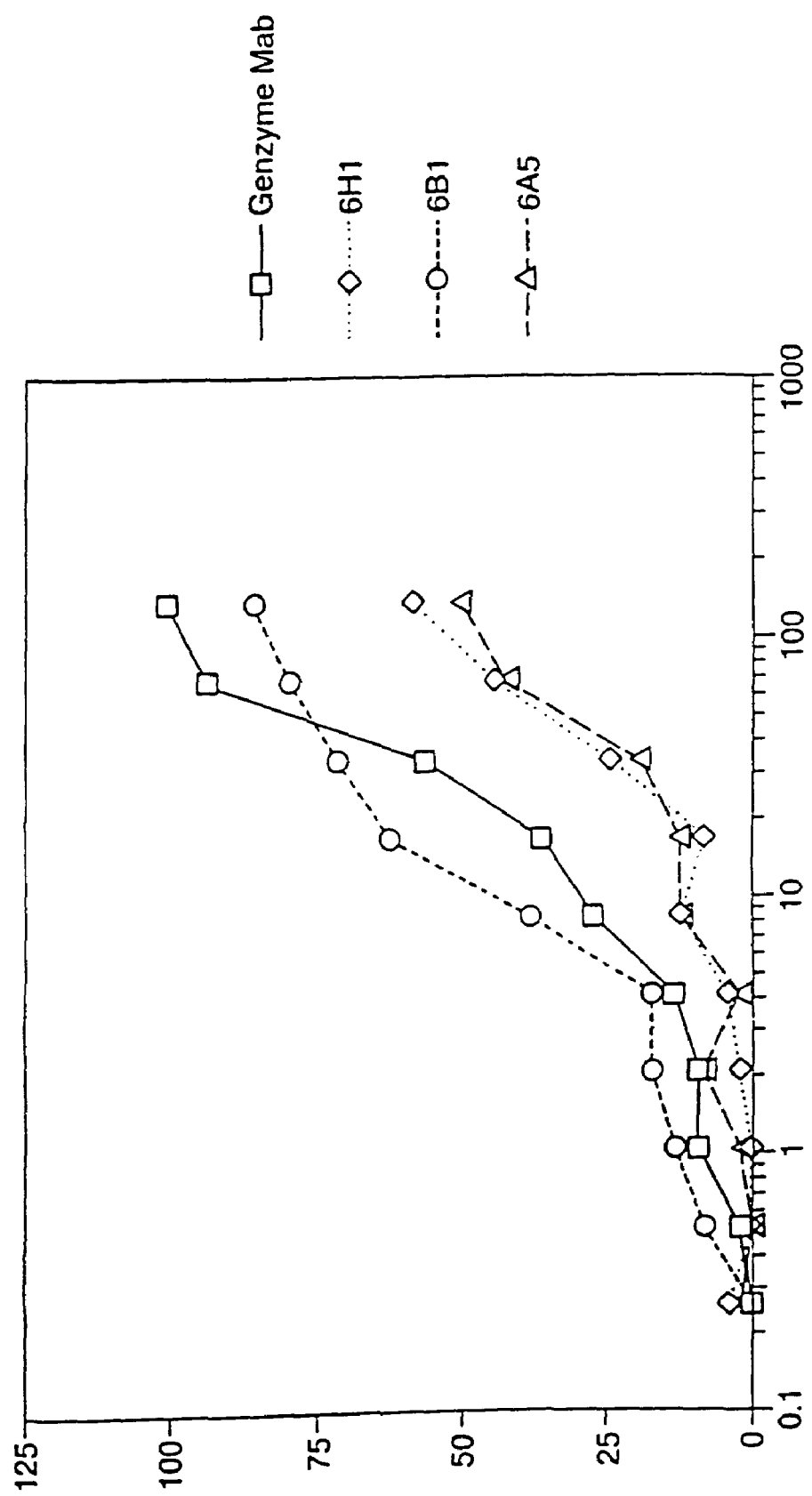
FIG. 11 shows the neutralisation of TGFβ2 activity by whole IgG4 antibodies in an assay using proliferation of the erythroleukaemia cell line TF1 at different nM concentrations of antibody.

These assays showed that TGFβ2 activity was neutralised in a dose dependant manner for both scFv fragments (FIG. 10) and for whole IgG4 antibodies (FIG. 11). The concentration of antibody which gave 50% inhibition was determined from the graphs and is shown in Table 4.

EXAMPLE 4

Inhibition by Antibodies of TGFβ Binding to Receptors Measured in A Radioreceptor Assay Single chain Fv fragments and whole IgG4 antibodies from different clones were expressed and purified and their ability to inhibit binding of TGFβ to receptors measured in a radioreceptor assay.

Purification of scFv

ScFvs containing a poly histidine tail are purified by immobilised metal affinity chromatography. The bacterial clone containing the appropriate plasmid is inoculated into 50 ml 2TY medium containing 2% glucose and 100 µg/ml ampicillin (2TYAG) and grown overnight at 30° C. The next day the culture is added to 500 ml prewarmed 2TYAG and grown at 30° C. for 1 h. The cells are collected by centrifugation and added to 500 ml 2TY containing ampicillin and 1 mM IPTG and grown at 30° C. for 4 h. The cells are then collected by centrifugation and are resuspended in 30 ml ice-cold 50 mM Tris HCl pH 8.0, 20% (w/v) sucrose, 1 mM EDTA. After 15 min end-to-end mixing at 4° C. the mixture is centrifuged at 12 k rpm for 15 min at 4° C. The supernatant is removed and to it added~1 ml NTA-agarose (Qiagen 30210) and mixed at 4° C. for 30 min. The agarose beads are washed extensively with 50 mM sodium phosphate, 300 mM NaCl and loaded into a small column. After further washing with 50 mM sodium phosphate, 300 mM NaCl, 10 mM imidazole pH 7.4 scFv is eluted with 50 mM sodium phosphate, 300 mM NaCl, 250 mM imidazole pH 7.4. 0.5 ml fractions are collected and the protein containing fractions identified by measuring the $A_{280nm}$. Pooled fractions are concentrated and scFv further purified by gel filtration in PBS on a Superdex 75 column (Pharmacia).

Purification of Whole Antibodies

Whole IgG4 antibodies were purified as described in Example 2.

Radioreceptor Assay for TGFβ

Neutralisation of TGFβ activity is measured by the ability of the scFvs and IgGs to inhibit the binding of $^{125}$-I labelled TGFβ to its receptors on A549 human lung carcinoma cells.

A549 cells (ATCC CCL 185) are grown in high glucose Dulbecco's modified Eagle's medium (Sigma D-6546) supplemented with 10% foetal calf serum (PAA), 2 mM glutamine (Sigma G-7513), penicillin/streptomycin (Sigma P-0781), MEM non-essential amino acids (Sigma M-7145).

Cells are seeded at 1-2×105 cells/ml/well into the wells of 24-well cluster plates and grown for 24 h in serum-free DMEM. Cell monlayers are washed twice with serum-free DMEM and 0.5 ml binding medium (DMEM/Hams F12 (Sigma D-6421) containing 0.1% (v/v) BSA added to each well.

Aliqouts of $^{125}$I-TGFβ1 or TGFβ2 (70-90 TBq/mmol; Amersham International) at 20 pM are preincubated with antibody in binding medium at room temperature for 1 h. Duplicate samples of 0.5 ml of TGFβ/antibody mixtures are then added to the cell monlayers and are incubated at 37° C. for 1-2 h. Control wells contain TGFβ only. Unbound TGFβ is removed by washing 4 times with Hank's balanced salt solution containing 0.1% BSA. Cells are solubilised in 0.8 ml 25 mM Tris HCl pH 7.5, 10% glycerol, 1% Triton X-100 at room temperature for 20 min. The contents of each well are removed and $^{125}$I measured in a gamma counter. The potency of each scFv or IgG is measured by the concentration of antibody combining sites necessary to inhibit binding of TGFβ by 50% (IC50; Table 5). Thus the IC50 values are below 10 nM and in some cases below 1 nM indicating very potent antibodies.

EXAMPLE 5

Prevention of Scar Formation by Antibodies Against TGFpβ1 and TGFβ2 in the Injured Central Nervous System of the Rat Logan et al. (1994) Eur. 3 Neuroscience 6, 355-363 showed in a rat model of CNS injury, the ameliorating effect of a neutralising turkey antiserum directed against TGFβ1 on the deposition of fibrous scar tissue and the formation of a limiting glial membrane that borders the lesion. A study was set up to investigate the effects of neutralising engineered human antibodies directed against both TGFβ1 and TGFβ2 in the same rat model. The derivation of the antibodies used in this study is described in examples 1 and 2.

Method

Animals and Surgery

Groups of five female Sprague-Dawley rats (250 g) were anaesthetised with an i.p. injection. The anaesthetised rats had a stereotactically defined lesion made into the right occipital cortex (Logan et al 1992 Brain Res. 587, P216-227) and the lateral ventricle was surgically cannulated and exteriorised at the same time (Logan et al 1994 supra).

Neutralisation of TGFβ

Animals were intraventricularly injected daily with 5 ul of purified anti TGFβ antibodies (Table 3) diluted in a vehicle of artificial cerebrospinal fluid as described by Logan et al 1994 supra. Fourteen days post lesion all animals were perfusion fixed and 7 mm polyester wax sections were processed for histochemical evaluation of the lesion site by immunofluorescent staining.

Fluorescent Immunohistochemistry and Image Analysis

Morphological changes within the wound site were followed by immunofluorescent staining with antibodies to fibronectin and laminin detected with anti-species FITC conjugates (Logan et al 1994 supra). These changes were semi-quantitatively assessed by image analysis using a Leitz confocal microscope linked to a Biorad MRC500 laser scanning system. Readings were taken at standard positions mid-way along the lesion.

Results

Effects of Antibodies to TGFβ at the Site of CNS Injury

Quantitation of the specific relative fluorescence for each of the antibodies is shown in FIGS. 12a and b. Laminin is a measure of the formation of the glial limitans externa along the boundaries of the wound and together with fibronectin forms a matrix of fibrous tissue within the centre of the wound. Quantitation by image analysis of these two proteins allows the degree of scarring at the wound site to be determined.

Compared with the saline control (FIG. 12a, b), There is a considerable decrease in fibronectin and laminin immuno-localisation in the wound in the anti-TGFβ antibody treated brains. Thus this indicates that these engineered human antibodies directed against epitopes on TGFβ1 & TGFβ2 ameliorate the effects of injury to the CNS both separately and together by preventing the deposition of the cellular matrix proteins fibronectin and laminin within the wound site. Previously Logan et al (1994 supra) had shown the effectiveness of a polyclonal turkey anti-sera directed against TGFβ1. This is the first report of any antibodies directed against TGFβ2 having been shown to be effective in this model.

EXAMPLE 6

Determination of Binding of 6B1 IgG4 to Active or Latent Form of TGFβ2

TGFβ2 is synthesised and secreted exclusively as a biologically inactive or latent complex (Pircher et al, (1986) Biochem. Biophys Res. Commun. 158, 30-37).

The latent complex consists of TGFβ2 disulphide linked homodimer non-covalently associated with latency-associated peptide (LAP). Activation of TGFβ2 occurs when it is released from it processed precursor. Active TGFβ2 is capable of reversibly dissociating and reassociating with the LAP, which results in the turning on and off of its bioactivity respectively.

Cultured PC-3 adenocarcinoma cells (Ikeda et al (1987) Biochemistry 26, 2406-2410) have been shown to secrete almost exclusively latent TGFβ2 providing a convenient source for determination of binding to the active or latent form of TGFβ2 by the antibody 6B1 IgG4.

Method

Cell Culture

PC-3 prostatic adenocarcinoma cells were grown to confluence in supplemented with 10% FBS. The cells were washed 3× with PBS and cells cultured for a further 7 days in serum free Hams F12/DMEM supplemented with 1.4× $10^{-5}$ M tamoxifen (Brown et al, (1990) Growth Factors 3, 35-43). The medium was removed, clarified by centrifugation and divided into two 15 ml aliquots. One aliquot was acidified for 15 min with 5M HCl by adding dropwise until the pH=3.5 and then neutralised by the similar addition of 5M NaOH/1M HEPES pH7.4. This procedure activates the latent TGFβ2 quantitatively.

Competition ELISA

Sixteen wells of ELISA plate were coated overnight with 100 μl 200 ng/ml TGFβ2 in PBS at 4° C. The plate was washed 3× with PBS tween and blocked at 37° C. with 200 μl of 3% Marvel in PBS.

The following samples were incubated at room temperature for 1 hour.

400 μl Hams F12/DMEM (reagent blank)

400 μl Hams F12/DMEM plus 4 μg 6B1 IgG4 antibody (positive control)

400 μl PC 3 acid activated conditioned media plus 4 μg 6B1 IgG4 antibody (active TGFβ2 sample)

400 μl PC 3 untreated conditioned media plus 4 μg 6B1 IgG4 antibody (latent TGFβ2 sample).

The ELISA plate was emptied of blocking solution and 100 μl of one of the above solutions added to sensitised wells in quadruplicate and incubated at room temperature for 2 hours. The plate was washed 3× with PBS/Tween and wells refilled with 100 μl of goat anti-human IgG γ chain alkaline phosphatase conjugate diluted 1:5000 in 1% Marvel/PBS. After 1 hour the wells were washed 3× with PBS/Tween and bound antibody was revealed with p-NPP substrate by absorbance at 405 nm.

Results

Figure 23:
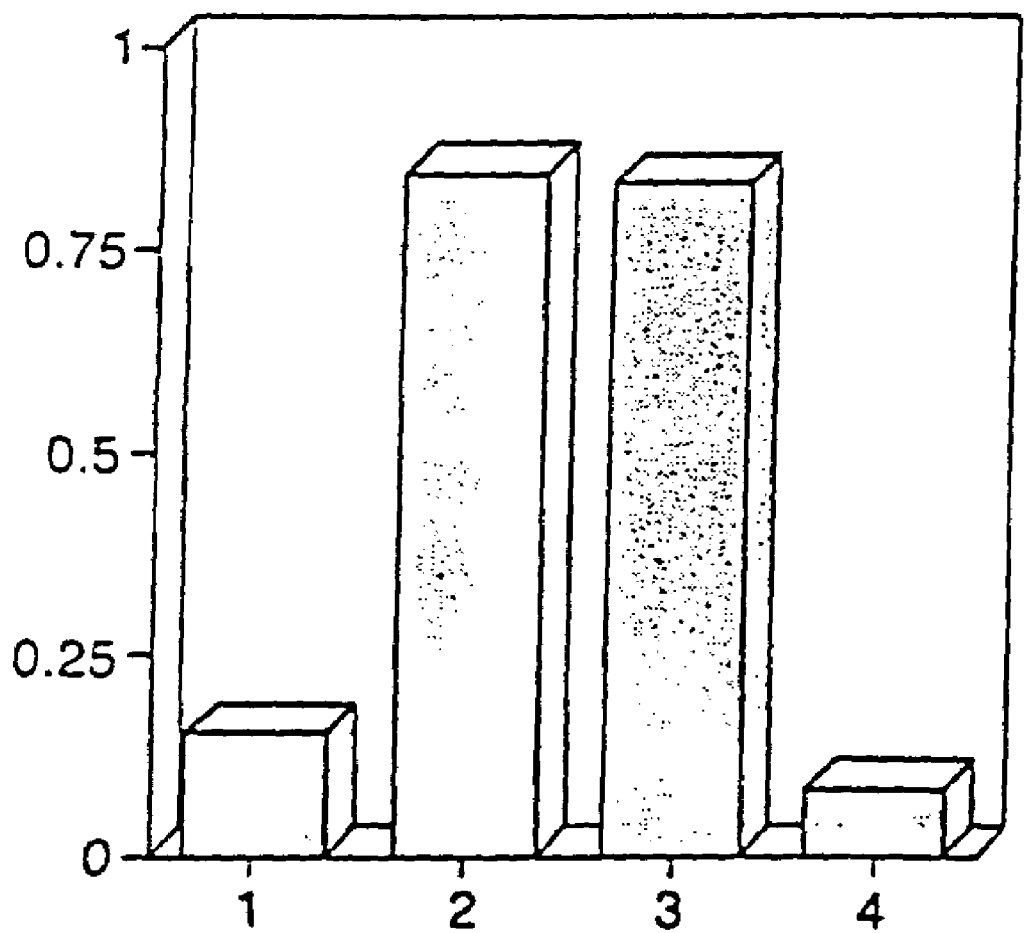
FIG. 23 shows the results of competition ELISA experiments described in Example 6. Following overnight incubation with TGFβ2, plates were treated with the following solutions 1-4 (number corresponding to those in Figure): 1-400 µl Hams F12/DMEM (reagent blank), 2-400 µl Hams F12/DMEM plus 4 µg 6B1 IgG4 antibody (positive control), 3-400 µl PC3 untreated conditioned media plus 4 µg 6B1 IgG4 antibody (latent TGFβ$_2$ sample), 4-400 µl PC3 acid activated conditioned media plus 4 µg 6B1 IgG4 antibody (active TGFβ$_2$ sample).

The results of this experiment are shown in FIG. 23.

This result clearly shows that pre-incubation with activated TGFβ2 inhibits binding of 6B1 to TGFβ2 bound onto an ELISA plate, whereas the latent form does not. This proves that 6B1 IgG4 only binds to the active form of TGFβ2.

EXAMPLE 7

Neutralisation by Antibodies Directed Against TGFβ2 of the Inhibitory Effect of TGFβ Isoforms on Cell Proliferation The neutralising activity of 6B1 IgG4, 6H1 IgG4 (purified as in example 2) and a mouse monoclonal antibody (Genzyme; J. R. Dasch et al., supra) was measured for each of the TGFβ isoforms, TGFβ1, TGFβ2 and TGFβ3 in the TF1 cell proliferation assay described in Example 3. The concentration of TGFβ isoform was 100 pM in each assay.

Figure 16:
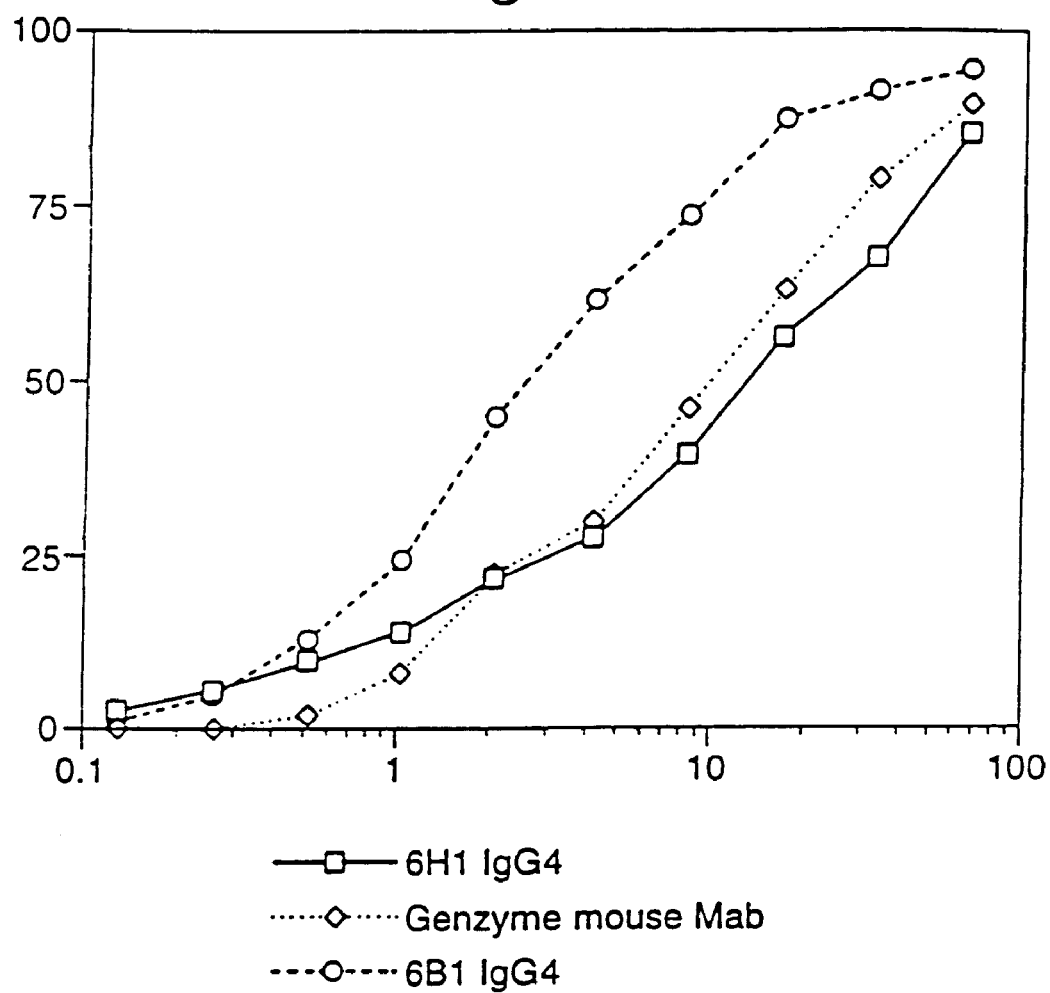
FIG. 16 shows % neutralisation of TGF-β2 anti-proliferative effect on TF1 cells by whole antibodies, 6H1 IgG4, 6B1 IgG4 and the mouse monoclonal from Genzyme, at various concentrations (nM IgG).
Figure 17:
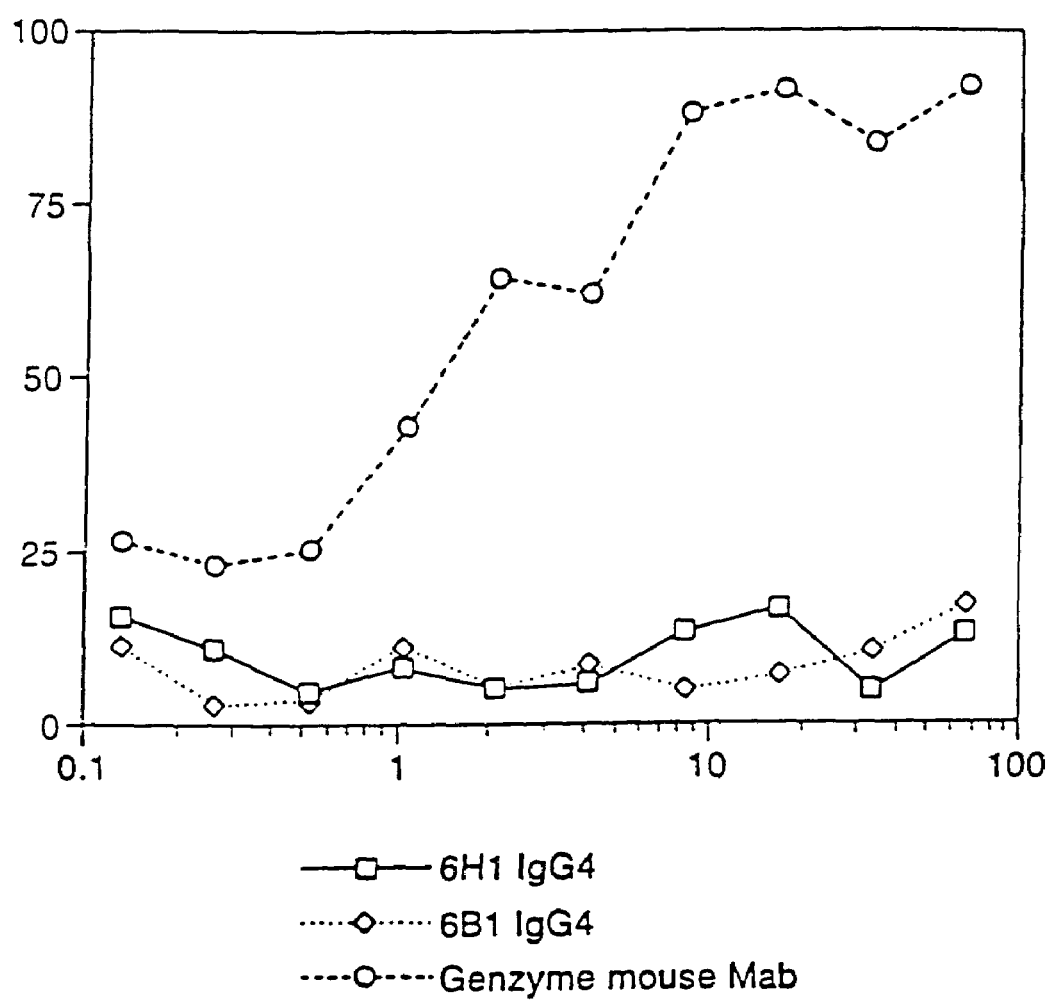
FIG. 17 shows % neutralisation of TGF-β1 anti-proliferative effect on TF1 cells by whole antibodies, 6H1 IgG4, 6B1 IgG4 and the mouse monoclonal from Genzyme, at various concentrations (nM IgG).
Figure 18:
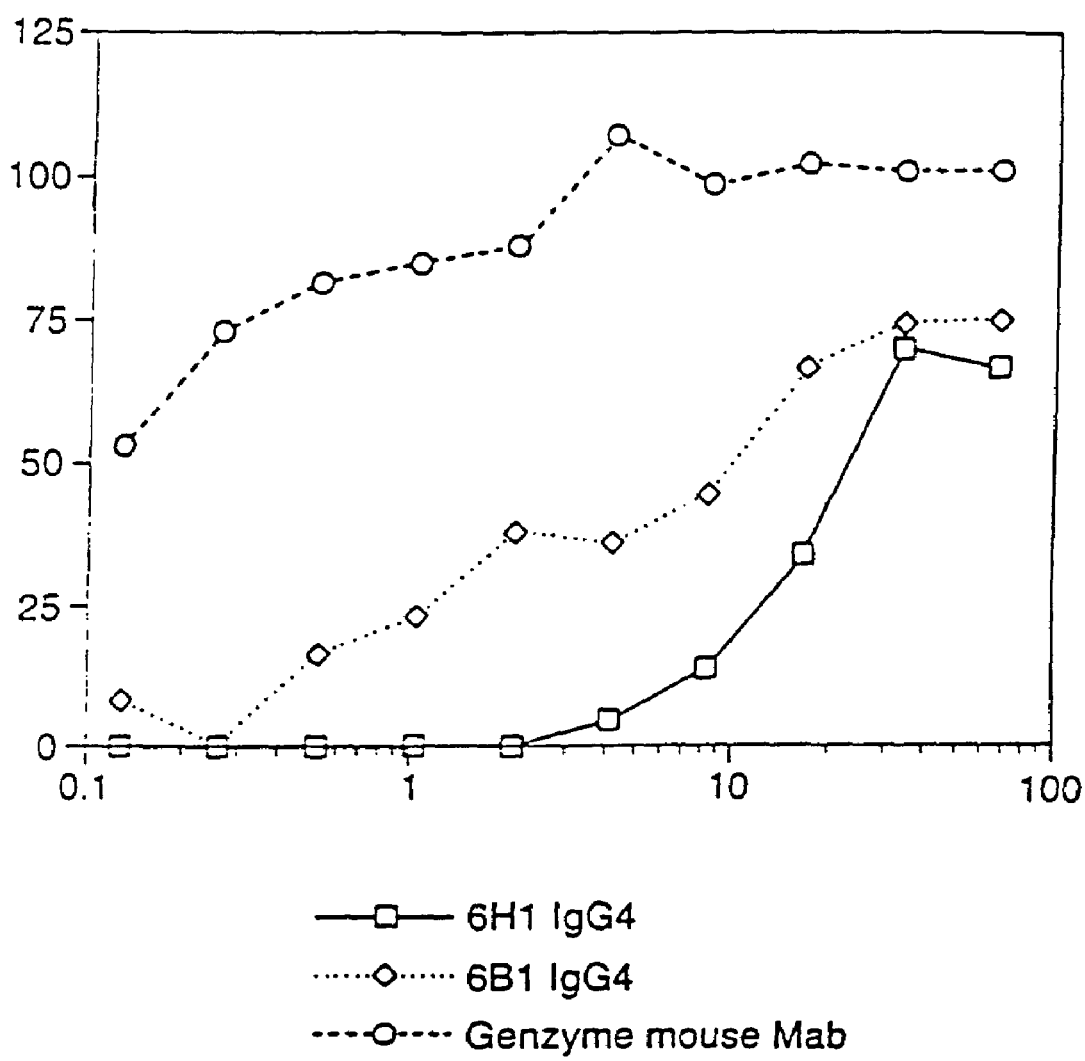
FIG. 18 shows % neutralisation of TGF-β3 anti-proliferative effect on TF1 cells by whole antibodies, 6H1 IgG4, 6B1 IgG4 and the mouse monoclonal from Genzyme, at various concentrations (nM IgG).

As shown in FIG. 16, 6B1 IgG4 strongly neutralises TGFβ2 with an $IC_{50}$ of approximately 2 nM (Table 6). This compares to 10 nM for the mouse monoclonal from Genzyme and 12 nM for 6H1 IgG4. Neither 6B1 IgG4 nor 6H1 IgG4 significantly neutralise TGFβ1 (FIG. 17). However, there is significant neutralisation of TGFβ3 by both 6B1 ($IC_{50}$ ca. 11 nM) and 6H1 IgG4 ca. 20 nM; FIG. 18). This is considerably less than the neutralisation potency of the Genzyme monoclonal ($IC_{50}$ ca. 0.1 nM).

Both 6B1 IgG4 and 6H1 IgG4 are stronger neutralisers of TGFβ2 activity than of TGFgβ3 activity. The neutralisation of TGFβ3 activity is greater than would be predicted from the relative binding of these two isoforms by the antibodies (example 2) and the relative binding in a radioreceptor assay (example 8).

EXAMPLE 8

Inhibition by Antibodies Directed Against TGFβ2 of Binding of Other TGFβ Isoforms to Receptors Measured in a Radioreceptor Assay The ability of 6B1 IgG4 to inhibit binding of TGFβ isoforms to receptors was measured in a radioreceptor assay as described in example 4.

6B1 IgG4 inhibited binding of $^{125}$I-TGFβ2 with an $IC_{50}$ of 0.05 nM. There was no significant inhibition of binding of $^{125}$I-TGFβ1 whereas for $^{125}$I-TGFβ3 6B1 IgG4 inhibited binding with an $IC_{50}$ of approximately 4 nM (Table 6). This indicates the potency of 6B1 IgG4 in this assay and its selectivity for the neutralisation of TGFβ2 activity. Cross-reactivity with TGFβ3 in this assay is less than 2%.

Thus 6B1 IgG4 preferentially inhibits the binding of TGFβ2 to its receptors compared with binding of TGFβ3.

EXAMPLE 9

Assessment of TGFβ1 Antibodies for Therapeutic Use

The antibodies isolated in Example 1 were assessed for potential therapeutic value by in vitro measurements of the ability to inhibit TGFβ1 binding to its receptors and in vitro binding properties.

In Example 4 (Table 5) CS32 showed the strongest inhibition of the antibodies tested of the binding of $^{125}$I-TGFβ1 to receptors on A549 cells. A further comparison was performed between CS32 and further antibodies (CS35, CS37 and CS38) that were isolated as described in the experiment in Example 1, section 5c.

This showed that CS37 appeared to be the most potent of these antibodies in this assay with an $IC_{50}$ of approximately 8 nM, compared with 40 nM for CS32. The IC50 value for CS32 is higher than in the previous assay (Table 5) because the nature of the assay means that the absolute $IC_{50}$ value can vary with assay conditions.

The antibodies 1A-E5 and 1AH-6 (Example 1, section 1f) and antibodies derived from them were much less potent than antibodies derived from 1B2 in neutralising TGFβ activity in this radioreceptor assay.

Thus CS37 was the most potent antibody candidate as assessed by inhibition of binding of $^{125}$I-TGFβ1 to its receptor.

Assessment of Binding to TGFβ3 by Anti-TGFβ1 Antibodies

The antibodies 14A1 and 10A6 (Example 1, section 2(a)(iii)) were shown to preferentially bind TGFβ1 over TGFβ2 and TGFβ3 using the same specificity ELISA as was described in Example 1, section 1 (d)(iii), except that microtitre plates were coated with 50 μl of either 0.2 μg/ml TGFβ1; 0.2 μg/ml TGFβ2; 0.2 μg/ml TGFβ3; 10 μg/ml bovine serum albumin (BSA) or PBS (the uncoated well). The clones were shown to be specific for TGFβ1 since the signal generated in the TGFβ1 coated well was at least five fold greater than the signal on TGFβ2 and TGFβ3.

Antibodies derived from the same 1B2 lineage as these antibodies, such as 27C1/10A6 IgG4 (which contains the same VL as 10A6 and the 27C1 VH was prepared by mutagenesis of CDR3 residues) should have the same cross-reactivity against TGFβ3.

EXAMPLE 10

Construction of a High Expressing Cell Line for 6B1 IgG4 Using the Glutamine Synthase Selection System and Assessment in a Neutralisation Assay Construction of p6H1 VH Gamma4

Figure 20:
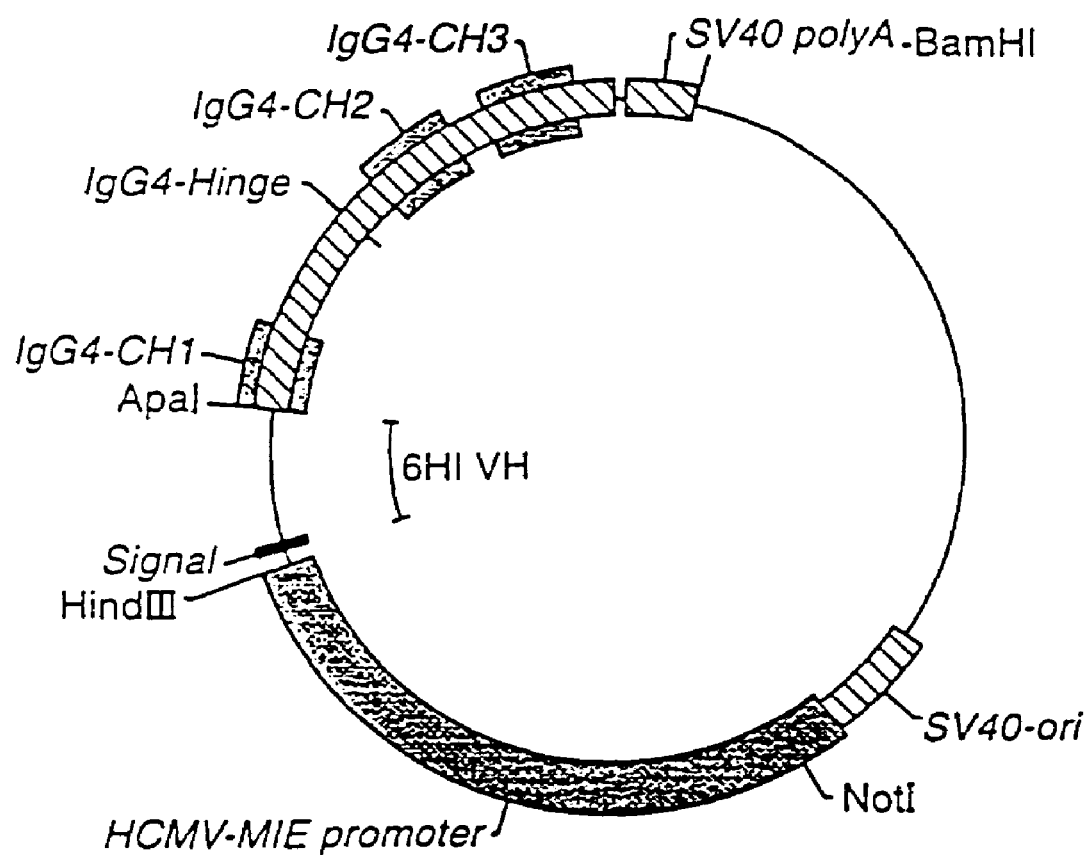
FIG. 20 shows the vector p6H1 VH-gamma4 (7263 bp). The gene encoding 6H1 VH is inserted as a HindIII-ApaI restriction fragment.

6B1 VH was amplified from 6H1 pG4D100 (Example 2) by PCR using oligonucleotides P16 and P17. This DNA was joined by PCR with a 158 bp DNA fragment from M13VHPCR1 (R. Orlandi et al Proc. Natl. Acad. Sci. USA 86 3833-3837, 1989) containing a signal sequence, splice sites and an intron, using oligonucleotides P10 and P17. The PCR product was cut with HindIII ad ApaI and cloned into HindIII-ApaI cut pGamma4 (Lonza Biologics plc). A plasmid with the correct insertion was identified and designated p6H1 VH gamma4 (see FIG. 20). The VH gene and flanking regions were sequenced at this stage.

Construction of 6B1ΔBam pLN10

The VL gene of 6B1 was amplified from the clone of 6B1 scFv in pCANTAB6 (Example 1) and subcloned into pUC119. The VL gene was then mutated by in vitro mutagenesis to remove an internal BamHI site, modifying the DNA sequence but not the protein sequence. In vitro mutagenesis was performed using the oligonucleotide LamDeltaBamHI (SEQ ID NO: 96) (Table 1) using a kit from Amersham International plc. The mutated VL gene was amplified using the primers Vλ3backEuApa (SEQ ID NO:95) and HuJλ2-3ForEuBam (SEQ ID NO:91) and subcloned as an ApaLI-BamHI fragment into the vector, vlcassetteCAT1. The VL gene was then cloned as a HindIII-BamHI fragment into the vector pLN10 (FIG. 8) to generate the vector 6B1ΔBam pLN10.

Construction of p6B1Δ

Figure 21:
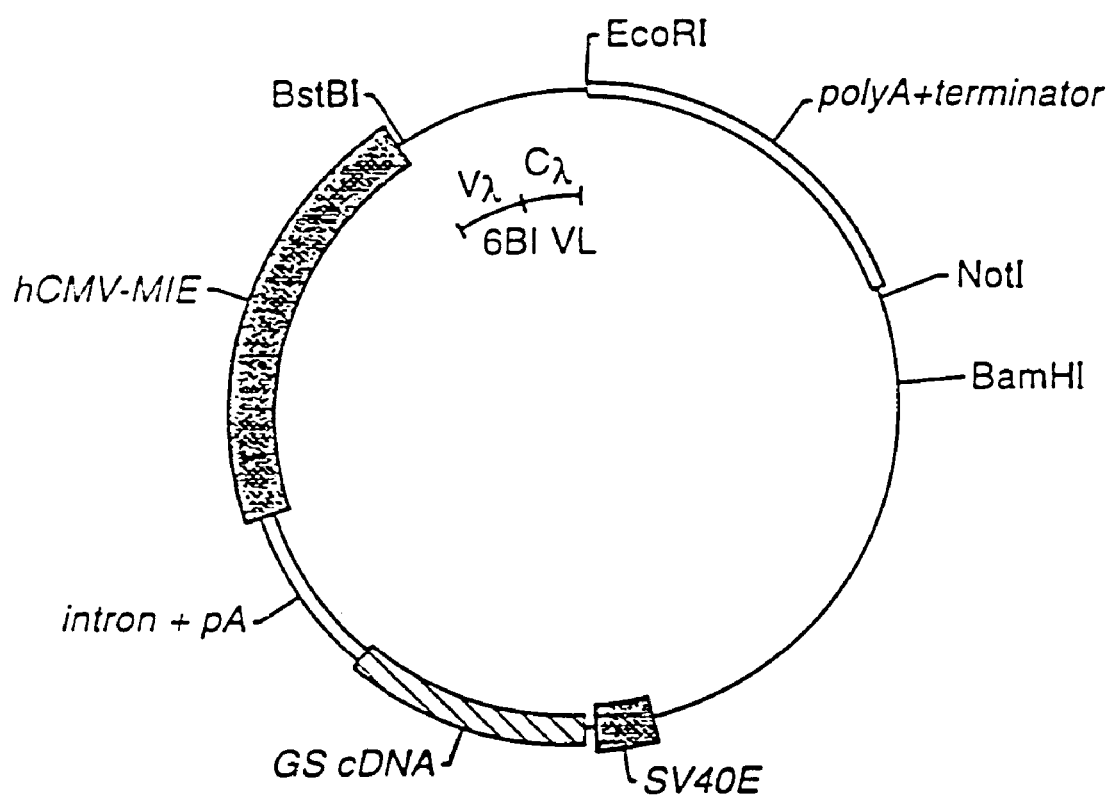
FIG. 21 shows the vector p6B1 lambda (10151 bp). The gene encoding 6B1 VL is inserted as an EcoRI-BstBI restriction fragment.

The 6B1 Vλ gene was amplified by PCR from p6B1ΔBampLN10 using oligonucleotides P22 (SEQ ID NO: 101) and P26 (SEQ ID NO: 103). The Cλ gene was amplified by PCR from pLN10-10A6 (Example 2) using oligonucleotides P25 (SEQ ID NO: 102) and P19 (SEQ ID NO: 100). The 2 DNAs were joined by overlapping PCR using the oligonucleotides P22 (SEQ ID NO: 101) and P19 (SEQ ID NO: 100) and the product cut with BstBI and EcoRI and cloned into BstBI-EcoRI cut pMR15.1 (Lonza Biologics plc). A plasmid with the correct insertion was identified and designated p6B1λ (FIG. 21).

Figure 22:
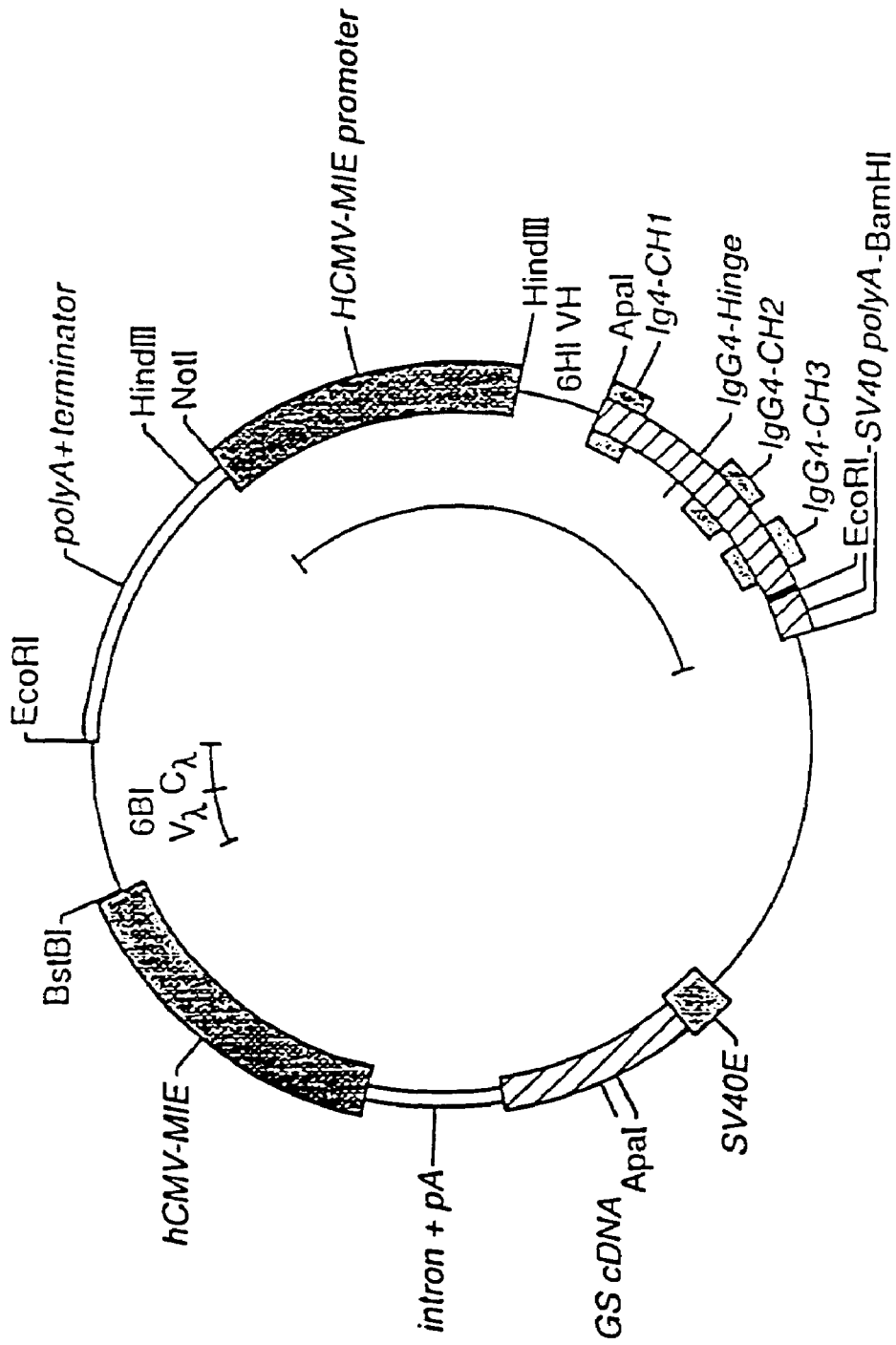
FIG. 22 shows the vector p6B1 gamma4gs (14176 bp). The genes encoding the heavy and light chains of 6BI IgG4 are combined in a single vector.

Construction of Final Expression Vector p6B1gamma4gs p6H1 VHgamma4 and p6B1λ were digested with BamHI and NotI, fragments were purified and ligated together. A plasmid of the desired configuration was identified from transformants and designated p6B1gamma4gs (FIG. 22).

Transfection of NS0 with p6B1 gamma4gs

Stable transfectants secreting 6B1 IgG4 were selected by introducing into NS0 myeloma cells p6B1 which includes the glutamine synthetase (gs) gene which allows growth in glutamine-free (G-) medium (C. R. Bebbington et al Bio/Technology 10 169-175, 1992). 40 μg p6B1 gamma4gs were linearised by digestion with PvuI. The DNA was electroporated into $1.5 \times 10^7$ NS0 cells. Cells were then added to G+DMEM/10% FCS and 50 μl aliquots distributed into 6×96-well plates and allowed to recover for 24 h. The medium was then made selective by the addition of 150 μl G-DMEM/10% FCS. Three weeks later $gs^+$ transfectants were screened by ELISA for the ability to secrete human IgG4λ antibody. The highest producers were expanded and further analysed. From this analysis 5D8 was selected as the candidate production cell line. 5D8 was cloned once by limiting dilution to give the cell line 5D8-2A6.

Assessment of 6B1 IgG4 Derived from Cell Line 5D8-2A6 in the TF1 Neutralisation Assay 6B1 IgG4 was purified from the GS/NS0 cell line 5D8-2A6 grown in serum-free medium as described in Example 2. The 6B1 IgG4 antibody was assayed in the TF1 neutralisation assay as described in Example 3. An $IC_{50}$ value of 1.8 nM was obtained in this assay. Subsequent assays of preparations of 6B1 IgG4 derived from the 5D8-2A6 cell line have indicated values of $IC_{50}$ in the range of 0.65 to 2 nM. These are comparable to the values obtained for 6B1 IgG4 produced from CHO cells (Example 2) and compare favourably with that obtained for 6H1 IgG4 derived from a CHO cell line ($IC_{50}$ of 15 nM). The values obtained for the $IC_{50}$ for 6B1 IgG4 and 6H1 IgG4 in this example are more reliable than those obtained in Example 3 and are shown in Table 4, because of improvements in the assay and in the expression and purification of the antibodies. The $IC_{50}$ value may however be expected to vary with the precise conditions of the assay.

Thus the 6B1 IgG4 provides potent neutralisation of TGFβ2 and is suitable for use as a therapeutic.

EXAMPLE 11

Determination of the Epitope on TGFβ2 for the Antibody 6B1 using a Peptide Phage Display Library The antibody 6B1 was further characterised by epitope mapping. This was done by using a peptide phage display library to select peptide sequences that bind specifically to 6B1. These peptide sequences were then compared to the amino acid sequence of TGFβ2. Correlation between peptide sequences that bind to 6B1 and matching parts of the TGFβ2 amino acid sequence indicate an epitope of TGFβ2 to which 6B1 binds. An "epitope" is that part of the surface of an antigen to which a specific antibody binds.

In this example, the peptide library used was constructed as described by Fisch et al (I. Fisch et al (1996) Proc. Natl. Acad. Sci USA 93 7761-7766) to give a phage display library of $1 \times 10^{13}$ independent clones. Phage displaying peptides that bind to the antibody 6B1 were selected from this library by panning. This was performed as described in Example 1.

Purified 6B1 IgG4 antibody at 10 μg/ml in 4 ml of PBS was coated onto a plastic tube (Nunc; maxisorp) by incubating overnight at 4° C. After washing and blocking with MPBS (see Example 1) an aliquot of the peptide library containing $5 \times 10^{13}$ phage in 4 ml 3% MPBS was added to the tube and incubated at room temperature for 1.5 hours. The tube was washed 10 times with PBST(0.1%), then 10 times with PBS. Bound phage particles were eluted from the tube by adding 4 ml of 100 mM triethylamine and incubating the tube stationary for 10 minutes at room temperature. The eluted phage were then added to a tube containing 2 ml 1M-Tris.HCl (pH7.4) and 10 ml 2YT broth. The phage were then added to 20 ml of logarithmically growing E. coli TG1 cells and grown for 1 hour shaking at 100 rpm at 37° C. The infected cells were then plated on 2YT agar medium with 15 µg/ml tetracycline in 243 mm×243 mm dishes (Nunc). Plates were incubated at 30° C. for 18 hours. Colonies were scraped off the plates into 10 ml 2TY broth containing 15% (v/v) glycerol for storage at −70° C.

250 µl of cells from the first round of selection was used to inoculate 500 ml 2YT broth (containing 15 µg/ml tetracycline) in a 2 liter conical flask and grown overnight, at 30° C. with shaking at 280 rpm. A 2 ml aliquot of this culture was then taken and centrifuged to remove all cells. 1 ml of this phage supernatant was the used for a second round of selection as described above. The pattern of phage growth and panning was repeated over a third and a fourth round of selection.

Individual colonies from the fourth round of selection were used to inoculate 100 µl 2YT broth (containing 15 µg/ml tetracycline) into individual wells of 96 well tissue culture plates and grown overnight with gentle shaking at 100 rpm at 30° C. Glycerol was added to a final concentration of 15% (v/v) and these master plates were stored frozen at −70° C.

These clones were screened for clones that bound specifically to the antibody 6B1 in ELISA. Cells from the master plates were used to inoculate 96 well tissue culture plates containing 100 µl 2YT broth (containing 15 µg/ml tetracycline) per well and grown overnight with gentle shaking at 100 rpm at 30° C. The plates were then centrifuged at 2000 rpm. The 100 µl phage supernatants from each well were recovered and each was mixed with 100 µl of 4% skimmed milk powder in 2×PBS. 100 µl of each of these was then assayed by phage ELISA. Purified 6B1 IgG4 antibody at 10 µg/ml in PBS was coated onto flexible microtitre plates by incubating overnight at 4° C. Control plates coated with an irrelevant IgG4 antibody at 10 µg/ml were also prepared. The ELISAs were performed as described in Example 1, and visualised with the chromagenic substrate pNPP (Sigma).

Approximately 20% of all the clones analysed bound to the 6B1 coated plate. None of the clones analysed bound to ELISA plates coated with the irrelevant antibody. Binding therefore appeared to be specific for the binding site of the antibody 6B1.

Clones which bound 6B1 were analysed by DNA sequencing as described by Fisch et al. A total of 31 different clones were sequenced. These were analysed for possible matches with the sequence of TGFβ2 using Mac vector software of these clones, 12 showed poor matching with the sequence of TGFβ2 and 10 had no similarity at all. However, there were 4 different clones (some of which had been selected more than once) which showed a reasonable match to a region of the TGFβ2 sequence between amino acid positions 56 to 69. Table 8 shows the amino acid sequence of the exon of each of these clones that appears to be responsible for binding to 6B1 (SEQ ID NOS: 104 to 108).

None of these clones exactly match the sequence of TGFβ2 nor is there a single clear consensus sequence between the peptide clones. Nevertheless, careful examination of the sequences reveals a match with residues 60 to 64 of TGFβ2 (SEQ ID NO: 1) (Table 8). Lining up four clones with L at position 64 reveals 2 clones with R at position 60, 1 clone with V at position 61, 2 with L at position 62 and 3 with S at position 63. This provides the sequence RVLSL corresponding to residues 60 to 64 (SEQ ID NO: 1) which form part of the alpha helix which forms the heel region of TGFβ2. An antibody recognising this structure would not be expected to make contact with every amino acid residue in the helix and so a peptide mimicking this sequence could have considerable sequence variation at positions that correspond to parts of the helix that do not make contact. The alpha helix recognised is believed to form part of the receptor binding region of TGFβ2 (D. L. Griffith et al. (1996) Proc. Natl. Acad. Sci. US0A 93 878-883).

EXAMPLE 12

Determination by Immunohistochemistry of Binding of 6B1 IgG4 to TGFβ2 in Mammalian Tissue and Absence of Cross Reactivity To detect TGFβ2 in formalin-fixed tissue sections that express the cytokine, the tissue section is generally treated with a protease, pronase E. This digestion step unmasks the antigen, possibly activating latent TGFβ2 to give active TGFβ2. 6B1 IgG4 detects only the active form of TGFβ2 (Example 6).

Using 6B1 IgG4 and immunohistochemical methods the distribution of TGFβ2 was determined in formalin fixed-paraffin wax embedded rat normal rat kidney, and experimentally lesioned rat brain tissue, following pronase E digestion.

The reactivity of 6B1 IgG4 in frozen cryostat sections of acetone post-fixed normal human tissue was also ascertained to determine whether there was any binding to other antigens in these tissues.

Method

Rat Tissue

Paraffin embedded rat tissues were de-waxed and rehydrated through an alcohol series. The sections were then treated with 0.1% pronase E for exactly 8 min and then washed in water. TGFβ2 was detected in the sections using 6B1 IgG4 at 500 ng/ml following the protocol provided with a Vectastain ABC (avidin-biotin-complex) kit from Vector Laboratories. On kidney sections, bound antibody was located with alkaline phosphatase and peroxidase was used on rat brain tissues.

Human Tissue

The following human tissue samples were used: Adrenal, Aorta, Blood, Large intestine, Small intestine, Cerebrum, Kidney, Lymph Node, Liver, Lung, Spleen, Pancreas, Skeletal muscle, Cardiac Muscle, Thyroid, Nerve, Skin, Eye.

Cryostat sections and smears were fixed for 15 minutes in acetone before application of 6B1 IgG4 antibody labelled with FITC using Sigma Immunoprobe kit. The labelled antibody was incubated for 18 hr at 4° C., then detected using an indirect alkaline phosphatase method (detection with anti-FITC antibody followed with anti-species enzyme conjugated antibody). In instances where endogenous alkaline phosphatase activity could not be suppressed a peroxidase detection method was used. No pronase digestion was used in this case, therefore this procedure would detect only antigens with which the antibody cross-reacts.

Results

Rat Tissue

Rat kidneys displayed positive staining in tubules present on both the apical and the basolateral side, demonstrating the presence of TGFβ2 in the tissues.

Injured rat brain at 5 days post injury showed positive staining of neurones, astrocytes and macrophages which was absent in normal brain. This indicates that the TGFβ2 is expressed in rat brain following injury.

Human Tissue

No specific staining of any tissue was observed using fixed cryostat sections of the tissues listed above. Therefore 6B1 IgG4 does not cross-react with antigens in these tissues and when used therapeutically will bind only active TGFβ2 in tissue sections detected by immunohistochemical methods.

EXAMPLE 13

Kinetic Analysis of the Binding of 6B1 Single Chain Fv and 6B1 IgG4 to TGFβ Isoforms Surface plasmon resonance (SPR) can be used to examine real-time interactions between an immobilised ligand and an analyte, and derive kinetic constants from this data. This was performed using the BIAcore 2000 system (Pharmacia Biosensor) with the antigen immobilised on a surface, and the antibody as analyte.

The system utilises the optical properties of surface plasmon resonance to detect alterations in protein concentration within a dextran matrix. Antigen is covalently bound to the dextran matrix at a set amount, and as solution containing antibody passes over the surface to which this is attached, antibody binds to the antigen, and there is a detectable change in the local protein concentration, and therefore an increase in the SPR signal. When the surface is washed with buffer, antibody dissociates from the antigen and there is then a reduction in the SPR signal, so the rate of association, and dissociation, and the amount of antibody bound to the antigen at a given time can all be measured. The changes in SPR signal are recorded as resonance units (RU), and are displayed with respect to time along the y-axis of a sensorgram.

The density of immobilised ligand on the surface of a BIACore chip is important when deriving kinetic data from the sensorgrams generated. It needs to be quite low, so that only a small amount of analyte antibody is needed for saturation of the chip surface.

For simplicity, the density of a chip surface is quoted in RU's, and an ideal amount for a ligand such as TGFβ2 or TGFβ3 (25 kDa) is 400-600 RU's relative to the baseline set during the immobilisation of the ligand to the surface. The actual amount of TGFβ that has to be added to get the correct density has to be determined by investigation, but is reproducible once the correct concentration has been found.

Immobilisation of the ligand to the dextran matrix of the chip surface is facilitated via amine groups, on lysine side chains in the protein, and carbosxyl groups in the dextran matrix. The carboxyl groups in the dextran are activated with N-hydroxysuccinimide (NHS) and N-ethyl-N'-(3-diethylaminopropyl)carbodiimide (EDC) the antigen in acidic solution is then bound to the surface, and finally any unreacted carboxyl groups are blocked with ethanolamine.

The immobilisation of ligand is automated by the BIA-Core 2000 machine, and all steps are carried out in the autosampler or in the flowcell, on the dextran surface of the chip. The buffer used throughout the immobilisation procedure, and the analysis of samples is Hepes-buffered saline (HBS) with a surfactant (Pharmacia Biosensor). The chips (Pharmacia, CM5), have dextran coating on a thin layer of gold. NHS at 100 mM and EDC at 400 mM are mixed by the autosampler, and then a fixed volume is injected over the flowcell surface. This is followed by an injection of antigen in a suitable buffer. In the case of TGFβ, a surface of the correct density was given by using 25-30 μg/ml solution of TGFβ2 (AMS) OR TGFβ3 (R & D systems) in 10 mM acetate. After injection of the ligand, the chip is blocked using 1M ethanolamine. The total amount of TGFβ bound was assessed from the total increase in resonance units over this period.

To determine the kinetic parameters, a series of dilutions of the antibody samples was made in HBS from about 500 μg/ml down to less than 1 μg/ml, usually through doubling dilutions. After the antibody has been injected over the antigen surface, the surface is washed with HBS, then regenerated by stripping off the bound antibody with a pulse of 100 mM HCl. At the higher concentrations of antibody the antigen on the chip surface is saturated, and the off rate is determined on washing with buffer in the dissociation phase. For determination of the on-rate, lower concentrations of antibody are used, giving a linear binding phase in the sensorgram, allowing $k_{on}$ determination.

The set of dilutions were repeated on a separate preparation of the same antibody.

To manipulate the sensorgrams to obtain kinetic constants $k_{on}$ and $k_{off}$ the BIAevaluation software package is used. For each binding curve used in the calculations, care was taken that the conditions were appropriate for the determination of kinetic constants.

6B1 IgG4 was purified from the GS/NS0 cell line of Example 10 as in Example 2. 6B1 single chain Fv was expressed intracellularly in *E. coli*, refolded in vitro (using the methodology of WO94/18227), and purified to give a homogeneous product. The values of $k_{on}$ and $k_{off}$ were determined for 6B1 IgG4 for binding to both TGFβ2 and TGFβ3, and for the single-chain Fv 6B1 for binding to TGFβ2. The dissociation constant was calculated by dividing $k_{off}$ by $k_{on}$. The values for these kinetic parameters are shown in Table 7.

Thus, 6B1 scFv and 6B1 IgG4 show very low dissociation constants of 2.3 nM and 0.89 nM respectively for TGFβ2, and there is 9% cross-reactivity with TGFβ3 (as judged by the ratio of dissociation constants of 6B1 IgG4 for TGFβ3 and TGFβ2). For comparison, in earlier studies, where the standard errors were greater and the values less precise, the Kd values for TGFβ2 were determined to be 0.7 nM for 6A5 scFv (Table 2) and 2 nM for 6H1 IgG4 (Example 2). The Kd values for all the antibodies directed against TGFβ2 which share the same 6H1 VH domain are low and below 10 nM.

EXAMPLE 14

Binding of a Peptide Corresponding to Residues 56 to 69 of TGFβ2 to 6B1 IgG4

A peptide was synthesised corresponding to the amino acids of TGFβ2 surrounding the residues RVLSL, the epitope identified from the selection of phage from the peptide display library (Example 11).

The 17-mer peptide CGGTQHSRVLSLYNTIN (SEQ ID NO: 109) (TGFβ2$_{56-69}$; synthesised by Cambridge Research Biochemicals) contains residues 56 to 69 of TGFβ2 with RVLSL (residues 60 to 64) (SEQ ID NO: 1) at its centre.

The CGG N-terminal extension is a spacer with a cysteine residue to facilitate coupling of the peptide to carrier proteins. The peptide corresponding to residues 56 to 69 from TGFβ1 (TGFβ1$_{56-69}$; CGGTQYSKVLSLYNQHN) (SEQ ID NO: 3) was also synthesised. As a control, irrelevant peptide GPEASRPPKLHPG (SEQ ID NO: 110) was used.

Two approaches were used to confirm that the epitope on TGFβ2 for 6B1 IgG4 comprised the amino acids RVLSL (SEQ ID NO: 1).

(i) Assessment of the ability of 6B1 IgG4 to bind to TGFβ2$_{56-69}$ and TGFβ1$_{56-69}$ coupled to BSA by ELISA (ii) Assessment of the ability of peptides to bind to 6B1 IgG4 coated onto a BIACore sensor chip.

(i) Assessment of Ability of 6B1 IgG4 to Bind to TGFβ2$_{56-69}$ and TGFβ1$_{56-69}$ Coupled to BSA by ELISA The binding of 6B1 IgG4 to synthetic peptides TGFβ1$_{56-69}$ (SEQ ID NO: 3) and TGFβ2$_{56-69}$ (SEQ ID NO: 109) conjugated to BSA was assessed in an ELISA assay. This was compared with the binding of a control antibody 2G6 IgG4 which is an engineered antibody with a heavy chain containing a VH from an antibody directed against the hapten NIP combined with a light chain containing a VL from an antibody directed against lysozyme.

Method

Two mg of each of the peptides TGFβ1$_{56-69}$ (SEQ ID NO: 3) and TGFβ2$_{56-69}$ (SEQ ID NO: 109) were conjugated to BSA using an Imject Activated Immunogen Conjugation kit (Pierce).

An immunosorp microtitre plate (Nunc) was coated overnight with 10 ug/ml of the conjugated peptides in PBS (rows A-D TGFβ1$_{56-69}$, rows E-F TGFβ2$_{56-69}$) at 100 µl/well. The wells were washed 3× with PBS-tween and the following additions made: Column 1 –100 µl PBS in each well as reagent control; Column 2, rows A, B, E and F 200 µl of 6B1 IgG4 10 µg/ml; Column 2, rows C, D, G and H 200 µl of 2G6 IgG4 10 µg/ml.

100 µl of PBS was put into all the remaining wells. To produce doubling dilutions of the antibodies, 100 µl was removed from each well in column 2 and placed into the next well in column 3. The sample was mixed and 100 µl removed and added to the next well in column 4. This procedure was repeated along the plate with the last 100 µl being discarded. The plate was then incubated at 4° C. for 18 hr.

After 3× washes with PBS-tween the wells were refilled with 100 µl of an alkaline phosphatase conjugate of goat F(ab')$_2$ fragment specific for the human IgG gamma chain diluted 1:1000 in PBS and incubated for a further 1 hr. After 3× further washes with PBS-tween bound antibody was revealed with p-NPP substrate for 20 min.

Results

Figure 15:
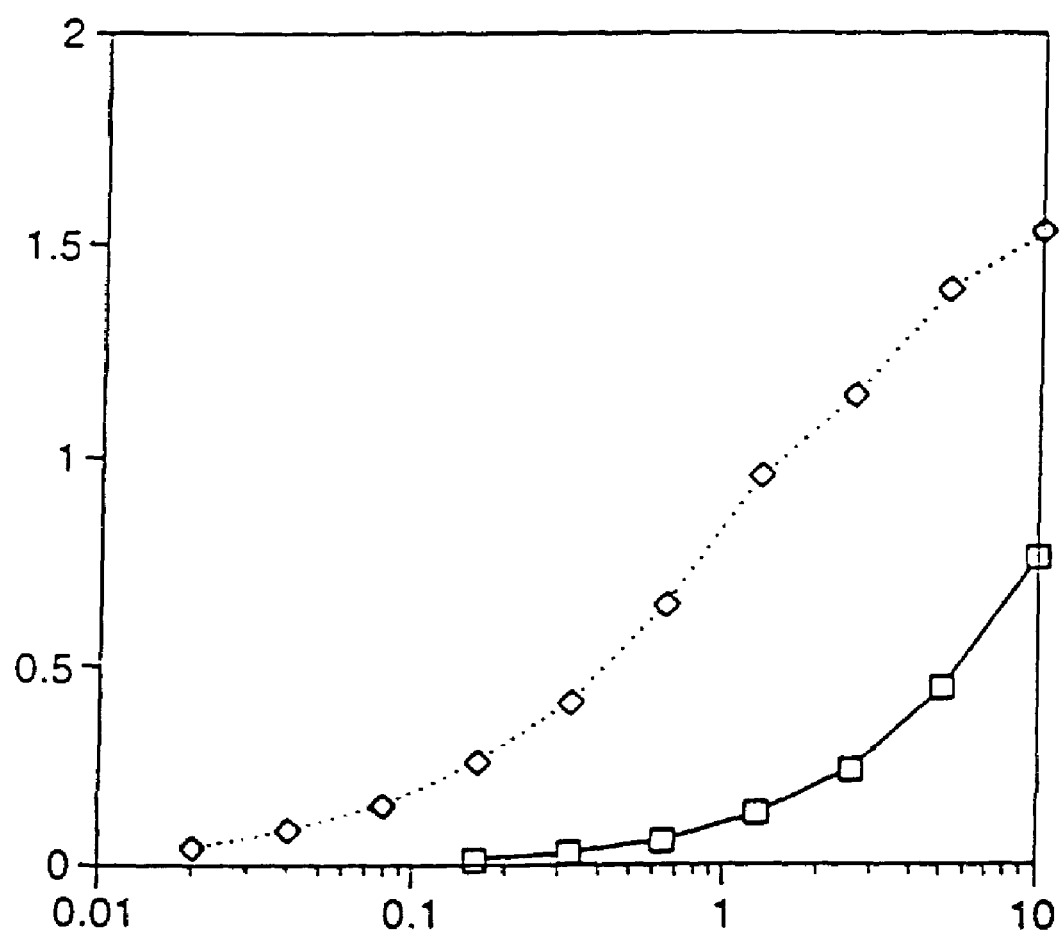
FIG. 15 shows data from an ELISA detecting binding of 6B1 IgG4 to BSA conjugated with either peptide TGFβ2$_{56-69}$ or peptide TGFβ1$_{56-69}$ coated on to an ELISA plate. 6B1 IgG4 was incubated at various concentrations in µg/ml and the absorbance at 405 nm measured after addition of the detection agents. OD405 nm results are plotted at the various concentrations for BSA-TGFβ2$_{56-69}$ ("Beta2 peptide"—diamonds) and BSA-TGFβ1$_{56-69}$ ("Beta1 peptide"—squares).

6B1 IgG4 was shown to bind to both conjugated peptides (FIG. 15) but the ELISA signal obtained with TGFβ1$_{56-69}$ (SEQ ID NO: 3) was much lower than that obtained with TGFβ2$_{56-69}$ (SEQ ID NO: 109) at an equivalent concentration of 6B1 IgG4. An approximately 8 to 10 times higher concentration of 6B1 IgG4 was required to obtain an equivalent signal with TGFβ1$_{56-69}$ (SEQ ID NO: 3) compared with TGFβ2$_{56-69}$ (SEQ ID NO: 109). No signal was obtained with the control 2G6 IgG4 antibody with either peptide-BSA conjugate. 6B1 IgG4 therefore strongly binds TGFb256-69 (SEQ ID NO: 109) and more weakly binds TGFβ1$_{56-69}$ (SEQ ID NO: 3) coupled to BSA.

(ii) Assessment of the Ability of Peptides to Bind to 6B1 IgG4 Coated onto a BIACore Sensor Chip.

The binding of 6B1 IgG4 to TGFβ2$_{56-69}$ (SEQ ID NO: 109) was confirmed by binding the peptide to 6B1 IgG4 coated on to a BIACore sensor chip. The determination of binding properties by surface plasmon resonance using the Pharmacia BIACore 2000 was described in Example 13. The method of creating a BIACore sensor chip coated with 6B1 IgG4 was as for the method for coupling with TGFβ, described in Example 13, except that 6B1 IgG4 was coupled at 5 µg/ml in 10 mM acetate buffer, pH3.5. A surface of 5000RU was generated using 25 µl of 6B1 IgG4.

Twenty µl of the peptides were applied to the 6B1 surface at 1 mg/ml with regeneration of the surface using an acid pulse to remove bound peptide between samples. The amount of binding was assessed by setting a baseline response of absolute RU prior to injection, and then subtracting this from the value at 20 seconds after the injection was complete to give a relative response in RU. This is taken to be the amount of binding to the 6B1 surface. The binding obtained is shown in Table 9. There was a very low level of binding of the irrelevant peptide. TGFβ1$_{56-69}$ appeared to bind specifically at a low level to 6B1 IgG4. However, the TGFβ2$_{56-69}$ peptide bound to 6B1 IgG4 specifically and very much more strongly.

The low level of binding of 6B1 IgG4 to the TGFβ1 peptide in the ELISA and BIACore assays is not unexpected given that 10 of the 14 TGFβ amino acids are identical with the TGFβ2 peptide. Nevertheless, 6B1 IgG4 binds the TGFβ2$_{56-69}$ peptide very much more strongly than it binds the TGFβ1$_{56-69}$ peptide. The level of discrimination between these TGFβ1 and TGFβ2 peptides is very much lower however than is seen for the radioreceptor (Table 6) and neutralisation assays (Table 6 and FIGS. 16 and 17) with native isoforms.

In these assays, 6B1 IgG4 strongly neutralises TGFβ2 but has little effect on TGFβ1 biological activity. This greater discrimination presumably reflects the context of the residues of the peptides in the native isoforms.

Conclusions

These results support the assignment of the epitope of 6B1 IgG4 on TGFβ2 to the aminoacids in the region of residues 60 to 64. The peptide used in this example, residues 56 to 69, corresponds to the amino acids of alpha helix H3 (M. P. Schlunegger & M. G. Grutter Nature 358 430-434, 1992). TGFβ2 forms a head-to-tail dimer with the alpha helix H3 (also referred to as the heel) of one subunit forming an interface with finger regions (including residues 24 to 37 and residues in the region of amino acids 91 to 95; also referred to as fingers 1 and 2) from the other subunit (S. Daopin et al Proteins: Structure, Function and Genetics 17 176-192, 1993). It has been proposed that the primary structural features which interact with the TGFβ2 receptor consist of amino acids at the C-terminal end of the alpha helix H3 from one chain together with residues of fingers 1 and 2 of the other chain (D. L. Griffith et al Proc. Natl. Acad. Sci. USA 93 878-883, 1996). The identification of an epitope for 6B1 IgG4 within the alpha helix H3 of TGFβ2 is consistent with 6B1 IgG4 preventing receptor binding and neutralising the biological activity of TGFβ2.

If the epitope for 6B1 IgG4 is three dimensional there may be other non-contiguous epitopes to which the antibody may bind. There is earlier evidence that antibodies directed against this region of TGFβ2 may be specific for TGFβ2 and neutralise its activity. Flanders et al (Development 113 183-191 1991) showed that polyclonal antisera could be raised in rabbits against residues 50 to 75 of mature TGFβ2 and that these antibodies recognised TGFβ2 but not TGFβ1 in Western blots. In an earlier paper, K. C. Flanders et al (Biochemistry 27 739-746, 1988) showed that polyclonal antisera raised in rabbits against amino acids 50 to 75 of TGFβ1 could neutralise the biological activity of TGFβ1. The antibody we have isolated and characterised, 6B1 IgG4, is a human antibody directed against amino acids in this region which neutralises the biological activity of human TGFβ2. It is surprising that such a neutralising antibody against TGFβ2 can be isolated in humans (where immunisation with a peptide cannot be used for ethical reasons) directly from a phage display antibody repertoire.

EXAMPLE 15

Suppression of Experimental Glomerulonephritis Using Human Antibodies Against Human TGFβ

The ability of human antibodies against human TGFβ to neutralise TGFβ activity, and thus prove beneficial in the treatment of fibrotic disease, was tested in an animal model of the kidney disease, glomerulonephritis.

Antibodies directed against TGFβ1 have been shown to be effective in the suppression of experimental glomerulonephritis (W. A. Border et al Nature 346 371-374, 1990) and other fibrotic diseases (W. A. Border & N. A. Noble New Engl. J. Med. 331 1286-1292, 1994). In this example, it is shown that antibodies directed against either TGFβ1 or TGFβ2 are effective in the treatment of glomerulonephritis. Induction of glomerulonephritis in rats with a single injection of anti-thymocyte serum was followed by treatment with an injection of either antibody directed against TGFβ1 or of saline.

31G9 and 6A5 scFv (example 1) were expressed using a T7 polymerase controlled vector system (J. H. Christensen et al FEBS Lett. 281 181-184, 1991). Active scFv protein was prepared from inclusion bodies using the methodology described in WO94/18227 (H. C. Thøgersen et al). The scFv preparations were homogeneous as determined by SDS-PAGE and by gel filtration chromatography on Superose 12.

Five groups of rats were used

Group A: Normal controls, no anti-thymocyte serum treatment

Group B: Disease control (saline treatment)

Group C: Treatment daily with 25 µg 31G9 single chain Fv (anti-TGFβ$_1$)

Group D: Treatment daily with 25 µg 6A$^5$ single chain Fv (anti-TGFβ$_2$)

Group E: Treatment daily with 25 µg 31G9 and 8æg 6A5 single chain Fv

Groups B to E each received a dose of 0.25 ml sheep anti-thymocyte serum (ATS; Border et al, 1990 supra). One hour after ATS injection, each group received 200 µl PBS (group B) or the appropriate antibody (200 µl in PBS). On days 1 to 5, these doses were repeated for groups B to E. On day 6, all rats were sacrificed.

Figure 24:
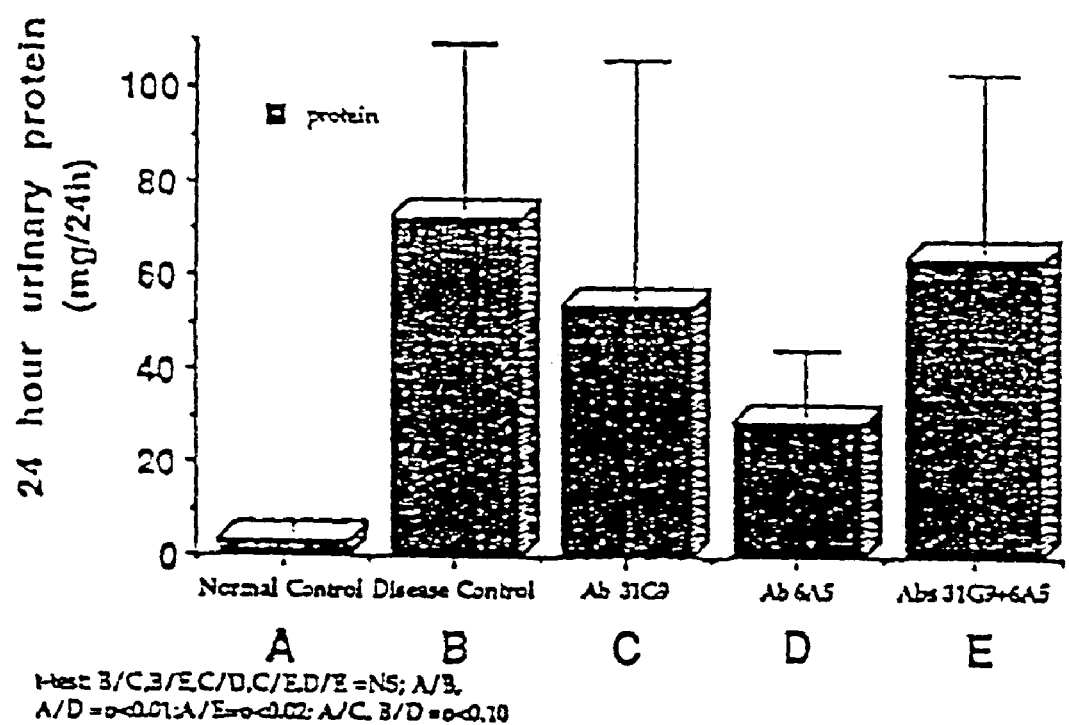
FIG. 24 shows the amount of urinary protein in 24 h measured for rat groups A to E in the experimental glomerulonephritis model.
Figure 25:
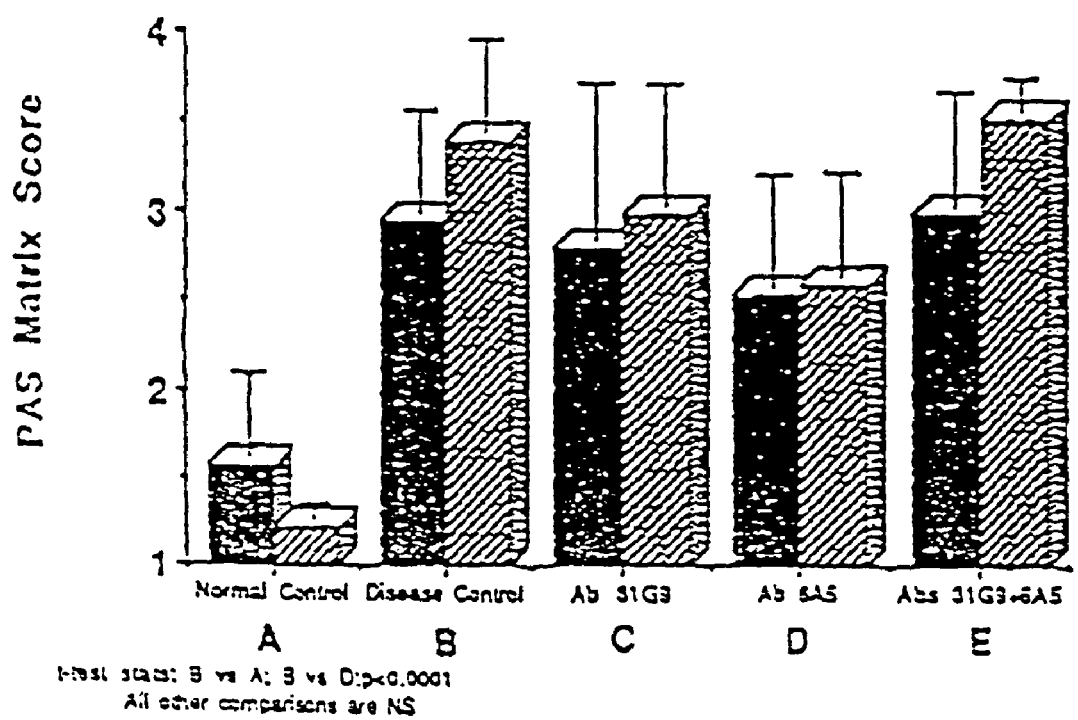
FIG. 25 shows the periodic acid Schiff matrix score (derived by measurement of the amount of staining) rat groups A to E in experimental glomerulonephritis model.

Urinary protein was measured (a measure of glomerular injury: J. M. Ginsberg et al New Engl. J. Med. 309 1543-1550, 1983) for 24 h on days 5 to 6 and was found to be significantly lower for the rats treated with 6A5 scFv than for the disease control (see FIG. 24). The extent of glomerular injury was determined by examination of glomeruli stained with periodic acid-Schiff's base (30 glomeruli for each rat). These glomeruli are scored for the extent of glomerular matrix accumulation (30 glomeruli for each rat) on histological examination of stained sections (Border et al, 1990 supra; W. A. Border et al Nature 360 361-364, 1992). Scoring was performed by two independent scientists for each rat. There was a significantly lower increase in extracellular matrix deposition for the 6A5 scFv treated rat compared to the disease control (FIG. 25). There was also a somewhat lower increase for 31G9 scFv but this difference in deposition was not statistically significant.

Hence the human antibody against human TGFβ2 is effective in suppression of experimental glomerulonephritis.

TABLE 1

Oligonucleotide primers used in the identification and characterisation of TGF-b1 antibodies.

| Primer | Nucleotide sequence 5' to 3' | |
|---|---|---|
| 1B2 mutVHCDR3 | 5' CGT GGT CCC TTT | (SEQ ID NO: 68) |
| | GCC CCA GAC GTC CAC | |
| | ACC ACT AGA ATC GTA | |
| | GCC ACT ATA TTC CCC | |
| | AGT TCG CGC ACA GTA | |
| | ATA CAC AGC CGT | |
| pUC19reverse | 5' AGC GGA TAA CAA | (SEQ ID NO: 69) |
| | TTT CAC ACA GG 3' | |
| fdtet seq | 5' GTC GTC TTT CCA | (SEQ ID NO: 70) |
| | GAC GTT AGT 3' | |
| PCR-H-Link | 5' ACC GCC AGA GCC | (SEQ ID NO: 71) |
| | ACC TCC GCC 3' | |
| PCR-L-Link | 5' GGC GGA GGT GGC | (SEQ ID NO: 72) |
| | TCT GGC GGT 3' | |
| myc seq 10 | 5' CTC TTC TGA GAT | (SEQ ID NO: 73) |
| | GAG TTT TTG 3' | |
| HuJH4-5For | 5' TGA GGA GAC GGT | (SEQ ID NO: 74) |
| | GAC CAG GGT TCC 3' | |
| RL1 | 5' G(C/A)A CCC TGG | (SEQ ID NO: 75) |
| | TCA CCG TCT CCT CA | |
| | GGT GGA GGC GGT TCA | |
| | GGC GGA GGT GGC AGC | |
| | GGC GGT GGC GGA TCG | |
| | 3' | |
| RL2 | 5' GGA CAA TGG TCA | (SEQ ID NO: 76) |
| | CCG TCT CTT CA GGT | |
| | GGA GGC GGT TCA GGC | |
| | GGA GGT GGC AGC GGC | |
| | GGT GGC GGA TCG 3' | |
| RL3 | 5' GGA CCA CGG TCA | (SEQ ID NO: 77) |
| | CCG TCT CCT CA GGT | |
| | GGA GGC GGT TCA GGC | |
| | GGA GGT GGC AGC GGC | |
| | GGT GGC GGA TCG 3' | |

TABLE 1-continued

Oligonucleotide primers used in the identification and characterisation of TGF-b1 antibodies.

| Primer | Nucleotide sequence 5' to 3' |
|---|---|
| VH1b/7a back Sfi | 5'-GTC CTC GCA ACT GCG GCC CAG CCG GCC ATG GCC CAG (AG)TG CAG CTG GTG CA(AG) TCT GG-3' (SEQ ID NO: 78) |
| Vh1c back Sfi | 5'-GTC CTC GCA ACT GCG GCC CAG CCG GCC ATG GCC (GC)AG GTC CAG CTG GT(AG) CAG TCT GG-3' (SEQ ID NO: 79) |
| VH2b back Sfi | 5'-GTC CTC GCA ACT GCG GCC CAG CCG GCC ATG GCC CAG (AG)TC ACC TTG AAG GAG TCT GG-3' (SEQ ID NO: 80) |
| VH 3b back Sfi | 5'-GTC CTC GCA ACT GCG GCC CAG CCG GCC ATG GCC (GC)AG GTG CAG CTG GTG GAG TCT GG-3' (SEQ ID NO: 81) |
| VH3C back Sfi | 5'-GTC CTC GCA ACT GCG GCC CAG CCG GCC ATG GCC GAG GTG CAG CTG GTG GAG (AT)C (TC) GG-3' (SEQ ID NO: 82) |
| VH4b back Sfi | 5'-GTC CTC GCA ACT GCG GCC CAG CCG GCC ATG GCC CAG GTG CAG CTA CAG CAG TGG GG-3' (SEQ ID NO: 83) |
| VH4c back Sfi | 5'-GTC CTC GCA ACT GCG GCC CAG CCG GCC ATG GCC CAG (GC)TG CAG CTG CAG GAG TC (GC) GG-3' (SEQ ID NO: 84) |
| VH5b back Sfi | 5'-GTC CTC GCA ACT GCG GCC CAG CCG GCC ATG GCC GA(AG) GTG CAG CTG GTG CAG TCT GG-3' (SEQ ID NO: 85) |
| VH 6a back Sfi | 5'-GTC CTC GCA ACT GCG GCC CAG CCG GCC ATG GCC CAG GTA CAG CTG CAG CAG TCA GG-3' (SEQ ID NO: 86) |
| VH3BACKSfiEu | 5'-AGC TCG GTC CTC GCA ACT GCG GCC CCT GGG GCC CAC AGC GAG GTG CAG CTG GTG GAG TCT GG-3' (SEQ ID NO: 87) |
| VHJH6FORBam | 5'-CGA GTC ATT CTG CAC TTG GAT CCA CTC ACC TGA GGA GAC GGT GAC CGT GGT CCC-3' (SEQ ID NO: 88) |
| DeltaBamHI | 5'-GA GAA TCG GTC TGG GAT CCT GAG GGC CG G-3' (SEQ ID NO: 89) |
| vλ3/4BackEuApa | 5'-AGC TCG GTC CTC GCA ACT GGT GTG CAC TCC CAC GTT ATA CTG ACT CAG GAC CC -3' (SEQ ID NO: 90) |
| HuJλ2-3ForEuBam | 5'-G GTC CTC GCA ACT GCG GAT CCA CTC ACC TAG GAC GGT CAG CTT GGT GCC-3' (SEQ ID NO: 91) |
| VNJH1-2FORBam | 5'-CGA GTC ATT CTG CAC TTG GAT CCA CTC ACC TGA GGA GAC GGT GAC CAG GGT CCC-3' (SEQ ID NO: 92) |

TABLE 1-continued

Oligonucleotide primers used in the identification and characterisation of TGF-b1 antibodies.

| Primer | Nucleotide sequence 5' to 3' | |
|---|---|---|
| Vκ2BackEuApa | 5'-AGC TCG GTC CTC GCA ACT GGT GTG CAC TCC GAT GTT GTG ATG ACT CAG TCT CC-3' | (SEQ ID NO: 93) |
| HuJκForEuBam | 5'-G GTC CTC GCA ACT GCG GAT CCA CTC ACG TTT GAT ATC CAC TTT GGT CCC 3' | (SEQ ID NO: 94) |
| Vλ3BackEuApa | 5'-AGC TCG GTC CTC GCA ACT GGT GTG CAC TCC TCG TCT GAG CTG ACT CAG GAC CC-3' | (SEQ ID NO: 95) |
| LamDeltaBamHI | 5'-C CGG CCC TCA GGA ATC CCA GAC CGA TTC TC-3' | (SEQ ID NO: 96) |
| P10 | 5'-CTA AGC TTA CTG AGC ACA CAG GAC CTC ACC-3' | (SEQ ID NO: 97) |
| P16 | 5'-TTT GGA TAT CTC TCC ACA GGT GTC CAC TCC GAG GTG CAG CTG GTG GAG TCT G-3' | (SEQ ID NO: 98) |
| P17 | 5'-ATG GGC CCT TGG TGG AAG CTG AAG AGA CGG TGA CCA GGG TGC C-3' | (SEQ ID NO: 99) |
| P19 | 5'-TTG AAT TCA GGT GGG GGC ACT TCT CCC TCT ATG AAC ATT CCG TAG GGG CCA CTG TCT TC-3' | (SEQ ID NO: 100) |
| P22 | 5'-TTA ACG ATT TCG AAC GCC ACC ATG GGA TGG AGC TGT ATC ATC CTC-3' | (SEQ ID NO: 101) |
| P25 | 5'-GTC CTA GGT GAG TAG ATC TAT CTG GGA TAA GCA TGC TGT TTT C-3' | (SEQ ID NO: 102) |
| P26 | 5'-GAT CTA CTC ACC TAG GAC GGT CAG CTT GG-3' | (SEQ ID NO: 103) |

TABLE 2

Properties of single chain Fv fragments for binding to TGFbeta1 or TGFbeta2 determined using BIACore

| Antibody | koff (s$^{-1}$) | $K_d$(nM) |
|---|---|---|
| TGFbeta1 | | |
| 31G9 | $9.0 \times 10^{-4}$ | 12 |
| CS32 | $1.2 \times 10^{-3}$ | |
| CS39 | $1.7 \times 10^{-3}$ | |
| TGFbeta2 | | |
| 6A5 | $1.4 \times 10^{-4}$ | 0.7 |
| 6B1 | $6.0 \times 10^{-4}$ | |
| 6H1 | $1.1 \times 10^{-3}$ | |
| 14F12 | $2.1 \times 10^{-3}$ | |

TABLE 3

Daily dose levels for individual animals in each group

| Group | Clone | Antibody format | Antigen | Dose |
|---|---|---|---|---|
| 1 | Saline Control | — | — | — |
| 2 | 31G9 | scFv | TGF β$_1$ | 20 ng |
| 3 | 6A5 | scFv | TGF β$_2$ | 20 ng |
| 4 | 27C1/10A6 | IgG4 | TGF β$_1$ | 692 ng |
| 5 | 6H1 | IgG4 | TGF β$_2$ | 1.76 μg |
| 6 | 31G9 + 6A5 | scFv's | TGF β$_1$ TGF β$_2$ | 20 ng " |
| 7 | 27C1/10A6 + 6H1 | IgG4's | TGF β$_1$ TGF β$_2$ | 692 ng 1.76 μg |

TABLE 4

I.C.$_{50}$ values for antibodies in TF1 assay

| Antibody | scFv (nM) | IgG4 (nM) |
|---|---|---|
| 6H1 | 1.5 | 100 |
| 6B1 | 15 | 11 |
| 6A5 | 8 | 150 |
| 14F12 | 90 | nd | nd = not determined

TABLE 5

IC$_{50}$ values for antibodies measured using a.radioreceptor assay.

|  | IC$_{50}$, nM |
|---|---|
| Anti-TGF-β1 antibody | |
| 7A3 scFv | >100 |
| 31G9 scFv | 30 |
| CS32 scFv | 4.5 |
| CS39 scFv | ~60 |
| 27C1/10A6 IgG | 9 |
| VT37 scFv. | ~100 |
| Anti-TGF-β2 antibody | |
| 6A5 scFv | 1.5 |
| 6A5 IgG | ~6 |
| 6B1 scFv | 0.3 |
| 6B1 IgG | 0.6 |
| 6H1 scFv | 0.22 |
| 6H1 IgG | ~10 |
| 11E6 IgG | 1.6 |
| 14F12 scFv | 3 |
| VT37 scFv | 2 |

TABLE 6

Potency of neutralisation of TGFbeta isoforms

|  | 6B1 IgG4 | Genzyme |
|---|---|---|
| TF1 cell proliferation assay IC$_{50}$ (nM IgG) | | |
| TGFbeta1 | >100 | 1.5 |
| TGFbeta2 | 2 | 10 |
| TGFbeta3 | 11 | 0.1 |
| A549 cell radioreceptor assay IC$_{50}$ (nM IgG) | | |
| TGFbeta1 | >400 | 0.55 |
| TGFbeta2 | 0.05 | 0.5 |
| TGFbeta3 | 4 | 0.03 |

TABLE 7

Kinetic parameters of 6B1 IgG4 and 6B1 single chain Fv

| antibody format | antigen | k$_{off}$ s$^{-1}$ | k$_{on}$ M$^{-1}$s$^{-1}$ | dissociation constant K$_d$ nM |
|---|---|---|---|---|
| 6B1 scFv | TGFβ2 | 6.68 × 10$^{-4}$ | 2.87 × 10$^5$ | 2.32 |
| 6B1 IgG4 | TGFβ2 | 3.36 × 10$^{-4}$ | 3.84 × 10$^5$ | 0.89 |
| 6B1 IgG4 | TGFβ3 | 4.5 × 10$^{-4}$ | 4.5 × 10$^4$ | 10.0 |

TABLE 8

Peptide sequences from phage binding to 6B1 IgG4
This table shows the amino acid sequence of 4 phage peptide display clones that show a match with the sequence of TGFbeta2. These clones have been lined up below the relevant part of the sequence of TGFbeta2, which is shown from amino acid positions 56 to 77.

| | | |
|---|---|---|
| TGFbeta2 | TQHSRVLSLYNTINPEASASPC | (SEQ ID NO: 104) |
| Clone 1 | RQLSLQQRMH | (SEQ ID NO: 105) |
| Clone 2 | DPMDMVLKLC | (SEQ ID NO: 106) |
| Clone 3 | WSEFMRQSSL | (SEQ ID NO: 107) |
| Clone 3 | VESTSLQFRG | (SEQ ID NO: 108) |

TABLE 9

Binding of peptides from TGFbeta to 6B1 IgG4 immobilised on a BIACore chip

| peptide | concentration of peptide, μM | amount of binding to 6B1 IgG4 surface, RU |
|---|---|---|
| TGFβ2$_{56-69}$ | 537 | 1012.8 |
| TGFβ1$_{56-69}$ | 524 | 190.7 |
| irrelevant peptide | 745 | 60.9 |

SEQUENCE LISTING

<160> NUMBER OF SEQ ID NOS: 125

<210> SEQ ID NO 1
<211> LENGTH: 5
<212> TYPE: PRT
<213> ORGANISM: Human

<400> SEQUENCE: 1

Arg Val Leu Ser Leu
1               5

<210> SEQ ID NO 2
<211> LENGTH: 14
<212> TYPE: PRT
<213> ORGANISM: Human

<400> SEQUENCE: 2

Thr Gln His Ser Arg Val Leu Ser Leu Tyr Asn Thr Ile Asn
1               5                   10

```
<210> SEQ ID NO 3
<211> LENGTH: 17
<212> TYPE: PRT
<213> ORGANISM: Human

<400> SEQUENCE: 3

Cys Gly Gly Thr Gln Tyr Ser Lys Val Leu Ser Leu Tyr Asn Gln His
1               5                   10                  15

Asn

<210> SEQ ID NO 4
<211> LENGTH: 14
<212> TYPE: PRT
<213> ORGANISM: Human

<400> SEQUENCE: 4

Thr Gln Tyr Ser Lys Val Leu Ser Leu Tyr Asn Gln His Asn
1               5                   10

<210> SEQ ID NO 5
<211> LENGTH: 345
<212> TYPE: DNA
<213> ORGANISM: Human

<400> SEQUENCE: 5
gaggtgcagc tggtggagtc tgggggaggc gtggtccagc ctggggaggtc cctgagactc        60 tcctgtgcag cgtctggatt caccttcagt agctatggca tgcactgggt ccgccaggct       120
ccaggcaagg ggctggagtg ggtggcagtt atatggtatg atggaagtaa taaatactat       180
gcagactccg tgaagggccg attcaccatc tccagagaca attccaagaa cacgctgtat       240
ctgcaaatgg acagcctgag agccgaggac acggccgtgt attactgtgg aagaacgctg       300
gagtctagtt tgtggggcca aggcacccctg gtcaccgtct cctca                     345

<210> SEQ ID NO 6
<211> LENGTH: 115
<212> TYPE: PRT
<213> ORGANISM: Human

<400> SEQUENCE: 6

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Gly Arg Thr Leu Glu Ser Ser Leu Trp Gly Gln Gly Thr Leu Val Thr
            100                 105                 110

Val Ser Ser
        115

<210> SEQ ID NO 7
<211> LENGTH: 369
```

<212> TYPE: DNA
<213> ORGANISM: Human

<400> SEQUENCE: 7

```
caggtgcaac tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaaactggg     300
gaatatagtg gctacgattc tagtggtgtg gacgtctggg gcaaagggac cacggtcacc     360
gtctcctca                                                             369
```

<210> SEQ ID NO 8
<211> LENGTH: 123
<212> TYPE: PRT
<213> ORGANISM: Human

<400> SEQUENCE: 8

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Thr Gly Glu Tyr Ser Gly Tyr Asp Ser Ser Gly Val Asp Val
            100                 105                 110
Trp Gly Lys Gly Thr Thr Val Thr Val Ser Ser
        115                 120
```

<210> SEQ ID NO 9
<211> LENGTH: 369
<212> TYPE: DNA
<213> ORGANISM: Human

<400> SEQUENCE: 9

```
caggtgcagc tggtgcagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtat taaatactat     180
gcagactccg tgaagggccg attcaccatc tccagagaca attccaagaa cacgctgtat     240
ctgcaaatga acagcctgag agctgaggac acggctgtgt attactgtgc gcgaactggt     300
gaatatagtg gctacgatac gagtggtgtg gagctctggg ggcaagggac cacggtcacc     360
gtctcctca                                                             369
```

<210> SEQ ID NO 10
<211> LENGTH: 123
<212> TYPE: PRT
<213> ORGANISM: Human

<400> SEQUENCE: 10

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Ser Gly Val Glu Leu
            100                 105                 110

Trp Gly Gln Gly Thr Thr Val Thr Val Ser Ser
        115                 120

<210> SEQ ID NO 11
<211> LENGTH: 369
<212> TYPE: DNA
<213> ORGANISM: Human

<400> SEQUENCE: 11
caggtgcaac tggtggagtc tggggggaggc gtggtccagc ctgggaggtc cctgagactc      60
tcctgtgcag cctctggact caccttcagt agctatgaca tgcactgggt ccgccagcct     120
ccagccaagg ggctggagtg ggtggcagtt atatcatatg atggaagtag taaatactat     180
gcagactccg tgaagggccg attcaccatc tccagagaca attccaagaa cacgctgtat     240
ctgcaaatga acagcctgag agctgaggac acggctgtgt attactgtgc gcgaactggt     300
gaatatagtg gctacgacac gagtggtgtg gagctctggg ggcaagggac cacggtcacc     360
gtctcctca                                                             369

<210> SEQ ID NO 12
<211> LENGTH: 123
<212> TYPE: PRT
<213> ORGANISM: Human

<400> SEQUENCE: 12

Gln Val Gln Leu Val Glu Ser Gly Gly Val Val Gln Pro Gly Arg
1               5                   10                  15

Ser Leu Arg Leu Ser Cys Ala Ala Ser Gly Leu Thr Phe Ser Ser Tyr
            20                  25                  30

Asp Met His Trp Val Arg Gln Pro Pro Ala Lys Gly Leu Glu Trp Val
        35                  40                  45

Ala Val Ile Ser Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Ser Gly Val Glu Leu
            100                 105                 110

Trp Gly Gln Gly Thr Thr Val Thr Val Ser Ser
        115                 120

<210> SEQ ID NO 13
<211> LENGTH: 324
<212> TYPE: DNA
<213> ORGANISM: Human

<400> SEQUENCE: 13

```
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttacagta ccccgtggac gttcggccaa     300
gggaccaagc tggagatcaa acgt                                            324
```

<210> SEQ ID NO 14
<211> LENGTH: 108
<212> TYPE: PRT
<213> ORGANISM: Human

<400> SEQUENCE: 14

```
Asp Ile Val Met Thr Gln Ser Pro Ser Thr Leu Ser Ala Ser Val Gly
1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg
            100                 105
```

<210> SEQ ID NO 15
<211> LENGTH: 342
<212> TYPE: DNA
<213> ORGANISM: Human

<400> SEQUENCE: 15

```
gacatcgtga tgacccagtc tccagactcc ctggctgtgt ctctgggcga gagggccacc      60
atcaactgca agtccagcca gagtctttta tacagctaca caagatgaa ctacttagct     120 tggtaccagc agaaaccagg acagcctcct aagctgctca ttaactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatgcaact     300
cctctgacgt tcggccacgg gaccaaggtg gaaatcaaac gt                        342
```

<210> SEQ ID NO 16
<211> LENGTH: 114
<212> TYPE: PRT
<213> ORGANISM: Human

<400> SEQUENCE: 16

```
Asp Ile Val Met Thr Gln Ser Pro Asp Ser Leu Ala Val Ser Leu Gly
```

```
                1               5                    10                   15
Glu Arg Ala Thr Ile Asn Cys Lys Ser Ser Gln Ser Leu Leu Tyr Ser
                    20                   25                   30

Tyr Asn Lys Met Asn Tyr Leu Ala Trp Tyr Gln Gln Lys Pro Gly Gln
                    35                   40                   45

Pro Pro Lys Leu Leu Ile Asn Trp Ala Ser Thr Arg Glu Ser Gly Val
        50                   55                   60

Pro Asp Arg Phe Ser Gly Ser Gly Ser Gly Thr Asp Phe Thr Leu Thr
65                       70                   75                   80

Ile Ser Ser Leu Gln Ala Glu Asp Val Ala Val Tyr Tyr Cys Gln Gln
                    85                   90                   95

Tyr Tyr Ala Thr Pro Leu Thr Phe Gly His Gly Thr Lys Val Glu Ile
                100                  105                  110

Lys Arg

<210> SEQ ID NO 17
<211> LENGTH: 330
<212> TYPE: DNA
<213> ORGANISM: Human

<400> SEQUENCE: 17
cacgttatac tgactcagga ccctgctgtg tctgtggcct tgggacagac agtcaggatc       60
acgtgccaag agacagcct caaaagctac tatgcaagtt ggtaccagca gaagccagga      120 caggccccctg tacttgtcat ctatggtgaa aacagccggc cctccgggat cccagaccga    180
ttctctggct ccagctcagg aaacacagct tccttgacca tcactggggc tcaggcggaa    240
gatgaagctg actattactg taactcccgg gacagcagtg gtacccatct agaagtgttc    300
ggcggaggga ccaagctgac cgtcctaggt                                      330

<210> SEQ ID NO 18
<211> LENGTH: 110
<212> TYPE: PRT
<213> ORGANISM: Human

<400> SEQUENCE: 18

His Val Ile Leu Thr Gln Asp Pro Ala Val Ser Val Ala Leu Gly Gln
1               5                    10                   15

Thr Val Arg Ile Thr Cys Gln Gly Asp Ser Leu Lys Ser Tyr Tyr Ala
                    20                   25                   30

Ser Trp Tyr Gln Gln Lys Pro Gly Gln Ala Pro Val Leu Val Ile Tyr
                    35                   40                   45

Gly Glu Asn Ser Arg Pro Ser Gly Ile Pro Asp Arg Phe Ser Gly Ser
        50                   55                   60

Ser Ser Gly Asn Thr Ala Ser Leu Thr Ile Thr Gly Ala Gln Ala Glu
65                       70                   75                   80

Asp Glu Ala Asp Tyr Tyr Cys Asn Ser Arg Asp Ser Ser Gly Thr His
                    85                   90                   95

Leu Glu Val Phe Gly Gly Gly Thr Lys Leu Thr Val Leu Gly
                100                  105                  110

<210> SEQ ID NO 19
<211> LENGTH: 17
<212> TYPE: PRT
<213> ORGANISM: Human

<400> SEQUENCE: 19
```

```
Ala Arg Thr Gly Glu Tyr Ser Gly Tyr Asp Ser Ser Gly Val Asp Val
1               5                   10                  15

Trp

<210> SEQ ID NO 20
<211> LENGTH: 17
<212> TYPE: PRT
<213> ORGANISM: Human

<400> SEQUENCE: 20

Ala Arg Thr Gly Glu Tyr Ser Gly Tyr Asp Thr Ser Gly Val Glu Leu
1               5                   10                  15

Trp

<210> SEQ ID NO 21
<211> LENGTH: 17
<212> TYPE: PRT
<213> ORGANISM: Human

<400> SEQUENCE: 21

Ala Arg Thr Arg Glu Tyr Ser Gly His Asp Ser Ser Gly Val Asp Asp
1               5                   10                  15

Trp

<210> SEQ ID NO 22
<211> LENGTH: 17
<212> TYPE: PRT
<213> ORGANISM: Human

<400> SEQUENCE: 22

Ala Arg Thr Gly Pro Phe Ser Gly Tyr Asp Ser Ser Gly Glu Asp Val
1               5                   10                  15

Arg

<210> SEQ ID NO 23
<211> LENGTH: 17
<212> TYPE: PRT
<213> ORGANISM: Human

<400> SEQUENCE: 23

Ala Arg Thr Glu Glu Tyr Ser Gly Tyr Asp Ser Ser Gly Val Asp Val
1               5                   10                  15

Trp

<210> SEQ ID NO 24
<211> LENGTH: 17
<212> TYPE: PRT
<213> ORGANISM: Human

<400> SEQUENCE: 24

Ala Gln Thr Arg Glu Tyr Thr Gly Tyr Asp Ser Ser Gly Val Asp Val
1               5                   10                  15

Trp

<210> SEQ ID NO 25
<211> LENGTH: 17
<212> TYPE: PRT
<213> ORGANISM: Human

<400> SEQUENCE: 25

Ala Arg Thr Glu Glu Tyr Ser Gly Phe Asp Ser Thr Gly Glu Asp Val
```

```
1               5                   10                  15

Trp

<210> SEQ ID NO 26
<211> LENGTH: 17
<212> TYPE: PRT
<213> ORGANISM: Human

<400> SEQUENCE: 26

Ala Arg Thr Glu Glu Phe Ser Gly Tyr Asp Ser Ser Gly Val Asp Val
1               5                   10                  15

Trp

<210> SEQ ID NO 27
<211> LENGTH: 17
<212> TYPE: PRT
<213> ORGANISM: Human

<400> SEQUENCE: 27

Ala Arg Thr Gly Glu Tyr Ser Gly Tyr His Ser Ser Gly Val Asp Val
1               5                   10                  15

Arg

<210> SEQ ID NO 28
<211> LENGTH: 17
<212> TYPE: PRT
<213> ORGANISM: Human

<400> SEQUENCE: 28

Ala Arg Thr Glu Glu Phe Ser Gly Tyr Asp Ser Ser Gly Val Asp Val
1               5                   10                  15

Trp

<210> SEQ ID NO 29
<211> LENGTH: 17
<212> TYPE: PRT
<213> ORGANISM: Human

<400> SEQUENCE: 29

Ala Arg Ala Gly Pro Phe Ser Gly Tyr Asp Ser Ser Gly Glu Asp Val
1               5                   10                  15

Arg

<210> SEQ ID NO 30
<211> LENGTH: 17
<212> TYPE: PRT
<213> ORGANISM: Human

<400> SEQUENCE: 30

Ala Arg Thr Gly Pro Phe Ser Gly Tyr Asp Ser Ser Gly Glu Asp Val
1               5                   10                  15

Trp

<210> SEQ ID NO 31
<211> LENGTH: 17
<212> TYPE: PRT
<213> ORGANISM: Human

<400> SEQUENCE: 31

Ala Arg Thr Glu Glu Phe Ser Gly Tyr Asp Ser Ser Gly Val Asp Val
1               5                   10                  15
```

<210> SEQ ID NO 32
<211> LENGTH: 17
<212> TYPE: PRT
<213> ORGANISM: Human

<400> SEQUENCE: 32

Ala Arg Thr Gly Glu Tyr Ser Gly Tyr Asp Ser Ser Gly Glu Leu Val
1               5                   10                  15

Trp

<210> SEQ ID NO 33
<211> LENGTH: 17
<212> TYPE: PRT
<213> ORGANISM: Human

<400> SEQUENCE: 33

Ala Arg Thr Glu Glu Phe Ser Gly Tyr Asp Ser Thr Gly Glu Glu Val
1               5                   10                  15

Trp

<210> SEQ ID NO 34
<211> LENGTH: 17
<212> TYPE: PRT
<213> ORGANISM: Human

<400> SEQUENCE: 34

Ala Arg Thr Glu Glu Phe Ser Gly Tyr Asp Ser Ser Gly Val Asp Val
1               5                   10                  15

Trp

<210> SEQ ID NO 35
<211> LENGTH: 17
<212> TYPE: PRT
<213> ORGANISM: Human

<400> SEQUENCE: 35

Ala Arg Thr Gly Glu Tyr Ser Gly Tyr Asp Ser Ser Gly Glu Asp Val
1               5                   10                  15

Trp

<210> SEQ ID NO 36
<211> LENGTH: 350
<212> TYPE: DNA
<213> ORGANISM: Human

<400> SEQUENCE: 36
gagattcagc tggtggagtc tgggggaggc gtggtccagc ctgggagatc cctgagactc      60
tcctgtgcag cctctggatt caccttcagt agctatgcta tgcactgggt ccgccaggct     120
ccagccaagg ggctggagtg gtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggccgtgt attactgtgc aagagcgggg     300
ttggaaacga cgtggggcca aggaaccctg gtcaccgtct cctcaagtgg                350

<210> SEQ ID NO 37
<211> LENGTH: 117
<212> TYPE: PRT

<213> ORGANISM: Human

<400> SEQUENCE: 37

Glu Ile Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Ala Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Glu Thr Thr Trp Gly Gln Gly Thr Leu Val Thr
            100                 105                 110

Val Ser Ser Gly
        115

<210> SEQ ID NO 38
<211> LENGTH: 324
<212> TYPE: DNA
<213> ORGANISM: Human

<400> SEQUENCE: 38
gatgttgtga tgactcagtc tccatcctcc ctgtctgcat ctgtaggaga cagagtcacc      60
atcacttgcc gggccagtca gggcattagc aattatttag cctggtatca gcaaaaacca     120
gggaaagccc ctaagctcct gatctataag gcatctactt tagaaagtgg ggtcccatca     180
aggttcagtg gcagtggatc tgggacagaa ttcactctca caatcagcag tctgcaacct     240
gaagattttg caacttacta ctgtcaacag agttacagta cccctcgaac gttcggccaa     300
gggaccaaag tggatatcaa acgt                                            324

<210> SEQ ID NO 39
<211> LENGTH: 108
<212> TYPE: PRT
<213> ORGANISM: Human

<400> SEQUENCE: 39

Asp Val Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Asp Ile Lys Arg
            100                 105

<210> SEQ ID NO 40

<211> LENGTH: 327
<212> TYPE: DNA
<213> ORGANISM: Human

<400> SEQUENCE: 40

```
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcaggat cccagaccga   180
ttcgctggct ccaactcagg aaacacagct tccttgacca tcactggggc tcaggcggag   240
gatgaggctg actattactg tagctcccgg gacagcagtg gtaaccatgt ggttttcggc   300
ggagggacca agctgaccgt cctaggt                                      327
```

<210> SEQ ID NO 41
<211> LENGTH: 109
<212> TYPE: PRT
<213> ORGANISM: Human

<400> SEQUENCE: 41

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ala Gly Ser
     50                  55                  60

Asn Ser Gly Asn Thr Ala Ser Leu Thr Ile Thr Gly Ala Gln Ala Glu
 65                  70                  75                  80

Asp Glu Ala Asp Tyr Tyr Cys Ser Ser Arg Asp Ser Ser Gly Asn His
                 85                  90                  95

Val Val Phe Gly Gly Gly Thr Lys Leu Thr Val Leu Gly
            100                 105
```

<210> SEQ ID NO 42
<211> LENGTH: 330
<212> TYPE: DNA
<213> ORGANISM: Human

<400> SEQUENCE: 42

```
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcaggat cccagaccga   180
ttctctggct ccagctcagg aaacacagct tccttgacca tcactggggc tcaggcggaa   240
gatgaggctg actattactg taactcccgg gacagcagta gtacccatcg aggggtgttc   300
ggcggaggga ccaagctgac cgtcctaggt                                   330
```

<210> SEQ ID NO 43
<211> LENGTH: 110
<212> TYPE: PRT
<213> ORGANISM: Human

<400> SEQUENCE: 43

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
```

-continued

```
                20                  25                  30
Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Thr His
                 85                  90                  95

Arg Gly Val Phe Gly Gly Gly Thr Lys Leu Thr Val Leu Gly
            100                 105                 110

<210> SEQ ID NO 44
<211> LENGTH: 324
<212> TYPE: DNA
<213> ORGANISM: Human

<400> SEQUENCE: 44
gaagttgtgc tgactcagtc tccatcctcc ctgtctgcat ctgtaggaga cagagtcacc    60
atcacttgcc gggcaagtca gggcattgga gatgatttgg gctggtatca gcagaagcca   120
gggaaagccc ctatcctcct gatctatggt acatccactt tacaaagtgg ggtcccgtca   180
aggttcagcg gcagtggatc tggcacagat ttcactctca ccatcaacag cctgcagcct   240
gaagattttg caacttatta ctgtctacaa gattccaatt acccgctcac tttcggcgga   300
gggacacgac tggagattaa acgt                                          324

<210> SEQ ID NO 45
<211> LENGTH: 108
<212> TYPE: PRT
<213> ORGANISM: Human

<400> SEQUENCE: 45

Glu Val Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
             20                  25                  30

Leu Gly Trp Tyr Gln Gln Lys Pro Gly Lys Ala Pro Ile Leu Leu Ile
         35                  40                  45

Tyr Gly Thr Ser Thr Leu Gln Ser Gly Val Pro Ser Arg Phe Ser Gly
     50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                 85                  90                  95

Thr Phe Gly Gly Gly Thr Arg Leu Glu Ile Lys Arg
            100                 105

<210> SEQ ID NO 46
<211> LENGTH: 321
<212> TYPE: DNA
<213> ORGANISM: Human

<400> SEQUENCE: 46
tcgtctgagc tgactcagga ccctgctgtg tctgtggcct tgggacagac agtcaggatc    60
acatgccaag agacagcct cagaaactat tatgcaaact ggtaccagca gaagccagga   120
caggcccctg tacttgtcat ctatggtaaa aacaaccggc cctcagggat cccagaccga   180
```

```
ttctctggct ccagctcagg gaacacagct tccttgacca tcactggggc tcgggcggaa      240 gatgaggtg tctattactg taactcccgg gacagcagtg gtgcggtttt cggcggaggg      300
accaagctga ccgtcctagg t                                               321
```

<210> SEQ ID NO 47
<211> LENGTH: 107
<212> TYPE: PRT
<213> ORGANISM: Human

<400> SEQUENCE: 47

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Asn Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Arg Ala Glu
65                  70                  75                  80

Asp Glu Gly Val Tyr Tyr Cys Asn Ser Arg Asp Ser Ser Gly Ala Val
                85                  90                  95

Phe Gly Gly Gly Thr Lys Leu Thr Val Leu Gly
            100                 105
```

<210> SEQ ID NO 48
<211> LENGTH: 327
<212> TYPE: DNA
<213> ORGANISM: Human

<400> SEQUENCE: 48

```
tcgtctgagc tgactcagga ccctgctgtg tctgtggcct tgggacagac agttaggatc      60
acttcccaag agacagtct cagaagctat tacacaaact ggtttcagca gaagccagga      120 cagcccctc tacttgtcgt ctatgctaaa aataagcggc cctcagggat cccagaccga      180
ttctctggct ccagctcagg aaacacagct tccttgacca tcactggggc tcaggcggaa      240
gatgaggctg actattactg tcattcccgg gacagcagtg gtaaccatgt gcttttcggc      300
ggagggacca agctgaccgt cctaggt                                         327
```

<210> SEQ ID NO 49
<211> LENGTH: 109
<212> TYPE: PRT
<213> ORGANISM: Human

<400> SEQUENCE: 49

```
Ser Ser Glu Leu Thr Gln Asp Pro Ala Val Ser Val Ala Leu Gly Gln
1               5                   10                  15

Thr Val Arg Ile Thr Ser Gln Gly Asp Ser Leu Arg Ser Tyr Tyr Thr
            20                  25                  30

Asn Trp Phe Gln Gln Lys Pro Gly Gln Pro Pro Leu Leu Val Val Tyr
        35                  40                  45

Ala Lys Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80
```

Asp Glu Ala Asp Tyr Tyr Cys His Ser Arg Asp Ser Ser Gly Asn His
            85                  90                  95

Val Leu Phe Gly Gly Gly Thr Lys Leu Thr Val Leu Gly
            100                 105

<210> SEQ ID NO 50
<211> LENGTH: 144
<212> TYPE: DNA
<213> ORGANISM: Human

<400> SEQUENCE: 50
aagcttgccg ccaccatgga ctggacctgg cgcgtgtttt gcctgctcgc cgtggcccct     60
ggggcccaca gccaggtgca actgcagcag tccggtgcca agggaccacg gtcaccgtct    120
cctcaggtga gtggatccga attc                                          144

<210> SEQ ID NO 51
<211> LENGTH: 48
<212> TYPE: PRT
<213> ORGANISM: Human

<400> SEQUENCE: 51

Lys Leu Ala Ala Thr Met Asp Trp Thr Trp Arg Val Phe Cys Leu Leu
1               5                   10                  15

Ala Val Ala Pro Gly Ala His Ser Gln Val Gln Leu Gln Gln Ser Gly
            20                  25                  30

Ala Lys Gly Pro Arg Ser Pro Ser Pro Gln Val Ser Gly Ser Glu Phe
        35                  40                  45

<210> SEQ ID NO 52
<211> LENGTH: 144
<212> TYPE: DNA
<213> ORGANISM: Human

<400> SEQUENCE: 52
gaattcggat ccactcacct gaggagacgg tgaccgtggt cccttggcac cggactgctg     60
cagttgcacc tggctgtggg ccccaggggc cacggcgagc aggcaaaaca cgcgccaggt    120
ccagtccatg gtggcggcaa gctt                                          144

<210> SEQ ID NO 53
<211> LENGTH: 234
<212> TYPE: DNA
<213> ORGANISM: Human

<400> SEQUENCE: 53
aagcttcgcc accatgggat ggagctgtat catcctcttc ttggtagcaa cagctacagg     60 taagggctc acagtagcag cttgaggtc tggacatata tatgggtgac aatgacatcc      120
actttgcctt tctctccaca ggtgtgcact ccgacattga gctcacccag tctccagaca    180
aagctcgagc tgaaacgtga gtagaattta aactttgctt cctcaattgg atcc          234

<210> SEQ ID NO 54
<211> LENGTH: 15
<212> TYPE: PRT
<213> ORGANISM: Human

<400> SEQUENCE: 54

Met Gly Trp Ser Cys Ile Ile Leu Phe Leu Val Ala Thr Ala Thr
1               5                   10                  15

<210> SEQ ID NO 55
<211> LENGTH: 8
<212> TYPE: PRT
<213> ORGANISM: Human

<400> SEQUENCE: 55

Gly Val His Ser Asp Ile Glu Leu
1               5

<210> SEQ ID NO 56
<211> LENGTH: 4
<212> TYPE: PRT
<213> ORGANISM: Human

<400> SEQUENCE: 56

Leu Glu Leu Lys
1

<210> SEQ ID NO 57
<211> LENGTH: 234
<212> TYPE: DNA
<213> ORGANISM: Human

<400> SEQUENCE: 57

```
ggatccaatt gaggaagcaa agtttaaatt ctactcacgt ttcagctcga gctttgtctg    60
gagactgggt gagctcaatg tcggagtgca cacctgtgga gagaaaggca aagtggatgt   120
cattgtcacc catatatatg tccagacctc aagcctgcta ctgtgagccc cttacctgta   180
gctgttgcta ccaagaagag gatgatacag ctccatccca tggtggcgaa gctt         234
```

<210> SEQ ID NO 58
<211> LENGTH: 324
<212> TYPE: DNA
<213> ORGANISM: Human

<400> SEQUENCE: 58

```
gaaattgtgc tgactcagtc tccatcctcc ctgtctgcat ctgtaggaga cagagtcacc    60
atcacttgcc gggcaagtca gggcattgga gatgatttgg gctggtatca gcagaagcca   120
gggaaagccc ctatcctcct gatctatggt acatccactt acaaagtggg gtcccgtca   180
aggttcagcg gcagtggatc tggcacagat ttcactctca ccatcaacag cctgcagcct   240
gaagattttg caacttatta ctgtctacaa gattccaatt acccgctcac tttcggcgga   300
gggacacgac tggagattaa acgt                                          324
```

<210> SEQ ID NO 59
<211> LENGTH: 108
<212> TYPE: PRT
<213> ORGANISM: Human

<400> SEQUENCE: 59

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95
Thr Phe Gly Gly Gly Thr Arg Leu Glu Ile Lys Arg
            100                 105

<210> SEQ ID NO 60
<211> LENGTH: 345
<212> TYPE: DNA
<213> ORGANISM: Human

<400> SEQUENCE: 60
gaggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatgg acagcctgag agccgaggac acggccgtgt attactgtgg aagaacgctg   300
gagtctagtt tgtggggcca aggcacccctg gtcaccgtct cctca                  345

<210> SEQ ID NO 61
<211> LENGTH: 115
<212> TYPE: PRT
<213> ORGANISM: Human

<400> SEQUENCE: 61

Glu Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asp Ser Leu Arg Ala Glu Asp Thr Ala Val Tyr Tyr Cys
                85                  90                  95
Gly Arg Thr Leu Glu Ser Ser Leu Trp Gly Gln Gly Thr Leu Val Thr
            100                 105                 110
Val Ser Ser
        115

<210> SEQ ID NO 62
<211> LENGTH: 330
<212> TYPE: DNA
<213> ORGANISM: Human

<400> SEQUENCE: 62
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactggggc tcaggcggaa   240
gatgaggctg actattactg taactcccgg gacagcagta gtacccatcg aggggtgttc   300
ggcggaggga ccaagctgac cgtcctaggt                                    330

<210> SEQ ID NO 63
<211> LENGTH: 110
<212> TYPE: PRT
<213> ORGANISM: Human

<400> SEQUENCE: 63

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Thr His
                85                  90                  95

Arg Gly Val Phe Gly Gly Gly Thr Lys Leu Thr Val Leu Gly
            100                 105                 110

<210> SEQ ID NO 64
<211> LENGTH: 327
<212> TYPE: DNA
<213> ORGANISM: Human

<400> SEQUENCE: 64
tcgtctgagc tgactcagga ccctgctgtg tctgtggcct tgggacagac agtcaggatc      60
acatgccaag agacagcct cagaagctat tatgcaagct ggtaccagca aaagccagga     120
caggcccctg tacttgtcat ctatggtaaa aacaaccggc cctcagggat cccagaccga     180
ttcgctggct ccaactcagg aaacacagct tccttgacca tcactggggc tcaggcggag     240
gatgaggctg actattactg tagctcccgg gacagcagtg gtaaccatgt ggttttcggc     300
ggagggacca agctgaccgt cctaggt                                         327

<210> SEQ ID NO 65
<211> LENGTH: 109
<212> TYPE: PRT
<213> ORGANISM: Human

<400> SEQUENCE: 65

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ala Gly Ser
    50                  55                  60

Asn Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Val Val Phe Gly Gly Gly Thr Lys Leu Thr Val Leu Gly
            100                 105

```
<210> SEQ ID NO 66
<211> LENGTH: 324
<212> TYPE: DNA
<213> ORGANISM: Human

<400> SEQUENCE: 66
gatgttgtga tgactcagtc tccatcctcc ctgtctgcat ctgtaggaga cagagtcacc      60
atcacttgcc gggccagtca gggcattagc aattatttag cctggtatca gcaaaaacca     120
gggaaagccc ctaagctcct gatctataag gcatctactt tagaaagtgg ggtcccatca     180
aggttcagtg gcagtggatc tgggacagaa ttcactctca caatcagcag tctgcaacct     240
gaagattttg caacttacta ctgtcaacag agttacagta cccctcgaac gttcggccaa     300
gggaccaaag tggatatcaa acgt                                             324

<210> SEQ ID NO 67
<211> LENGTH: 108
<212> TYPE: PRT
<213> ORGANISM: Human

<400> SEQUENCE: 67

Asp Val Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Asp Ile Lys Arg
            100                 105

<210> SEQ ID NO 68
<211> LENGTH: 84
<212> TYPE: DNA
<213> ORGANISM: Recombinant

<400> SEQUENCE: 68
cgtggtccct ttgccccaga cgtccacacc actagaatcg tagccactat attcccagt       60 tcgcgcacag taatacacag ccgt                                              84

<210> SEQ ID NO 69
<211> LENGTH: 23
<212> TYPE: DNA
<213> ORGANISM: Recombinant

<400> SEQUENCE: 69
agcggataac aatttcacac agg                                               23

<210> SEQ ID NO 70
<211> LENGTH: 21
<212> TYPE: DNA
<213> ORGANISM: Recombinant

<400> SEQUENCE: 70
gtcgtctttc cagacgttag t                                                 21
```

<210> SEQ ID NO 71
<211> LENGTH: 21
<212> TYPE: DNA
<213> ORGANISM: Recombinant

<400> SEQUENCE: 71
accgccagag ccacctccgc c                                              21

<210> SEQ ID NO 72
<211> LENGTH: 21
<212> TYPE: DNA
<213> ORGANISM: Recombinant

<400> SEQUENCE: 72
ggcggaggtg gctctggcgg t                                              21

<210> SEQ ID NO 73
<211> LENGTH: 21
<212> TYPE: DNA
<213> ORGANISM: Recombinant

<400> SEQUENCE: 73
ctcttctgag atgagttttt g                                              21

<210> SEQ ID NO 74
<211> LENGTH: 24
<212> TYPE: DNA
<213> ORGANISM: Recombinant

<400> SEQUENCE: 74
tgaggagacg gtgaccaggg ttcc                                           24

<210> SEQ ID NO 75
<211> LENGTH: 68
<212> TYPE: DNA
<213> ORGANISM: Recombinant

<400> SEQUENCE: 75
gmaccctggt caccgtctcc tcaggtggag gcggttcagg cggaggtggc agcggcggtg    60
gcggatcg                                                             68

<210> SEQ ID NO 76
<211> LENGTH: 68
<212> TYPE: DNA
<213> ORGANISM: Recombinant

<400> SEQUENCE: 76
ggacaatggt caccgtctct tcaggtggag gcggttcagg cggaggtggc agcggcggtg    60
gcggatcg                                                             68

<210> SEQ ID NO 77
<211> LENGTH: 68
<212> TYPE: DNA
<213> ORGANISM: Recombinant

<400> SEQUENCE: 77
ggaccacggt caccgtctcc tcaggtggag gcggttcagg cggaggtggc agcggcggtg    60
gcggatcg                                                             68

<210> SEQ ID NO 78

<211> LENGTH: 56
<212> TYPE: DNA
<213> ORGANISM: Recombinant

<400> SEQUENCE: 78
gtcctcgcaa ctgcggccca gccggccatg gcccagrtgc agctggtgca rtctgg      56

<210> SEQ ID NO 79
<211> LENGTH: 56
<212> TYPE: DNA
<213> ORGANISM: Recombinant

<400> SEQUENCE: 79
gtcctcgcaa ctgcggccca gccggccatg gccsaggtcc agctggtrca gtctgg      56

<210> SEQ ID NO 80
<211> LENGTH: 56
<212> TYPE: DNA
<213> ORGANISM: Recombinant

<400> SEQUENCE: 80
gtcctcgcaa ctgcggccca gccggccatg gcccagrtca ccttgaagga gtctgg      56

<210> SEQ ID NO 81
<211> LENGTH: 56
<212> TYPE: DNA
<213> ORGANISM: Recombinant

<400> SEQUENCE: 81
gtcctcgcaa ctgcggccca gccggccatg gccsaggtgc agctggtgga gtctgg      56

<210> SEQ ID NO 82
<211> LENGTH: 56
<212> TYPE: DNA
<213> ORGANISM: Recombinant

<400> SEQUENCE: 82
gtcctcgcaa ctgcggccca gccggccatg gccgaggtgc agctggtgga gwcygg      56

<210> SEQ ID NO 83
<211> LENGTH: 56
<212> TYPE: DNA
<213> ORGANISM: Recombinant

<400> SEQUENCE: 83
gtcctcgcaa ctgcggccca gccggccatg gcccaggtgc agctacagca gtgggg      56

<210> SEQ ID NO 84
<211> LENGTH: 56
<212> TYPE: DNA
<213> ORGANISM: Recombinant

<400> SEQUENCE: 84
gtcctcgcaa ctgcggccca gccggccatg gcccagstgc agctgcagga gtcsgg      56

<210> SEQ ID NO 85
<211> LENGTH: 56
<212> TYPE: DNA
<213> ORGANISM: Recombinant

<400> SEQUENCE: 85
gtcctcgcaa ctgcggccca gccggccatg gccgargtgc agctggtgca gtctgg      56

```
<210> SEQ ID NO 86
<211> LENGTH: 56
<212> TYPE: DNA
<213> ORGANISM: Recombinant

<400> SEQUENCE: 86
gtcctcgcaa ctgcggccca gccggccatg gcccaggtac agctgcagca gtcagg        56

<210> SEQ ID NO 87
<211> LENGTH: 62
<212> TYPE: DNA
<213> ORGANISM: Recombinant

<400> SEQUENCE: 87
agctcggtcc tcgcaactgc ggccctggg gcccacagcg aggtgcagct ggtggagtct    60
gg                                                                    62

<210> SEQ ID NO 88
<211> LENGTH: 54
<212> TYPE: DNA
<213> ORGANISM: Recombinant

<400> SEQUENCE: 88
cgagtcattc tgcacttgga tccactcacc tgaggagacg gtgaccgtgg tccc          54

<210> SEQ ID NO 89
<211> LENGTH: 30
<212> TYPE: DNA
<213> ORGANISM: Recombinant

<400> SEQUENCE: 89
gagaatcggt ctgggattcc tgagggccgg                                      30

<210> SEQ ID NO 90
<211> LENGTH: 53
<212> TYPE: DNA
<213> ORGANISM: Recombinant

<400> SEQUENCE: 90
agctcggtcc tcgcaactgg tgtgcactcc cacgttatac tgactcagga ccc            53

<210> SEQ ID NO 91
<211> LENGTH: 49
<212> TYPE: DNA
<213> ORGANISM: Recombinant

<400> SEQUENCE: 91
ggtcctcgca actgcggatc cactcaccta ggacggtcag cttggtccc                 49

<210> SEQ ID NO 92
<211> LENGTH: 54
<212> TYPE: DNA
<213> ORGANISM: Recombinant

<400> SEQUENCE: 92
cgagtcattc tgcacttgga tccactcacc tgaggagacg gtgaccaggg tgcc           54

<210> SEQ ID NO 93
<211> LENGTH: 53
<212> TYPE: DNA
<213> ORGANISM: Recombinant

<400> SEQUENCE: 93
```
agctcggtcc tcgcaactgg tgtgcactcc gatgttgtga tgactcagtc tcc    53

<210> SEQ ID NO 94
<211> LENGTH: 49
<212> TYPE: DNA
<213> ORGANISM: Recombinant

<400> SEQUENCE: 94
ggtcctcgca actgcggatc cactcacgtt tgatatccac tttggtccc    49

<210> SEQ ID NO 95
<211> LENGTH: 53
<212> TYPE: DNA
<213> ORGANISM: Recombinant

<400> SEQUENCE: 95
agctcggtcc tcgcaactgg tgtgcactcc tcgtctgagc tgactcagga ccc    53

<210> SEQ ID NO 96
<211> LENGTH: 30
<212> TYPE: DNA
<213> ORGANISM: Recombinant

<400> SEQUENCE: 96
ccggccctca ggaatcccag accgattctc    30

<210> SEQ ID NO 97
<211> LENGTH: 30
<212> TYPE: DNA
<213> ORGANISM: Recombinant

<400> SEQUENCE: 97
ctaagcttac tgagcacaca ggacctcacc    30

<210> SEQ ID NO 98
<211> LENGTH: 52
<212> TYPE: DNA
<213> ORGANISM: Recombinant

<400> SEQUENCE: 98
tttggatatc tctccacagg tgtccactcc gaggtgcagc tggtggagtc tg    52

<210> SEQ ID NO 99
<211> LENGTH: 43
<212> TYPE: DNA
<213> ORGANISM: Recombinant

<400> SEQUENCE: 99
atgggccctt ggtggaagct gaagagacgg tgaccagggt gcc    43

<210> SEQ ID NO 100
<211> LENGTH: 59
<212> TYPE: DNA
<213> ORGANISM: Recombinant

<400> SEQUENCE: 100
ttgaattcag gtgggggcac ttctccctct atgaacattc cgtaggggcc actgtcttc    59

<210> SEQ ID NO 101
<211> LENGTH: 45
<212> TYPE: DNA
<213> ORGANISM: Recombinant

<400> SEQUENCE: 101
ttaacgattt cgaacgccac catgggatgg agctgtatca tcctc     45

<210> SEQ ID NO 102
<211> LENGTH: 43
<212> TYPE: DNA
<213> ORGANISM: Recombinant

<400> SEQUENCE: 102
gtcctaggtg agtagatcta tctgggataa gcatgctgtt ttc     43

<210> SEQ ID NO 103
<211> LENGTH: 29
<212> TYPE: DNA
<213> ORGANISM: Recombinant

<400> SEQUENCE: 103
gatctactca cctaggacgg tcagcttgg     29

<210> SEQ ID NO 104
<211> LENGTH: 22
<212> TYPE: PRT
<213> ORGANISM: Human

<400> SEQUENCE: 104

Thr Gln His Ser Arg Val Leu Ser Leu Tyr Asn Thr Ile Asn Pro Glu
1               5                   10                  15

Ala Ser Ala Ser Pro Cys
            20

<210> SEQ ID NO 105
<211> LENGTH: 10
<212> TYPE: PRT
<213> ORGANISM: Human

<400> SEQUENCE: 105

Arg Gln Leu Ser Leu Gln Gln Arg Met His
1               5                   10

<210> SEQ ID NO 106
<211> LENGTH: 10
<212> TYPE: PRT
<213> ORGANISM: Human

<400> SEQUENCE: 106

Asp Pro Met Asp Met Val Leu Lys Leu Cys
1               5                   10

<210> SEQ ID NO 107
<211> LENGTH: 10
<212> TYPE: PRT
<213> ORGANISM: Human

<400> SEQUENCE: 107

Trp Ser Glu Phe Met Arg Gln Ser Ser Leu
1               5                   10

<210> SEQ ID NO 108
<211> LENGTH: 10
<212> TYPE: PRT
<213> ORGANISM: Human

<400> SEQUENCE: 108

Val Glu Ser Thr Ser Leu Gln Phe Arg Gly

-continued

```
1               5                   10
```

<210> SEQ ID NO 109
<211> LENGTH: 17
<212> TYPE: PRT
<213> ORGANISM: Synthetic

<400> SEQUENCE: 109

```
Cys Gly Gly Thr Gln His Ser Arg Val Leu Ser Leu Tyr Asn Thr Ile
1               5                   10                  15

Asn
```

<210> SEQ ID NO 110
<211> LENGTH: 13
<212> TYPE: PRT
<213> ORGANISM: Synthetic

<400> SEQUENCE: 110

```
Gly Pro Glu Ala Ser Arg Pro Pro Lys Leu His Pro Gly
1               5                   10
```

<210> SEQ ID NO 111
<211> LENGTH: 115
<212> TYPE: PRT
<213> ORGANISM: Human

<400> SEQUENCE: 111

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Ser Tyr Val Pro Trp Gly Gln Gly Thr Leu Val Thr
            100                 105                 110

Val Ser Ser
        115
```

<210> SEQ ID NO 112
<211> LENGTH: 118
<212> TYPE: PRT
<213> ORGANISM: Human

<400> SEQUENCE: 112

```
Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Ser Val Arg Asn Asp Gly Ser Asn Thr Tyr Tyr Thr Asp Ser Val
    50                  55                  60

Lys Gly Arg Phe Thr Ile Pro Arg Asp Asn Thr Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95
Thr Ser Asp Pro Leu Arg Tyr Pro Ile Asp Tyr Trp Gly Gln Gly Thr
                100                 105                 110
Leu Val Thr Val Ser Ser
        115
```

<210> SEQ ID NO 113
<211> LENGTH: 345
<212> TYPE: DNA
<213> ORGANISM: Human

<400> SEQUENCE: 113

| gaggtgcagc | tggtggagtc | tgtggaggc  | ttagttcagc | ctggggggtc | cctgagactc | 60  |
| tcctgtgcag | cctctggatt | caccttcagt | agctactgga | tgcactgggt | ccgccaagct | 120 |
| ccagggaagg | ggctggtgtg | ggtctcacgt | attaatagtg | atgggagtag | cacaagctac | 180 |
| gcggactccg | tgaagggccg | attcaccatc | tccagagaca | acgccaagaa | cacgctgtat | 240 |
| ctgcaaatga | acagtctgag | agccgaggac | acggccgtgt | attactgtgc | aagggagaat | 300 |
| agttatgtgc | cttgggggca | gggcaccctg | gtcaccgtct | cctca      |            | 345 |

<210> SEQ ID NO 114
<211> LENGTH: 354
<212> TYPE: DNA
<213> ORGANISM: Human

<400> SEQUENCE: 114

| caggtgcaac | tgcaggagtc | gggggggaggc | gtggtccagc | ctggggggtc | cctgagactc | 60  |
| tcctgtgcag | cgtctggatt | caccttcagt | ggctatggca | tgcactgggt | ccgccaggct | 120 |
| ccaggcaagg | ggctggagtg | ggtggcatct | gtacggaacg | atggaagtaa | tacatactac | 180 |
| acagactccg | tgaagggccg | attcaccatc | cccagagaca | acaccaagaa | cacgctgtat | 240 |
| ctgcaaatga | acagcctgag | agccgaggac | acggccgtat | attactgtac | gtctgatcct | 300 |
| ttacgctatc | ctattgacta | ctggggccag | ggaaccctgg | tcaccgtctc | gagt       | 354 |

<210> SEQ ID NO 115
<211> LENGTH: 369
<212> TYPE: DNA
<213> ORGANISM: Human

<400> SEQUENCE: 115

| caggtcacct | tgaaggagtc | tggggggaagc | gtggtccagc | ctggggaggtc | cctgagactc | 60  |
| tcctgtgcag | cctctggatt | caccttcagt | agctatggca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tccagagaca | attccaagaa | cacgcagtat | 240 |
| ctgcaaatga | acagcctgag | agctgaagac | acggcagagt | attactgtgc | gagaactggg | 300 |
| gaatatagtg | gccacgcatc | tactggagag | aacgtctggg | ccgggggcac | cctggtcacc | 360 |
| gtctcgagt  |            |            |            |            |            | 369 |

<210> SEQ ID NO 116
<211> LENGTH: 123
<212> TYPE: PRT
<213> ORGANISM: Human

-continued

```
<400> SEQUENCE: 116

Gln Val Thr Leu Lys Glu Ser Gly Gly Ser Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Glu Tyr Tyr Cys
                85                  90                  95

Ala Arg Thr Gly Glu Tyr Ser Gly His Ala Ser Thr Gly Glu Asn Val
            100                 105                 110

Trp Gly Arg Gly Thr Leu Val Thr Val Ser Ser
            115                 120

<210> SEQ ID NO 117
<211> LENGTH: 336
<212> TYPE: DNA
<213> ORGANISM: Human

<400> SEQUENCE: 117
tcctatgtgc tgactcaccc ccctcagtg tctgggaccc ccgggcagag agtcaccatc    60
tcttgttctg gaggcagatc caacatcggc agtaatactg taaagtggta tcagcagctc   120
ccaggaacgc cccccaaact cctcatctat ggcaatgatc agcggccctc agggatccct   180
gaccgattct ctggctccaa gtctggcacc tcagcctccc tggccatcac tggggtccag   240
gctgaagacg aggctgacta ttactgccag tcatatgaca gcagcctgag gggttcgagg   300
gtcttcggaa ctgggaccaa ggtcaccgtc ctaggt                             336

<210> SEQ ID NO 118
<211> LENGTH: 112
<212> TYPE: PRT
<213> ORGANISM: Human

<400> SEQUENCE: 118

Ser Tyr Val Leu Thr His Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Pro Pro Lys Leu Leu
        35                  40                  45

Ile Tyr Gly Asn Asp Gln Arg Pro Ser Gly Ile Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Arg Gly Ser Arg Val Phe Gly Thr Gly Thr Lys Val Thr Val Leu Gly
            100                 105                 110

<210> SEQ ID NO 119
<211> LENGTH: 381
<212> TYPE: DNA
```

<213> ORGANISM: Human

<400> SEQUENCE: 119

```
caggtacaac ctcagcagtc tgggggagag gtgaagcagc ctggggcctc cgtgaaggtt      60
tcctgtaagg cgtctggata caccttcacc agcttctata tgaactgggt gcgacaggcc     120
cccggacaag ggcttgagtg gatgggaata atcagccctc gtggtggtac gacaagttac     180
gcacagaact tccagggcag agtcaccatg accagggaca cgtccacaag cacagtctac     240
atggagctga gcagcctgag atctgaggac acggccgtgt attattgtgc gataattggg     300
ggtactacta tgagagtagg ggggcccgat gcttttgata tctggggcca agggacaatg     360
gtcaccgtca ccgtctcttc a                                               381
```

<210> SEQ ID NO 120
<211> LENGTH: 127
<212> TYPE: PRT
<213> ORGANISM: Human

<400> SEQUENCE: 120

```
Gln Val Gln Pro Gln Gln Ser Gly Gly Glu Val Lys Gln Pro Gly Ala
1               5                   10                  15

Ser Val Lys Val Ser Cys Lys Ala Ser Gly Tyr Thr Phe Thr Ser Phe
            20                  25                  30

Tyr Met Asn Trp Val Arg Gln Ala Pro Gly Gln Gly Leu Glu Trp Met
        35                  40                  45

Gly Ile Ile Ser Pro Arg Gly Gly Thr Thr Ser Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ile Ile Gly Gly Thr Thr Met Arg Val Gly Gly Pro Asp Ala Phe
            100                 105                 110

Asp Ile Trp Gly Gln Gly Thr Met Val Thr Val Thr Val Ser Ser
        115                 120                 125
```

<210> SEQ ID NO 121
<211> LENGTH: 381
<212> TYPE: DNA
<213> ORGANISM: Human

<400> SEQUENCE: 121

```
gaggtgcagc tggtggagtc tgggggaggc gtggtccagc ctgggaggtc cctgagactc      60
tcctgtgcag cgtctggatt caccttcagg aactatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agtcgaggac acggctgttt attactgtgc gagaagatgg     300
tatggtggca gtggttattg gggccacttc tactcctaca tggacggctg ggcaaaggg     360
accaaggtca ccgtctcctc a                                               381
```

<210> SEQ ID NO 122
<211> LENGTH: 127
<212> TYPE: PRT
<213> ORGANISM: Human

<400> SEQUENCE: 122

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Arg Trp Tyr Gly Gly Ser Gly Tyr Trp Gly His Phe Tyr Ser
            100                 105                 110

Tyr Met Asp Gly Trp Gly Lys Gly Thr Lys Val Thr Val Ser Ser
        115                 120                 125

<210> SEQ ID NO 123
<211> LENGTH: 324
<212> TYPE: DNA
<213> ORGANISM: Human

<400> SEQUENCE: 123
gaagttgtgc tgactcagtc tccatcctcc ctgtctgcat ctgtaggaga cagagtcacc      60
atcacttgcc gggcaagtca gggcattgga gatgatttgg gctggtatca gcagaagcca     120
gggaaagccc ctatcctcct gatctatggt acatccactt tacaaagtgg ggtcccgtca     180
aggttcagcg gcagtggatc tggcacagat ttcactctca ccatcaacag cctgcagcct     240
gaagattttg caacttatta ctgtctacaa gattccaatt acccgctcac tttcggcgga     300
gggacacgac tggagattaa acgt                                             324

<210> SEQ ID NO 124
<211> LENGTH: 108
<212> TYPE: PRT
<213> ORGANISM: Human

<400> SEQUENCE: 124

Glu Val Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Arg
            100                 105

```
<210> SEQ ID NO 125
<211> LENGTH: 14
<212> TYPE: PRT
<213> ORGANISM: synthetic

<400> SEQUENCE: 125

Thr Gln Tyr Ser Lys Val Leu Ser Leu Tyr Asn Gln His Asn
1               5                   10
```

What is claimed is:

1. An isolated antibody or antibody fragment thereof comprising an antibody-antigen binding domain of a human antibody specific for TGFβ isoform TGFβ2, said antibody-antigen binding domain comprising;
   (a) a VH domain selected from the group consisting of the 6H1 VH domain of which the amino acid sequence is shown in FIG. 2(a)(i) (SEQ ID NO: 6), the 11E6 VH domain of which the amino acid sequence is shown in FIG. 2(a)(ii) (SEQ ID NO: 37), the Gold 11-VH domain of which the amino acid sequence is shown in FIG. 2(a)(iii) (SEQ ID NO: 116), the 1-G2 VH domain of which the amino acid sequence is shown in FIG. 2(a)(v) (SEQ ID NO: 120) and the 1-H-6 VH domain of which the amino acid sequence is shown in FIG. 2(a)(vi) (SEQ ID NO: 122); and
   (b) a VL domain selected from the group consisting of the 6B1 VL domain of which the amino acid sequence is shown in FIG. 2(b)(iii) (SEQ ID NO:43), the 6H1 VL domain of which the amino acid sequence is shown in FIG. 2(b)(i) (SEQ ID NO: 39), the 6A5 VL domain of which the amino acid sequence is shown in FIG. 2(b)(ii) (SEQ ID NO:41), the 11E6 VL domain of which the amino acid sequence is shown in FIG. 2(b)(iv) (SEQ ID NO:45), the 14F12 VL domain of which the amino acid sequence is shown in FIG. 2(b)(v) (SEQ ID NO:47) and the 6H1 VL domain of which the amino acid sequence is shown in FIG. 2(b)(vi) (SEQ ID NO:124).

2. The antibody or antibody fragment thereof according to claim 1 which is in the form of scFv.

3. The antibody or antibody fragment thereof according to claim 1 which is in the form of a whole antibody.

4. An isolated antibody or antibody fragment thereof comprising an antibody-antigen binding domain of a human antibody specific for TGFβ isoform TGFβ2, said antibody-antigen binding domain comprising;
   (a) a VH domain comprising the 6H1 VH domain CDRs shown in FIG. 19(i), wherein VH CDR1 has the amino acid sequence set forth in SEQ ID NO: 126, VH CDR2 has the amino acid sequence set fort in SEQ ID NO: 127 and VH CDR3 has the amino acid sequence set forth in SEQ ID NO: 128, and
   (b) a VL domain comprising VL domain CDRs selected from the group consisting of:
      (i) the 6B1 VL domain CDRS shown in FIG. 19(ii), wherein VL CDR1 has the amino acid sequence set forth in SEQ ID NO: 129, VL CDR2 has the amino acid sequence set fort in SEQ ID NO: 130 and VH CDR3 haste amino acid sequence set forth in SEQ ID NO: 131,
      (ii) the 6A5 VL domain CDRs shown in FIG. 19(iii), wherein VL CDR1 has the amino acid sequence set forth in SEQ ID NO: 132, VL CDR2 has the amino acid sequence set forth in SEQ ID NO: 133, and VH CDR3 has the amino acid sequence set forth in SEQ ID NO: 134, and
      (iii) the 6H1 VL CDRs shown in FIG. 19(iv), wherein VL CDR1 has the amino acid sequence set forth in SEQ ID NO: 135, VL CDR2 has the amino acid sequence set forth in SEQ ID NO: 136, and VH CDR3 has the amino acid sequence set forth in SEQ ID NO: 137.

5. The antibody or antibody fragment thereof according to claim 4 which is in the form of scFv.

6. The antibody or antibody fragment thereof according to claim 4 which is in the form of a whole antibody.

7. The antibody or antibody fragment thereof according to claim 4 wherein the VH domain is the 6H1 VH domain of which the amino acid sequence is shown in FIG. 2(a)(i) (SEQ ID NO: 6).

8. The antibody or antibody fragment thereof according to claim 7 which is in the form of scFv.

9. The antibody or antibody fragment thereof according to claim 7 which is in the form of a whole antibody.

10. The antibody or antibody fragment thereof according to claim 7 wherein the VL domain is selected from the 6B1 VL domain, of which the amino acid sequence is shown in FIG. 2(b)(iii) (SEQ ID NO: 43), the 6H1 VL domain, of which the amino acid sequence is shown in FIG. 2(b)(i) (SEQ ID NO: 124), and the 6A5 VL domain, of which the amino acid sequence is shown in FIG. 2(b)(ii) (SEQ ID NO:41).

11. The antibody or antibody fragment thereof according to claim 10 which is in the form of scFv.

12. The antibody or antibody fragment thereof according to claim 10 which is in the form of a whole antibody.

13. An isolated antibody or antibody fragment thereof comprising an antibody-antigen binding domain of a human antibody specific for TGFβ isoform TGFβ2, said antibody-antigen binding domain comprising;
   (a) a VH domain comprising the 6H1 VH domain CDRs shown in FIG. 19(i), wherein VH CDR1 has the amino acid sequence set forth in SEQ ID NO: 126, VIA CDR2 has the amino acid sequence set forth in SEQ ID NO: 127 and VH CDR3 has the amino acid sequence set forth in SEQ ID NO: 128, and
   (b) a VL domain comprising the 6B1 VL domain CDRs shown in FIG. 19(ii), wherein VL CDR1 has the amino acid sequence set forth in SEQ ID NO: 129, VL CDR2 has the amino acid sequence set forth in SEQ ID NO: 130 and VH CDR3 has the amino acid sequence set forth in SEQ ID NO: 131.

14. The antibody or antibody fragment thereof according to claim 13 which is in the form of scFv.

15. The antibody or antibody fragment thereof according to claim 13 which is in the form of a whole antibody.

16. An isolated antibody or antibody fragment there of comprising an antibody-antigen binding domain of a human antibody specific for TGFβ isoform TGFβ2, said antibody-antigen binding domain comprising the VH domain 6H1 VH of which the amino acid sequence is shown in FIG. 2(a)(i) (SEQ ID NO: 6) and the VL domain 6B1 VL, of which the amino acid sequence is shown in FIG. 2(b)(iii) (SEQ ID NO: 43).

17. The antibody or antibody fragment thereof according to claim 16 which is in the form of scFv.

18. The antibody or antibody fragment thereof according to claim 16 which is in the form of a whole antibody.

19. A composition which comprises an antibody or antibody fragment thereof as in any one of claims 1, 4, 7, 10, 13 or 16 and an excipient.

20. A pharmaceutical composition comprising an antibody or antibody fragment thereof as in any one of claims 1, 4, 7, 10, 13 or 16 and a pharmaceutically acceptable excipient.

\* \* \* \* \*

UNITED STATES PATENT AND TRADEMARK OFFICE
CERTIFICATE OF CORRECTION

PATENT NO.         : 7,368,111 B2
APPLICATION NO. : 10/625307
DATED                 : May 6, 2008
INVENTOR(S)       : Julia Elizabeth Thompson et al.

It is certified that error appears in the above-identified patent and that said Letters Patent is hereby corrected as shown below:

Title Page,

Page 1, Field 63 - Related U.S. Application Data, change "Continuation-in-part of application No. 08/571,755, filed on Dec. 13, 1995, now abandoned, and a continuation of application No. 09/054,847, filed on Apr. 3, 1998, now abandoned, which is a continuation of application No. PCT/GB96/02450, filed on Oct. 7, 1996" to --Continuation-in-part of application No. 08/571,755, filed on Dec. 13, 1995, now abandoned, and a continuation-in-part of application No. 09/054,847, filed on Apr. 3, 1998, now abandoned, which is a continuation of application No. PCT/GB96/02450, filed on Oct. 7, 1996.--

Column 1, lines 6-11, change "This application is a continuation-in-part of U.S. patent application Ser. No. 08/571,755 filed Dec. 13, 1995 (now abandoned) and a continuation of U.S. patent application Ser. No. 09/054,847 filed Apr. 3, 1998 (now abandoned) which is in turn a continuation of PCT/GB96/02450 filed on Oct. 7, 1996." to --This application is a continuation-in-part of U.S. patent application Ser. No. 08/571,755 filed Dec. 13, 1995 (now abandoned) and a continuation-in-part of U.S. patent application Ser. No. 09/054,847 filed Apr. 3, 1998 (now abandoned) which is in turn a continuation of PCT/GB96/02450 filed on Oct. 7, 1996.--

In the Claims:

Claim 1, Column 111, line 28, change "1-H-6" to --1-H6--

Claim 4, Column 111, line 55, change "fort" to --forth--

Claim 4, Column 111, line 63, change "fort" to --forth--

UNITED STATES PATENT AND TRADEMARK OFFICE
CERTIFICATE OF CORRECTION

PATENT NO. : 7,368,111 B2
APPLICATION NO. : 10/625307
DATED : May 6, 2008
INVENTOR(S) : Julia Elizabeth Thompson et al.

It is certified that error appears in the above-identified patent and that said Letters Patent is hereby corrected as shown below:

Claim 4, Column 111, lines 63-64, change "VH CDR3 haste" to --VL CDR3 has the--

Claim 4, Column 112, line 16, change "VH" to --VL--

Claim 4, Column 112, line 22, change "VH" to --VL--

Claim 13, Column 112, line 56, change "VIA" to --VH--

Claim 13, Column 112, line 64, change "VH" to --VL--

Claim 16, Column 113, line 3, change "there of" to --thereof--

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,368,111 B2 Page 1 of 16
APPLICATION NO. : 10/625307
DATED : May 6, 2008
INVENTOR(S) : Thompson et al.

It is certified that error appears in the above-identified patent and that said Letters Patent is hereby corrected as shown below:

Column 55, line 1, insert sequence listing. (attached)

Signed and Sealed this

Fourteenth Day of October, 2008

JON W. DUDAS
*Director of the United States Patent and Trademark Office*

SEQUENCE LISTING

<110> Thompson, Julia E.
      Vaughan, Tristan J.
      Williams, Andrew J.
      Green, Jonathan A.
      Jackson, Ronald H.
      Bacon, Louise
      Johnson, Kevin S.
      Wilton, Alison J.
      Tempest, Philip R.
      Pope, Anthony R.

<120> Specific Binding Members for Human Transforming Growth Factor Beta: Materials and Methods

<130> 05569.0007.CPUS02

<140> 10625307
<141> 2003-07-23

<150> 10/625,307
<151> 2003-07-23

<150> 09/054,847
<151> 1998-04-03

<150> 08/571,755
<151> 1995-12-13

<150> PCT/GB96/02450
<151> 1996-10-07

<160> 137

<170> PatentIn version 3.1

<210> 1
<211> 5
<212> PRT
<213> Human

<400> 1

Arg Val Leu Ser Leu
1               5

<210> 2
<211> 14
<212> PRT
<213> Human

<400> 2

Thr Gln His Ser Arg Val Leu Ser Leu Tyr Asn Thr Ile Asn
1               5                   10

```
<210> 3
<211> 17
<212> PRT
<213> Human

<400> 3

Cys Gly Gly Thr Gln Tyr Ser Lys Val Leu Ser Leu Tyr Asn Gln His
1               5                   10                  15

Asn

<210> 4
<211> 14
<212> PRT
<213> Human

<400> 4

Thr Gln Tyr Ser Lys Val Leu Ser Leu Tyr Asn Gln His Asn
1               5                   10

<210> 5
<211> 345
<212> DNA
<213> Human

<400> 5
gaggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatgg acagcctgag agccgaggac acggccgtgt attactgtgg aagaacgctg     300
gagtctagtt tgtggggcca aggcaccctg gtcaccgtct cctca                    345

<210> 6
<211> 115
<212> PRT
<213> Human

<400> 6

Glu Val Gln Leu Val Glu Ser Gly Gly Gly Val Val Gln Pro Gly Arg
1               5                   10                  15
```

```
        Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
                    35                  40                  45

Ala Val Ile Trp Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
        65                  70                  75                  80

Leu Gln Met Asp Ser Leu Arg Ala Glu Asp Thr Ala Val Tyr Tyr Cys
                        85                  90                  95

Gly Arg Thr Leu Glu Ser Ser Leu Trp Gly Gln Gly Thr Leu Val Thr
                    100                 105                 110

Val Ser Ser
                115

<210>  7
<211>  369
<212>  DNA
<213>  Human

<400>  7
caggtgcaac tggtggagtc tgggggaggc gtggtccagc ctgggaggtc cctgagactc        60
tcctgtgcag cctctggatt caccttcagt agctatggca tgcactgggt ccgccaggct       120
ccaggcaagg ggctggagtg ggtggcagtt atatcatatg atggaagtaa taaatactat       180
gcagactccg tgaagggccg attcaccatc tccagagaca attccaagaa cacgctgtat       240
ctgcaaatga acagcctgag agctgaggac acggctgtgt attactgtgc gaaaactggg       300
gaatatagtg gctacgattc tagtggtgtg gacgtctggg gcaaagggac cacggtcacc       360
gtctcctca                                                               369

<210>  8
<211>  123
<212>  PRT
<213>  Human

<400>  8
```

```
    Gln Val Gln Leu Val Glu Ser Gly Gly Gly Val Val Gln Pro Gly Arg
    1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Lys Thr Gly Glu Tyr Ser Gly Tyr Asp Ser Ser Gly Val Asp Val
                100                 105                 110

Trp Gly Lys Gly Thr Thr Val Thr Val Ser Ser
                115                 120
```

<210> 9
<211> 369
<212> DNA
<213> Human

<400> 9

```
caggtgcagc tggtgcagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtat aaatactat   180
gcagactccg tgaagggccg attcaccatc tccagagaca attccaagaa cacgctgtat   240
ctgcaaatga acagcctgag agctgaggac acggctgtgt attactgtgc gcgaactggt   300
gaatatagtg gctacgatag cagtggtgtg gagctctggg gcaagggac cacggtcacc   360
gtctcctca                                                          369
```

<210> 10
<211> 123
<212> PRT
<213> Human

<400> 10

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Ser Gly Val Glu Leu
            100                 105                 110

Trp Gly Gln Gly Thr Thr Val Thr Val Ser Ser
            115                 120

<210> 11
<211> 369
<212> DNA
<213> Human

<400> 11
caggtgcaac tggtggagtc tgggggaggc gtggtccagc ctgggaggtc cctgagactc      60
tcctgtgcag cctctggact caccttcagt agctatggca tgcactgggt ccgccagcct     120
ccagccaagg ggctggagtg ggtggcagtt atatcatatg atggaagtag taaatactat     180
gcagactccg tgaagggccg attcaccatc tccagagaca attccaagaa cacgctgtat     240
ctgcaaatga acagcctgag agctgaggac acggctgtgt attactgtgc gcgaactggt     300
gaatatagtg gctacgacac gagtggtgtg gagctctggg gcaagggac cacggtcacc     360 gtctcctca                                                             369

<210> 12

<211> 123
    <212> PRT
    <213> Human

<400> 12

Gln Val Gln Leu Val Glu Ser Gly Gly Val Val Gln Pro Gly Arg
    1               5                   10                  15

Ser Leu Arg Leu Ser Cys Ala Ala Ser Gly Leu Thr Phe Ser Ser Tyr
                20                  25                  30

Asp Met His Trp Val Arg Gln Pro Pro Ala Lys Gly Leu Glu Trp Val
            35                  40                  45

Ala Val Ile Ser Tyr Asp Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Arg Thr Gly Glu Tyr Ser Gly Tyr Asp Thr Ser Gly Val Glu Leu
                100                 105                 110

Trp Gly Gln Gly Thr Thr Val Thr Val Ser Ser
            115                 120

<210> 13
    <211> 324
    <212> DNA
    <213> Human

<400> 13
    gacatcgtga tgacccagtc tccttccacc ctgtctgcat ctgtaggaga cagagtcacc     60
atcacttgcc gggccagtca gggtattagt agctggttgg cctggtatca gcagaaacca    120
gggagagccc ctaaggtctt gatctataag gcatctactt tagaaagtgg ggtcccatca    180
aggttcagcg gcagtggatc tgggacagat ttcactctca ccatcagcag tctgcaacct    240
gaagattttg caacttacta ctgtcaacag agttacagta cccgtggac gttcggccaa    300 gggaccaagc tggagatcaa acgt                                          324

```
<210> 14
<211> 108
<212> PRT
<213> Human

<400> 14
```

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg
            100                 105

```
<210> 15
<211> 342
<212> DNA
<213> Human

<400> 15
gacatcgtga tgacccagtc tccagactcc ctggctgtgt ctctgggcga gagggccacc    60
atcaactgca agtccagcca gagtctttta tacagctaca acaagatgaa ctacttagct   120
tggtaccagc agaaaccagg acagcctcct aagctgctca ttaactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatgcaact   300
cctctgacgt tcggccacgg gaccaaggtg gaaatcaaac gt                      342

<210> 16
<211> 114
<212> PRT
```

<213> Human

<400> 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Tyr Asn Lys Met Asn Tyr Leu Ala Trp Tyr Gln Gln Lys Pro Gly Gln
        35                  40                  45

Pro Pro Lys Leu Leu Ile Asn Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Thr Pro Leu Thr Phe Gly His Gly Thr Lys Val Glu Ile
                100                 105                 110

Lys Arg

<210> 17
<211> 330
<212> DNA
<213> Human

<400> 17
cacgttatac tgactcagga ccctgctgtg tctgtggcct tgggacagac agtcaggatc      60
acgtgccaag gagacagcct caaaagctac tatgcaagtt ggtaccagca gaagccagga     120
caggcccctg tacttgtcat ctatggtgaa acagccggcc ctccgggat cccagaccga      180
ttctctggct ccagctcagg aaacacagct tccttgacca tcactggggc tcaggcggaa     240
gatgaagctg actattactg taactcccgg gacagcagtg gtacccatct agaagtgttc     300
ggcggaggga ccaagctgac cgtcctaggt                                     330

<210> 18
<211> 110

<212> PRT
<213> Human

<400> 18

His Val Ile Leu Thr Gln Asp Pro Ala Val Ser Val Ala Leu Gly Gln
1               5                   10                  15

Thr Val Arg Ile Thr Cys Gln Gly Asp Ser Leu Lys Ser Tyr Tyr Ala
                20                  25                  30

Ser Trp Tyr Gln Gln Lys Pro Gly Gln Ala Pro Val Leu Val Ile Tyr
            35                  40                  45

Gly Glu Asn Ser Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr His
                85                  90                  95

Leu Glu Val Phe Gly Gly Gly Thr Lys Leu Thr Val Leu Gly
                100                 105                 110

<210> 19
<211> 17
<212> PRT
<213> Human

<400> 19

Ala Arg Thr Gly Glu Tyr Ser Gly Tyr Asp Ser Ser Gly Val Asp Val
1               5                   10                  15

Trp

<210> 20
<211> 17
<212> PRT
<213> Human

<400> 20

Ala Arg Thr Gly Glu Tyr Ser Gly Tyr Asp Thr Ser Gly Val Glu Leu
1               5                   10                  15

Trp

<210> 21
<211> 17
<212> PRT
<213> Human

<400> 21

Ala Arg Thr Arg Glu Tyr Ser Gly His Asp Ser Ser Gly Val Asp Asp
1               5                   10                  15

Trp

<210> 22
<211> 17
<212> PRT
<213> Human

<400> 22

Ala Arg Thr Gly Pro Phe Ser Gly Tyr Asp Ser Ser Gly Glu Asp Val
1               5                   10                  15

Arg

<210> 23
<211> 17
<212> PRT
<213> Human

<400> 23

Ala Arg Thr Glu Glu Tyr Ser Gly Tyr Asp Ser Ser Gly Val Asp Val
1               5                   10                  15

Trp

<210> 24
<211> 17
<212> PRT
<213> Human

<400> 24

```
Ala Gln Thr Arg Glu Tyr Thr Gly Tyr Asp Ser Ser Gly Val Asp Val
1               5                   10                  15

Trp

<210> 25
<211> 17
<212> PRT
<213> Human

<400> 25

Ala Arg Thr Glu Glu Tyr Ser Gly Phe Asp Ser Thr Gly Glu Asp Val
1               5                   10                  15

Trp

<210> 26
<211> 17
<212> PRT
<213> Human

<400> 26

Ala Arg Thr Glu Glu Phe Ser Gly Tyr Asp Ser Ser Gly Val Asp Val
1               5                   10                  15

Trp

<210> 27
<211> 17
<212> PRT
<213> Human

<400> 27

Ala Arg Thr Gly Glu Tyr Ser Gly Tyr His Ser Ser Gly Val Asp Val
1               5                   10                  15

Arg

<210> 28
<211> 17
<212> PRT
```

<213> Human

<400> 28

Ala Arg Thr Glu Glu Phe Ser Gly Tyr Asp Ser Ser Gly Val Asp Val
1               5                   10                  15

Trp

<210> 29
<211> 17
<212> PRT
<213> Human

<400> 29

Ala Arg Ala Gly Pro Phe Ser Gly Tyr Asp Ser Ser Gly Glu Asp Val
1               5                   10                  15

Arg

<210> 30
<211> 17
<212> PRT
<213> Human

<400> 30

Ala Arg Thr Gly Pro Phe Ser Gly Tyr Asp Ser Ser Gly Glu Asp Val
1               5                   10                  15

Trp

<210> 31
<211> 17
<212> PRT
<213> Human

<400> 31

Ala Arg Thr Glu Glu Phe Ser Gly Tyr Asp Ser Ser Gly Val Asp Val
1               5                   10                  15

Trp

```
<210>  32
<211>  17
<212>  PRT
<213>  Human

<400>  32

Ala Arg Thr Gly Glu Tyr Ser Gly Tyr Asp Ser Ser Gly Glu Leu Val
1               5                   10                  15

Trp

<210>  33
<211>  17
<212>  PRT
<213>  Human

<400>  33

Ala Arg Thr Glu Glu Phe Ser Gly Tyr Asp Ser Thr Gly Glu Glu Val
1               5                   10                  15

Trp

<210>  34
<211>  17
<212>  PRT
<213>  Human

<400>  34

Ala Arg Thr Glu Glu Phe Ser Gly Tyr Asp Ser Ser Gly Val Asp Val
1               5                   10                  15

Trp

<210>  35
<211>  17
<212>  PRT
<213>  Human

<400>  35

Ala Arg Thr Gly Glu Tyr Ser Gly Tyr Asp Ser Ser Gly Glu Asp Val
1               5                   10                  15

Trp
```

<210> 36
<211> 350
<212> DNA
<213> Human

<400> 36
```
gagattcagc tggtggagtc tgggggaggc gtggtccagc ctgggagatc cctgagactc      60
tcctgtgcag cctctggatt caccttcagt agctatgcta tgcactgggt ccgccaggct     120
ccagccaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggccgtgt attactgtgc aagagcgggg     300
ttggaaacga cgtggggcca aggaaccctg gtcaccgtct cctcaagtgg                350
```

<210> 37
<211> 117
<212> PRT
<213> Human

<400> 37

Glu Ile Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Ala Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Glu Thr Thr Trp Gly Gln Gly Thr Leu Val Thr
            100                 105                 110

```
Val Ser Ser Ser Gly
        115

<210>  38
<211>  324
<212>  DNA
<213>  Human

<400>  38
gatgttgtga tgactcagtc tccatcctcc ctgtctgcat ctgtaggaga cagagtcacc      60
atcacttgcc gggccagtca gggcattagc aattatttag cctggtatca gcaaaaacca     120 gggaaa
```